(12) United States Patent
Lomonossoff et al.

(10) Patent No.: US 8,519,113 B2
(45) Date of Patent: Aug. 27, 2013

(54) BIPARTITE SYSTEM, METHOD AND COMPOSITION FOR THE CONSTITUTIVE AND INDUCIBLE EXPRESSION OF HIGH LEVELS OF FOREIGN PROTEINS IN PLANTS

(75) Inventors: George Lomonossoff, Norwich (GB); Li Liu, New Malden (GB); Carmen Canizares, Malaga (ES); Marc-Andre D'Aoust, Quebec (CA); Louis-Philippe Vezina, Neuville (CA)

(73) Assignee: Plant Bioscience Limited, Norwich (GB)

( * ) Notice: Subject to any disclaimer, the term of this patent is extended or adjusted under 35 U.S.C. 154(b) by 904 days.

(21) Appl. No.: 12/300,922

(22) PCT Filed: May 22, 2006

(86) PCT No.: PCT/IB2006/003548
§ 371 (c)(1),
(2), (4) Date: Nov. 14, 2008

(87) PCT Pub. No.: WO2007/135480
PCT Pub. Date: Nov. 29, 2007

(65) Prior Publication Data
US 2009/0181460 A1   Jul. 16, 2009

(51) Int. Cl.
*C12N 15/83* (2006.01)
*C12N 15/40* (2006.01)
*C12N 7/01* (2006.01)
*C12N 5/14* (2006.01)
*A01H 5/00* (2006.01)

(52) U.S. Cl.
USPC ............... 536/23.72; 435/320.1; 435/419; 800/280; 800/288

(58) Field of Classification Search
USPC ....................................................... 800/278
See application file for complete search history.

(56) References Cited

U.S. PATENT DOCUMENTS 7,618,815 B2 * 11/2009 Ghabrial et al. ............ 435/320.1
2005/0091706 A1 * 4/2005 Klimyuk et al. .............. 800/278

FOREIGN PATENT DOCUMENTS
WO   98/56933   12/1998

OTHER PUBLICATIONS

Canizarest, M.C., Liu, L., Perrin, Y., Tsakiris, E., and Lomonossoff, G.P. (2006) A bipartite system for the constitutive and inducible expression of high levels of foreign proteins in platns. Plant Biotechnology Journal 4: 183-193.*
Lomonossoff et al. Cowpea mosaic virus as a cersatile system for the expression of foreign peptides and proteins in legumes. Molecular Farming, Proceedings of the OECD workshop, La Grande Motte, France, Sep. 3-6, 2000 (2001), pp. 151-160.*
Verver et al. Studies on the movement of Cowpea mosaic virus using the jellyfish green fluorescent protein. (1998) Virology. 242: 22-27.*
Verver et al. Studies on the movement of Cowpea mosaic virus using the jellyfish green florescent protein (1998) Virology 242: 22-27.*
Gleba et al. Engineering viral expression vectors for plant: the full virus and the deconstructed virus strategies (2004) Curr. Opin in Plant Biol. 7:182-188.*
Verch et al. Expression an assembly of a full-length monocolonal antibody in plants using a plant virus vector (1998) J. of Immunnol. Meth. 220: 69-75.*
Yusibov et al. Antigens produced in plants by infection with chimeric plant virusses immunize against rabied virus and HIV-1 (1997) Proc. Nat. Acad. Sci 94: 5784-5788.*
Canizares, M., et al. "A bipartite system for the constitutive and inducible expression of high levels of foreign proteins in plants." Plant Biotechnology Journal, 4(2): 186-189 (Mar. 2006).
Liu, L., et al. "Cowpea mosaic virus-based systems for the production of antigens and antibodies in plants." Vaccine, 23(15): 1788-1792 (Mar. 7, 2005).
Mechtcheriakova, et al. "The use of viral vectors to produce hepatitis B virus core particles in plants." Journal of Virological Methods, 131(1): 10-15 (Jan. 2006).
Liu, L., et al. "Cowpea mosaic virus RNA-1 acts as an amplicon whose effects can be counteracted by a RNA-2-encoded supressor of silencing." Virology, 323(1): 37-48 (May 20, 2004).
Liu, L., et al. "Agroinfection as a rapid method for propagating Cowpea mosaic virus-based constructs." Journal of Virological Methods, 105(2): 343-348 (Sep. 2002).

* cited by examiner

*Primary Examiner* — Russell Kallis
*Assistant Examiner* — Steven Bernacki
(74) *Attorney, Agent, or Firm* — Dann, Dorfman, Herrell & Skillman; Kathleen D. Rigaut

(57) ABSTRACT

This invention comprises a combined transgene/virus vector system for the expression of heterologous proteins in plants. While exemplified with respect to the bipartite RNA plant virus, Cowpect mosaic virus (CPMV), other bipartite viral systems may be used to advantage according to the method, system and composition described in detail herein.

25 Claims, 13 Drawing Sheets

(Fig. 1a)
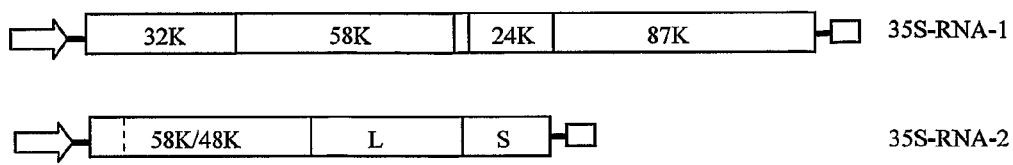
(Fig.1b)
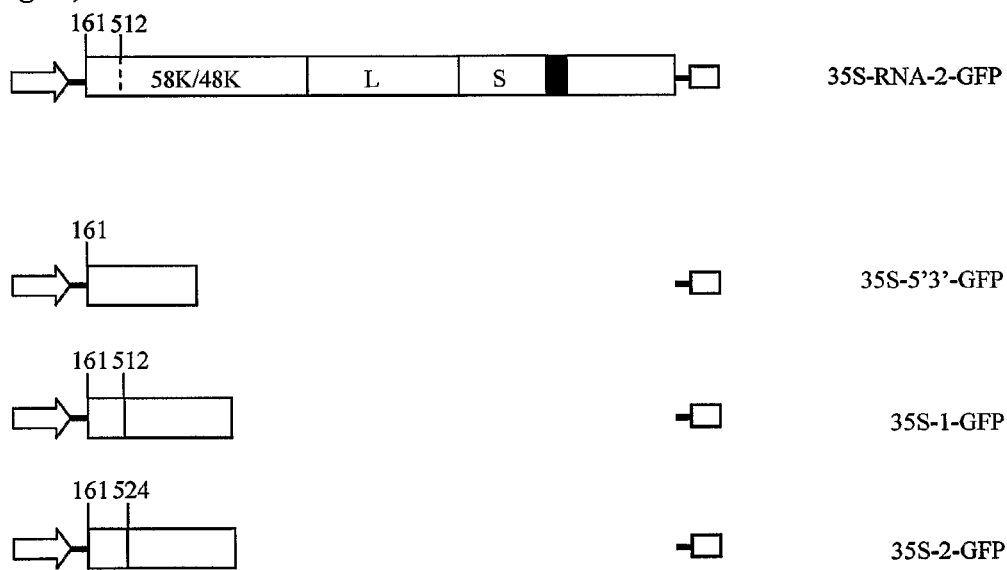

(a)
(b)
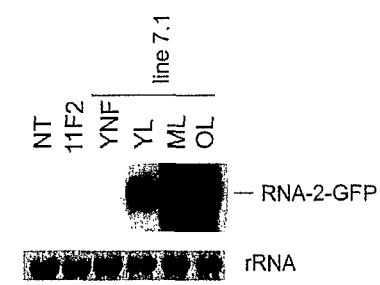
(c)
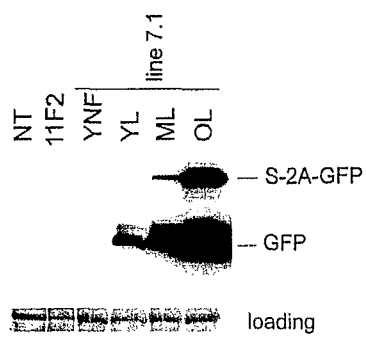
Figure 3

Figure 11
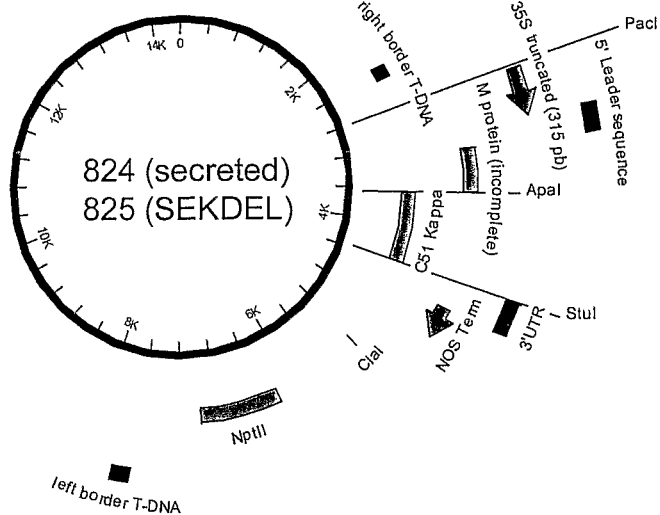
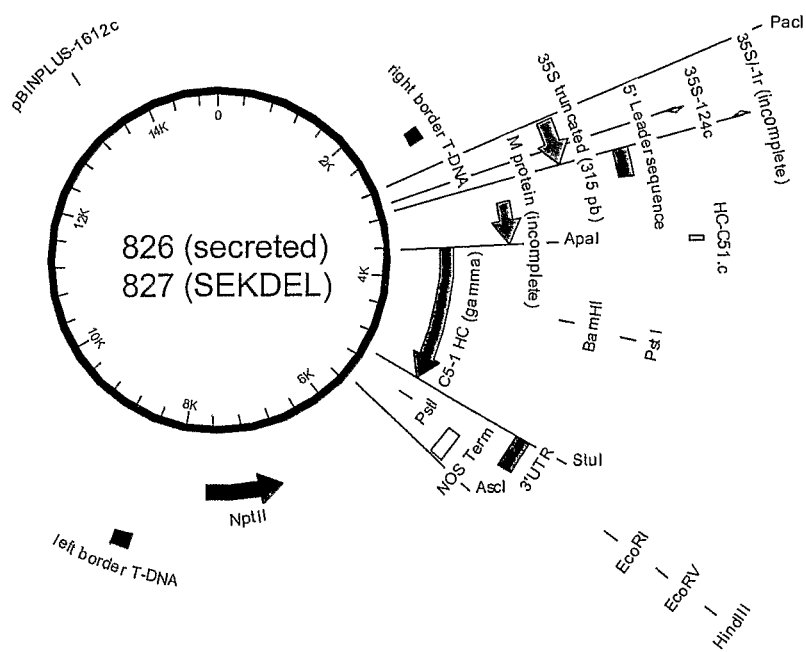

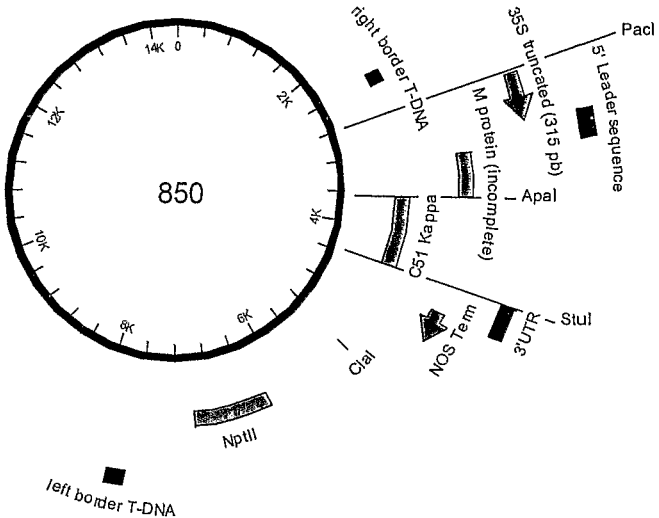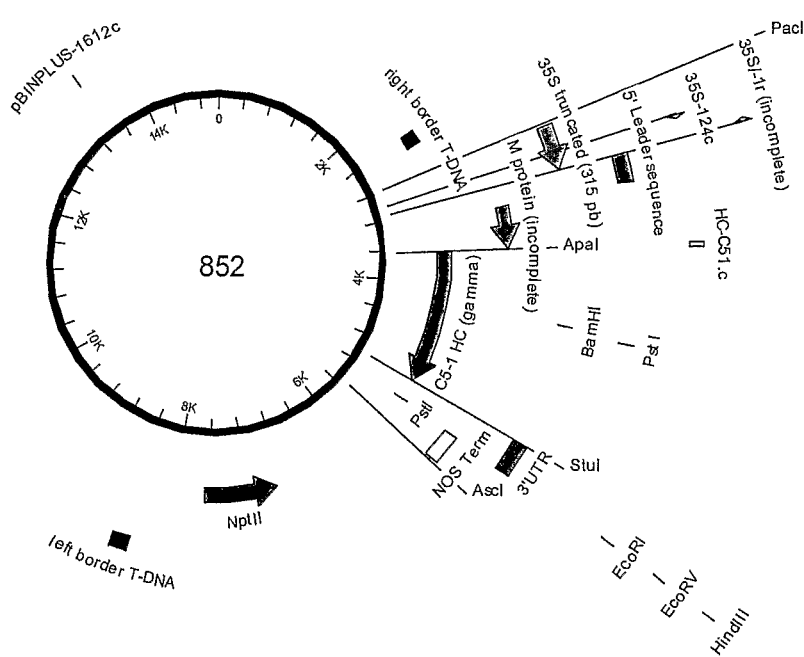
Figure 13

US 8,519,113 B2

```
                         SEQUENCE LISTING

<160> NUMBER OF SEQ ID NOS: 30

<210> SEQ ID NO 1
<211> LENGTH: 35
<212> TYPE: DNA
<213> ORGANISM: Artificial sequence
<220> FEATURE:
<223> OTHER INFORMATION: Synthetic sequence: Primer M005

<400> SEQUENCE: 1
ctgcccaaat ttgtcatgaa aagcattatg agccg                              35

<210> SEQ ID NO 2
<211> LENGTH: 32
<212> TYPE: DNA
<213> ORGANISM: Artificial sequence
<220> FEATURE:
<223> OTHER INFORMATION: Synthetic sequence: Primer M011

<400> SEQUENCE: 2
gctactgctg cttaggcctg gtttcattaa at                                 32

<210> SEQ ID NO 3
<211> LENGTH: 22
<212> TYPE: DNA
<213> ORGANISM: Artificial sequence
<220> FEATURE:
<223> OTHER INFORMATION: Synthetic sequence: Primer M012

<400> SEQUENCE: 3
ggattttggt tatgagatta tc                                            22

<210> SEQ ID NO 4
<211> LENGTH: 25
<212> TYPE: DNA
<213> ORGANISM: Artificial sequence
<220> FEATURE:
<223> OTHER INFORMATION: Synthetic sequence: Primer M013

<400> SEQUENCE: 4
gggttattgt cttatgagcg gatac                                         25

<210> SEQ ID NO 5
<211> LENGTH: 36
<212> TYPE: DNA
<213> ORGANISM: Artificial sequence
<220> FEATURE:
<223> OTHER INFORMATION: Synthetic sequence: Primer ApaI-LC (C5-1).1c
```

```
<400> SEQUENCE: 5
tgtcgggccc atggttttca cacctcagat acttgg                              36

<210> SEQ ID NO 6
<211> LENGTH: 26
<212> TYPE: DNA
<213> ORGANISM: Artificial sequence
<220> FEATURE:
<223> OTHER INFORMATION: Synthetic sequence: Primer LC(C5-1) - StuI.r

<400> SEQUENCE: 6
cctctaacac tcattcctgt tgaagc                                         26

<210> SEQ ID NO 7
<211> LENGTH: 44
<212> TYPE: DNA
<213> ORGANISM: Artificial sequence
<220> FEATURE:
<223> OTHER INFORMATION: Synthetic sequence: Primer LC (C5-1) - SEKDEL -
      StuI.r

<400> SEQUENCE: 7
cctctaaagt tcatccttct cagaacactc attcctgttg aagc                     44

<210> SEQ ID NO 8
<211> LENGTH: 32
<212> TYPE: DNA
<213> ORGANISM: Artificial sequence
<220> FEATURE:
<223> OTHER INFORMATION: Synthetic sequence: Primer ApaI - HC (C5-1) -
      1c

<400> SEQUENCE: 8
agtcgggccc atggcttggg tgtggacctt gc                                  32

<210> SEQ ID NO 9
<211> LENGTH: 23
<212> TYPE: DNA
<213> ORGANISM: Artificial sequence
<220> FEATURE:
<223> OTHER INFORMATION: Synthetic sequence: Primer HC (C5-1) - StuI.r

<400> SEQUENCE: 9
ccttcattta ccaggagagt ggg                                            23

<210> SEQ ID NO 10
<211> LENGTH: 41
<212> TYPE: DNA
<213> ORGANISM: Artificial sequence
<220> FEATURE:
<223> OTHER INFORMATION: Synthetic sequence: Primer HC (C5-1) - SEKDEL -
      StuI.r

<400> SEQUENCE: 10
ccttcaaagt tcatccttct cagatttacc aggagagtgg g                        41

<210> SEQ ID NO 11
<211> LENGTH: 21
<212> TYPE: DNA
<213> ORGANISM: Artificial sequence
<220> FEATURE:
<223> OTHER INFORMATION: Synthetic sequence: Primer 820-2745.c

<400> SEQUENCE: 11
gtaacgccag ggttttccca g                                              21
```

```
<210> SEQ ID NO 12
<211> LENGTH: 49
<212> TYPE: DNA
<213> ORGANISM: Artificial sequence
<220> FEATURE:
<223> OTHER INFORMATION: Synthetic sequence: Primer 35S/RCMV 5prime.r

<400> SEQUENCE: 12
caaaatttta tataaaaatt ttaatacctc tccaaatgaa atgaagaag                49

<210> SEQ ID NO 13
<211> LENGTH: 26
<212> TYPE: DNA
<213> ORGANISM: Artificial sequence
<220> FEATURE:
<223> OTHER INFORMATION: Synthetic sequence: Primer RCMV 5prime.1c

<400> SEQUENCE: 13
tattaaaatt tttatataaa attttg                                         26

<210> SEQ ID NO 14
<211> LENGTH: 54
<212> TYPE: DNA
<213> ORGANISM: Artificial sequence
<220> FEATURE:
<223> OTHER INFORMATION: Synthetic sequence: Primer RCMV 5prime/C5-1
      LC.r

<400> SEQUENCE: 14
caagtatctg aggtgtgaaa accatgggcc ctttcccaag atattctagc ccag           54

<210> SEQ ID NO 15
<211> LENGTH: 25
<212> TYPE: DNA
<213> ORGANISM: Artificial sequence
<220> FEATURE:
<223> OTHER INFORMATION: Synthetic sequence: Primer C5-1 LC.1c

<400> SEQUENCE: 15
atggttttca cacctcagat acttg                                          25

<210> SEQ ID NO 16
<211> LENGTH: 26
<212> TYPE: DNA
<213> ORGANISM: Artificial sequence
<220> FEATURE:
<223> OTHER INFORMATION: Synthetic sequence: Primer C5-1 LC/StuI.r

<400> SEQUENCE: 16
cctctaacac tcattcctgt tgaagc                                         26

<210> SEQ ID NO 17
<211> LENGTH: 53
<212> TYPE: DNA
<213> ORGANISM: Artificial sequence
<220> FEATURE:
<223> OTHER INFORMATION: Synthetic sequence: Primer C5-1 LC/RCMV3prime.r

<400> SEQUENCE: 17
ctataccatg caacatgaga ccaggcctct aacactcatt cctgttgaag ctc            53

<210> SEQ ID NO 18
<211> LENGTH: 22
<212> TYPE: DNA
<213> ORGANISM: Artificial sequence
<220> FEATURE:
<223> OTHER INFORMATION: Synthetic sequence: Primer RCMV3prime.c
```

<400> SEQUENCE: 18
ggtctcatgt tgcatggtat ag 22

<210> SEQ ID NO 19
<211> LENGTH: 58
<212> TYPE: DNA
<213> ORGANISM: Artificial sequence
<220> FEATURE:
<223> OTHER INFORMATION: Synthetic sequence: Primer RCMV3prime/polyA/
EcoRI.r

<400> SEQUENCE: 19
agaagaattc tttttttttt tttttttaa taaacataac tttaaavcaa taccacaa 58

<210> SEQ ID NO 20
<211> LENGTH: 23
<212> TYPE: DNA
<213> ORGANISM: Artificial sequence
<220> FEATURE:
<223> OTHER INFORMATION: Synthetic sequence: Primer HC (C5-1) - StuI.r

<400> SEQUENCE: 20
ccttcattta ccaggagagt ggg 23

<210> SEQ ID NO 21
<211> LENGTH: 5889
<212> TYPE: DNA
<213> ORGANISM: Cowpea mosaic virus

<400> SEQUENCE: 21
tattaaaatc aatacaggtt ttgataaaag cgaacgtgga gaaatccaaa cctttctttc 60
tttcctcaat ctcttcaatt gcgaacgaaa tccaagcttt ggttttgctg aaacaaatac 120
acaacgtata ctgaatttgg caaatttctc tctctctctc tgtcattttc tttcttctgt 180
cgggactttc ttagtcttga cccaacatgg gtctcccaga atatgaggcc gatagtgagg 240
ctttattaag tcaactcact atcgaattca cacccggcat gacagtttct tcattgttgg 300
cacaagtcac cactaatgac tttcacagtg ccattgagtt ttttgctgca gaaaaagcag 360
tagacattga gggcgttcat tacaatgcgt atatgcaaca aattaggaaa aaccctagtt 420
tattacgcat ttccgtggta gcttatgctt tccacgtttc agacatggta gctgagacca 480
tgtcttatga tgtttatgaa tttctgtata aacattatgc ccttttcatc tctaatctgg 540
tgaccagaac actcagattt aaagagcttt tgctgttctg taagcagcaa tttctggaga 600
aaatgcaagc ttcaatagtc tgggctccgg aacttgagca atatcttcaa gttgaagggg 660
atgctgtggc tcaaggagtt tcacaactgt tatacaagat ggtcacttgg gtgcccactt 720
ttgtcagagg agcagtagac tggagcgttg atgcgatttt ggtcagtttc aggaaacatt 780
ttgaaaagat ggttcaggag tatgtgccca tggctcatcg cgtttgcagt tggctgagcc 840
aactatggga taagatcgtg caatggatct cacaagcaag tgagaccatg ggttggtttc 900
tagatggttg tcgggatttg atgacttggg gaattgccac tctcgcaaca tgtagtgctc 960
tctccctggt tgagaagctg ttagtcgcaa tgggttttct ggttgagcct ttcggcttga 1020
gtggaatctt cttgcggacg ggagttgttg cggcagcttg ttataactat gggactaatt 1080
ctaagggttt tgccgagatg atggctttgt tgtcattggc ggctaactgt gtctctacag 1140
ttatagttgg tggctttttc cctggtgaaa aggacaatgc acagagtagt cctgttatcc 1200
tcttagaagg attggctggg cagatgcaaa acttttgtga gactacactt gtcagtgttg 1260

-continued

```
ggaaaacatg cactgccgtc aatgctatct caacatgttg tgggaatctg aaagcactgg    1320
ccggaaggat cttgggcatg ctcagagatt ttatctggaa gactttgggc tttgagacca    1380
gatttctagc agatgcatct ttgcttttg gcgaggatgt tgatggatgg ctcaaagcaa     1440
tcagtgatct gcgagatcaa tttattgcca aatcatactg ttcgcaggat gagatgatgc    1500
agattttggt gttgcttgaa aagggaaggc agatgcggaa aagtggtctt tctaaaggag    1560
gcatttctcc tgctatcatt aatctgattc tcaaagggat taatgatctt gaacaattga    1620
accgcagctg ttcagtgcaa ggagtaagag gagttaggaa aatgccattt accattttct    1680
tccaaggaaa gtcacgcact ggtaagagtt tgctgatgag tcaggttaca aaggattttc    1740
aggatcacta tggattgggt ggagaaactg tgtacagtag aaatccttgt gatcaatatt    1800
ggagtggata tcgcggcaa ccttttgtgc tgatggatga ttttgccgcc gttgttactg      1860
agccgtctgc tgaggctcag atgatcaatc tgatttctag tgctccatat ccttttgaata    1920 tggctggact tgaagaaaaa ggaatttgtt ttgattctca atttgttttt gtttccacca    1980
acttcttgga agtatctcct gaagccaaag ttagggacga tgaggctttc aagaacagga    2040
gacatgtgat tgttcaggtt tcaaatgatc ctgccaaagc atatgatgct gcaaattttg    2100
ctagcaacca aatttacacc attttggcat ggaaggatgg tcgatacaac accgtgtgcg    2160
ttattgagga ctatgatgag ctggtggcat atttgttgac taggagtcaa cagcatgctg    2220
aagagcagga gaagaatctt gctaacatga tgaagagtgc tacatttgaa agtcatttca    2280
aaagtttagt tgaagtcctt gagctcggtt ctatgatatc tgctggtttt gatatcattc    2340
ggccagaaaa acttcctagt gaagctaagg agaagagagt cctttacagt attccctaca    2400
atggggagta ttgtaatgca ctcattgatg acaattacaa tgttacttgc tggtttggtg     2460
agtgtgttgg taatcctgag cagctctcta agtacagtga aaagatgctt ttgggtgctt    2520
atgaatttct tctgtgttct gagagcttga atgttgtaat tcaggcacat ttgaaggaaa    2580
tggtttgccc tcaccattat gacaaggagc tcaattttat tggcaagata ggagagacct    2640
actatcacaa tcagatggtt tcaaatatcg gctctatgca gaaatggcat cgtgccattc    2700
tgtttggaat tgggggttctc ttgggaaagg aaaaagagaa gacatggtac caagttcagg    2760
ttgccaatgt taaacaagct cttttacgaca tgtacactaa ggagattcgt gattggccca    2820
tgccgatcaa agtcacctgt ggaattgtct tggcagctat tggggggtagt gccttttgga    2880 aagtgtttca caactagtg ggaagcggaa atggtccagt attgatgggt gtggctgctg      2940
gagcattcag tgctgagcct caaagtagaa agcccaatag gtttgatatg cagcaataca    3000
ggtacaacaa tgttcctctc aagagaagag tttgggcaga cgcacaaatg tctttggatc    3060
agagtagtgt tgctatcatg tctaagtgta gggctaatct ggttttttgga ggcactaatt    3120 tgcaaatagt catggtacca ggaagacgct ttttggcatg caaacatttc ttcacccaca    3180
taaagaccaa attgcgtgtg gaaatagtta tggatggaag aaggtactat catcaatttg    3240
atcctgcaaa tatttatgat atacctgatt ctgagttggt cttgtactcc catcctagct    3300
tggaagacgt ttcccattct tgctgggatc tgttctgttg ggacccagac aaagaattgc    3360
cttcagtatt tggagcggat ttcttgagtt gtaaatacaa caagtttggg ggttttatg      3420 aggcgcaata tgctgatatc aaagtgcgca caaagaaaga atgccttacc atacagagtg    3480
gtaattatgt gaacaaggtg tctcgctatc ttgagtatga agctcctact atccctgagg    3540
attgtggatc tcttgtgata gcacacattg gtgggaagca caagattgtg ggtgttcatg    3600
ttgctggtat tcaaggtaag ataggatgtg cttccttatt gccaccattg gagccaatag    3660
```

```
cacaagcgca aggtgctgag gaatactttg attttcttcc agctgaagag aatgtatctt    3720
ctggagtggc tatggtagca ggactcaaac aaggagttta cataccatta cccacaaaaa    3780
cagcgctagt ggagaccccc tccgagtggc atttggacac accatgtgac aaagttccta    3840
gcatttagt tcccacggat ccccgaattc ctgcgcaaca tgaaggatat gatcctgcta     3900
agagtggggt ttccaagtat tcccagccta tgtctgctct ggaccctgag ttacttggcg    3960
aggtggctaa tgatgttctc gagctatggc atgactgcgc tgtagattgg gacgattttg    4020
gtgaagtgtc tctggaggaa gctttgaatg gatgtgaagg agtggaatat atggaaagga    4080
ttccattagc aacttctgag ggcttccgc acattctttc tagaaatggg aaagaaaagg     4140
ggaaaagacg gtttgttcag ggagatgatt gtgttgtctc actaattcca ggaactactg    4200
tagccaaagc ttatgaggag ttggaagcaa gtgcacacag atttgttccc gctcttgttg    4260
ggattgaatg tccaaaagat gagaagttgc ctatgagaaa ggttttttgat aagcctaaga   4320
ccaggtgttt taccatttg ccaatggaat ataatttggt cgttcgtagg aagtttctga     4380
attttgtgcg ctttatcatg gccaatcgtc acagactcag ttgtcaagtg ggtattaatc    4440
catattcaat ggaatggagt cgcttagcag caaggatgaa agagaaaggc aatgatgtct    4500
tgtgttgtga ttatagctca ttcgatggct tgctttctaa gcaagtgatg gatgtcattg    4560
ctagcatgat caatgaactt tgtggtggag aggatcaact caaaaatgca aggcgaaact    4620
tgttaatggc gtgttgctct aggttggcta tttgcaagaa tacagtatgg agagttgagt    4680
gtggtattcc ttcagggttt ccaatgacag tgattgtgaa tagcattttt aatgagattc    4740
tcattcgcta tcattacaag aaactcatgc gcgaacaaca agctcctgaa ctgatggtac    4800
agagttttga taaactcata gggctggtga cttatggtga tgataatctg atttcagtga    4860
atgctgttgt gacaccctat tttgatggga agaaattgaa gcaatctttg gctcagggtg    4920
gtgtgactat cactgatggt aaggacaaaa caagtttgga acttcctttt cgcagattgg    4980
aagaatgtga ttttctcaag agaacttttg ttcagaggag cagtaccatc tgggacgctc    5040
cagaggataa ggcaagtttg tggtcgcagc ttcattatgt taattgcaac aattgtgaga    5100
aagaagttgc ttatttgact aatgttgtta atgttcttcg tgaactttat atgcatagtc    5160
ctcgggaagc cacagaattt aggaggaagg tcttaaagaa ggtcagttgg atcactagtg    5220
gagatttgcc tactttggca caattgcaag agttctatga gtaccagcgg cagcaaggtg    5280
gggcagacaa caatgacact tgtgacttgt taacaagtgt agacttgcta ggtcctcctt    5340
tgtcttttga aaagaagcg atgcacggat gcaaagtgtc tgaagaaatc gtcaccaaga    5400
atttggcata ttacgatttc aaaaggaaag gtgaggatga agtggtattt ctgttcaata    5460
cgctctatcc tcagagttca ttgcctgatg ggtgtcactc tgtgacctgg tctcaggta    5520
gtggaagggg aggtttgccc acacaaagtt ggatgagcta taatataagc aggaaagatt    5580
ctaatatcaa caagattatt agaactgctg tttcttcgaa gaaacgagtg atattctgtg    5640
ctcgtgataa tatggttcct gttaacattg tagctttgct ctgtgctgtt agaaacaagc    5700
tgatgcccac tgctgtatct aatgctacac ttgtcaaggt gatggaaaat gccaaagctt    5760
tcaagttttt accagaagag ttcaattcg cttttttctga tgtttaggta aataatgctt    5820
atgttttgt ttgctcctgt ttagcaggtc gttccttcag caagaacaac aaaaatatgt     5880
gtttttatt                                                            5889
```

<210> SEQ ID NO 22
<211> LENGTH: 3481
<212> TYPE: DNA

<213> ORGANISM: Cowpea mosaic virus

<400> SEQUENCE: 22

```
tattaaaatc ttaataggtt ttgataaaag cgaacgtggg gaaacccgaa ccaaaccttc      60
ttctaaattc tctctcatct ctcttaaagc aaacttctct cttgtctttc ttgcatgagc     120
gatcttcaac gttgtcagat cgtgcttcgg caccagtaca atgttttctt tcactgaagc     180
gaaatcaaag atctctttgt ggacacgtag tgcggcgcca ttaaataacg tgtacttgtc     240
ctattcttgt cggtgtggtc ttgggaaaag aaagcttgct ggaggctgct gttcagcccc     300
atacattact tgttacgatt ctgctgactt tcggcgggtg caatatctct acttctgctt     360
gacgaggtat tgttgcctgt acttcttttct tcttcttctt gctgattggt tctataagaa     420
atctagtatt ttcttttgaaa cagagttttc ccgtggtttt cgaacttgga gaaagattgt     480
taagcttctg tatattctgc ccaaatttga atggaaagc attatgagcc gtggtattcc      540
ttcaggaatt ttggaggaaa aagctattca gttcaaacgt gccaaagaag ggaataaacc     600
cttgaaggat gagattccca agcctgagga tatgtatgtg tctcacactt ctaaatggaa     660
tgtgctcaga aaaatgagcc aaaagactgt ggatctttcc aaagcagctg ctgggatggg     720
attcatcaat aagcatatgc ttacgggcaa catcttggca caaccaacaa cagtcttgga     780
tattcccgtc acaaaggata aaacacttgc gatggccagt gattttattc gtaaggagaa     840
tctcaagact tctgccattc acattggagc aattgagatt attatccaga gctttgcttc     900
ccctgaaagt gatttgatgg gaggcttttt gcttgtggat tctttacaca ctgatacagc     960
taatgctatt cgtagcattt ttgttgctcc aatgcgggga ggaagaccag tcagagtggt    1020
gaccttccca aatacactgg cacctgtatc atgtgatctg aacaatagat tcaagctcat    1080
ttgctcattg ccaaactgtg atattgtcca gggtagccaa gtagcagaag tgagtgtaaa    1140
tgttgcagga tgtgctactt ccatagagaa atctcacacc ccttcccaat tgtatacaga    1200
ggaatttgaa aaggagggtg ctgttgttgt agaatactta ggcagacaga cctattgtgc    1260
tcagcctagc aatttaccca cagaagaaaa acttcggtcc cttaagtttg actttcatgt    1320
tgaacaacca agtgtcctga gttatccaa ttcctgcaat gcgcactttg tcaagggaga    1380
aagtttgaaa tactctattt ctggcaaaga agcagaaaac catgcagttc atgctactgt    1440
ggtctctcga gaaggggctt ctgcggcacc caagcaatat gatcctattt gggacgggt    1500
gctggatcca cgaaatggga atgtggcttt tccacaaatg gagcaaaaact tgtttgccct    1560
ttctttggat gatacaagct cagttcgtgg ttctttgctt gacacaaaat tcgcacaaac    1620
tcgagttttg ttgtccaagg ctatggctgg tggtgatgtg ttattggatg agtatctcta    1680
tgatgtggtc aatggacaag attttagagc tactgtcgct tttttgcgca cccatgttat    1740
aacaggcaaa ataaaggtga cagctaccac caacatttct gacaactcgg gttgttgttt    1800
gatgttggcc ataaatagtg gtgtgagggg taagtatagt actgatgttt atactatctg    1860
ctctcaagac tccatgacgt ggaacccagg gtgcaaaaag aacttctcgt tcacatttaa    1920
tccaaaccct tgtggggatt cttggtctgc tgagatgata agtcgaagca gagttaggat    1980
gacagttatt tgtgtttcgg gatggacctt atctcctacc acagatgtga ttgccaagct    2040
agactggtca attgtcaatg agaaatgtga gcccaccatt taccacttgg ctgattgtca    2100
gaattggtta ccccttaatc gttggatggg aaaaattgact ttttcccagg gtgtgacaag    2160
tgaggttcga aggatgcctc ttctatagg aggcggtgct ggtgcgactc aagctttctt    2220
ggccaatatg cccaattcat ggatatcaat gtggagatat tttagaggtg aacttcactt    2280
```

-continued

```
tgaagttact aaaatgagct ctccatatat aaagccact gttacatttc tcatagcttt      2340
tggtaatctt agtgatgcct ttggttttta tgagagtttt cctcatagaa ttgttcaatt      2400
tgctgaggtt gaggaaaaat gtactttggt tttctcccaa caagagtttg tcactgcttg      2460
gtcaacacaa gtaaacccca gaaccacact tgaagcagat ggttgtccct acctatatgc     2520
aattattcat gatagtacaa caggtacaat ctccggagat tttaatcttg gggtcaagct      2580
tgttggcatt aaggattttt gtggtatagg ttctaatccg ggtattgatg gttcccgctt      2640
gcttggagct atagcacaag gacctgtttg tgctgaagcc tcagatgtgt atagcccatg     2700
tatgatagct agcactcctc ctgctccatt ttcagacgtt acagcagtaa cttttgactt     2760
aatcaacggc aaaataactc ctgttggtga tgacaattgg aatacgcaca tttataatcc     2820
tccaattatg aatgtcttgc gtactgctgc ttggaaatct ggaactattc atgttcaact     2880
taatgttagg ggtgctggtg tcaaaagagc agattgggat ggtcaagtct ttgtttacct     2940
gcgccagtcc atgaaccctg aaagttatga tgcgcggaca tttgtgatct cacaacctgg     3000
ttctgccatg ttgaacttct cttttgatat catagggccg aatagcggat ttgaatttgc      3060
cgaaagccca tgggccaatc agaccacctg gtatcttgaa tgtgttgcta ccaatcccag      3120
acaaatacag caatttgagg tcaacatgcg cttcgatcct aatttcaggg ttgccggcaa      3180
tatcctgatg ccccccatttc cactgtcaac ggaaactcca ccgttattaa agtttaggtt     3240
tcgggatatt gaacgctcca agcgtagtgt tatggttgga cacactgcta ctgctgctta     3300
actctggttt cattaaattt tctttagttt gaatttactg ttatttggtg tgcatttcta     3360
tgtttggtga gcggttttct gtgctcagag tgtgtttatt ttatgtaatt taatttcttt     3420
gtgagctcct gtttagcagg tcgtcccttc agcaaggaca caaaaagatt ttaattttat     3480
t                                                                    3481
```

<210> SEQ ID NO 23
<211> LENGTH: 6033
<212> TYPE: DNA
<213> ORGANISM: Red clover mottle virus

<400> SEQUENCE: 23

```
tattaaaatt tttatgcaaa attttgataa ccgcaaacgt ggagaaatcc aaaactcact      60
tacaaactct cttttctgct tgagacaatt ttaattgcaa ttttctcatt cttgaataca     120
aacaaatttg tatttgcttg aagtctggaa catcgagcga tccttggtac caatactacc     180
ttggggagtg tttcacactt ttcttttctt ctcctaattt ctctcaattt caatattgtg     240
ttagtgcgca tttacagcat cattaaatca tgtatatgtt aacttttgag ccgggtctttt     300 gtgtggcagg tatcatacgc caagtgcgta gtaatccgtt catgcatgtt gtgcaagcct     360
atgcacgcac aacagaaact taccgtgaag atattgaaat gacaaaatcc atgttgaagc      420
ttaaagctga tgagccttta ctggttatgt caattgttgc agcagctatg gattttcaga      480
caatggttat ggcaccaata gaaatggaag cttctgaatt tctttatggc ttctatgcag     540
aaagaatgtc atacattgtg acaaatagag gtatgtcaga gctccatgag tatattcagt     600
tgcaatgcca aagacatcta cttgtcaagg tggagattga tggacagtac ttagtccagg      660
agcatgagta tgaggcacaa ggatttaaca tcaagagggt taaagaatta atcacagatg     720
ttgcaacttg ggtcccaaag aaagtcaagg gaatgatagg ttggtctgta gacgcagttc     780
tagactcttt tcaggaatac ttttataaag ttattactga aagaattcca atggccatga     840
aggtgtgttc atgggtggcc acagtttggg accaaatcaa gacatggata gaagatgcta     900
```

```
tgactgccat gtctagtttt ctccagggtt gtaacgaatt actaacatgg ggtttagcta   960
ctctggcagc atgctgtgct ctaaatgttt tggagcgaat tctaatattc atggaatttt  1020
tagatgagag tattgacata gcaggcattt tccttcggac tggagtggtt gcagcagctt  1080
gttaccattt tagttccacg gcaaaaggat tcacagagat gatgtctgtc ctttcagtcg  1140
caacaacagc cgtagctgct gtagtctgtg caaattactt tggaggtagt aaaaccaaaa  1200
aggtaaatgc gcaaggtaat ccagtagatt tattggaaag aatagcagct ggtctgtcta  1260
gtatatccca agattcattg gtatccctgg gtaagtcctg tagtgctata aactctatag  1320
ctacaagcta tggacatctg cgtaacttcg caggtagagt tttaactatg cttagggatt  1380
ttgcctggaa aattttgggg cttgaaactc gtttccttgc agatgctgct ttagtgttcg  1440
gagaagacgt tgatggttgg ttgcagagaa ttagtgcttt gagagaggcc tatgtttcca  1500
aagcatattc ctcacaggat gaggtatttg agatgaatgt cctgttggaa agaggctata  1560
aaatgagaca tctaatggca acaggctcta gagtttcccc tgcaattggt aacatgctca  1620
tgcagggttt ggcagatctt gagagattgc acaggaatgc tgcagtacag ggcgtgaaag  1680
gtgttaggaa ataccttttt acagtctttg ctcatggtaa ctccagatgt ggaaagtctc  1740
tacttattgg caaactcata agcgatttcc aagaacataa gggccttggt gaggacacgg  1800
tgtactctcg gaacaccact gaaacgcact ggagcggtta tagaagacaa cctatagtgg  1860
tgattgatga ctttgcagca gttgaatctg atatttctgc tgaggcgcaa ctgataaatc  1920
ttgtttctag cacaccctat tcagttgtta tggctgccat agaggagaag ggaatgactt  1980
ttgactctca gttcatattt gcatctacca attttctgga agttagccct aatggaaaga  2040
taagatgtga tgatgctttc agaaatagga gacatgtgct aattgatgtg aagcttaaac  2100
ctgaagtaga gtaccagagt gatgatttca cagcaaatca gagctacaac attttagagc  2160
acagtcatgg aagatacaat gttgtggcaa cttttgataa ctatgaggag ctgttggcat  2220
actgtttgac caaacatgaa caacatgaag ccgagcagga agccaatctt gcaaagctgc  2280
gtaggactaa taaatttgag tcccatttca aaaaatttga acaagtgcta caattgtcca  2340
catatttcag ctcttccata gagagaatca agagggaagc tctggcgacc acagatgggg  2400
cggatgatta tcatttactg tatgtggtac ccagaaatgg ttcctatttg cacgttgcag  2460
ctaataagga ttttcagatc caacagtggt acggacctgt ggaagaagtc gcagaggagg  2520
atattttgag ggcatcagaa aggatgctgc ttggagccta tgagtttta ctactttcca  2580
cagaactcaa tgtggtggtc aaaaatcatc taccagagtt gatatgtact gataattatg  2640
atcacaacct ggaattttgt ggtgttgttg gagaccctgt atatcaccaa caactactca  2700
agaacattag agccctcaaa ccatggcata gagccgtgct ctttggtatt ggcactctta  2760
tgggagccaa aaatccaaca ccatggtata aaggatgtg ggaaggaatc aaggatgttc  2820
tgtacaaagc ctactctact gaaatatccc aatggcctgt acccttgaaa atcacatgtg  2880
gaattgtgtt ggttggcatt gtcggggcag gattttggaa aacagtttca gttctgacaa  2940
atgcgggcaa tggggcagga ctggtaggag cagcagtgaa ttctttctca gttgtttcta  3000
cagctgaagc acagagcagg aagccaaaca gatttgaagt gcaacagtat aggtacaaga  3060
acgtgcctct tactagaagg tcatgggta atgcccagat gtcactcgac caaagcactg  3120
tgtcaatatt aaacaaatgt catgccaagt ttatcatagc ttcacaacat gctcagatag  3180
tgctagtgcc aggcagaagg tttattggtt actctcactt tttctgcaat cttaaacatc  3240
ctttgatggt acagatagag actgctgata gaacttactt tcacaggtac caacccgaaa  3300
```

-continued

```
acatggagta tattgaagat tctgagctct gtgtttatca tagttcgtgc ctagaggaca   3360
tctctcatag ctgctgggat cttttctgct gggatcctga caaggaactg ccaaagaaat   3420
tttcagcaga ctttgtttcc tgcaagtaca ataccctgga caaaagtgtt gaaccaacat   3480
gggcaaacgt ggatgctgag gtgattaaag aagattttac catttgtgat ggtgaatatc   3540
gcaacacagt gagtacgagc atcaggtacg aagcgccaac ggttatgtca gattgtggtt   3600
ccatgatcat caccaatgtg ggtggaaaaa ccaaaatagt aggcattcat gttgcgggaa   3660
gggacaataa gataggcatg gccagtttgc tgcctccact attgccctgt gcacaggctc   3720
aaggtgcaga aaagtatttt aattttatc caatagagta tgatgcagct gaaggtatag    3780
ctagggtagg agagttaaaa cccaaacttt acattccctt gccaaagaaa acctcattgg   3840
ttaaaacacc tgaagaatgg cacctaggaa caccctgtga taaagtgcct tcaattctgg   3900
tgaaagggga tcccaggcta gcggacactg tgcatgcaga ttatgaccca tgtctctcgg   3960
gtctcactaa gtattccaca ccaatgtctc cgttagattc agtgctgctt ggggaaactt   4020
gccaagaaat actggatgag tggtttgatt gtttgccaga aggatttgag cttgggagg    4080 tgactattaa tgaggcactt aatggagttg acggtgtgga ttacatggat cgcatacctt   4140
tggctacttc agaaggcttc cctcatgtca tgtcacgaga acaaggtgag aaagggaaac   4200
aaagatttgt gcaaggagat ggacatattg tctctttaat tccaggtact agtgttcatg   4260
aagcatatga acattgtct cggacaatag caacagaagt gcctacccttt gttggaatag    4320 agtgtcctaa agatgagaag ttgcctttca gaaaggtgtt cacaaagcca aaaactagga   4380
atttcactat tcttcccatg gaatacaaca tcttggttag gcaatatttt cttaattttg   4440
tgcgtttcat catgaagaag agagatgttt tgccttgcca ggtaggtatc aatcctata    4500 gcatggaatg gtccatagtt gcatcgagat tgaagagtca aggcaacgat attctgtgtt   4560
gcgactactc ttcatttgat ggtttgctct ctaaacagat tatggaaatg atggctgata   4620
tgatcaatag attctgtggg ggcggcactc tcatctgtgc aaagagaaag aacttactga   4680
tggcttgttg ttctcgccta gccatctcca gggacagtgt atggaggatt gagtgtggaa   4740
taccatcagg tttttccctttg acagtcatct gcaatagcat cttcaatgaa attctggtca   4800
ggtatcacta caaactactg ctgcaagagc ataatgctcc caacatgtat gttcaaagct   4860
ttaaaaacct gattagcatg gtgacctatg gtgatgataa tctgatttct gtgaatgctg   4920
tggtgaagcc ttactttgat ggaacaaagc tcaagcaagc aatggctagg aatggcataa   4980
tcataacaga tggtaaggac aaaacaagtg ccacacttga atttcgacgc ttggaagatt   5040 gtgatttct caaaagaggt tttcttaaga gatcttcagt actctgggac gcacctgagg   5100
agaaagccag tttatgggca caattgcatt atgtaaatgt caacaattgt gaaatgcaag   5160
tggcctatat gacaaattta gtgaatgtgc tgagggaatt gtacatgcat gatcctactg   5220
aaatggtgga gtttcgtaga ttggcattga agtccattcc ttggttgaac accacagatc   5280
taccaacact ataccaggtt aaagagtttt atgcagagca aagattgagg aatatccctg   5340
accacaatga cagtcttgac atgctgacta gtgttgatct actaggacca gcaatcctgg   5400
gggagggggt tccacaagaa gccctagtgc taagtgaact gctagaggtt agagatctga   5460
gatatcacac tgttccagat aatgataatg caaggaagt gtggattcta ttcaacacca   5520
tgtatcctca gaagctcttg ccatcaaatt gccacagttt cacttggaat gcggacagg    5580 gtagaggagg tttaccaaca caacactggt tggctacgaa tgtgacaaga acagattcca   5640
agctcaacaa gttaatcaga acagctgttg cagccaataa gaagattgtg ttagcaacca   5700
```

```
aggacaacat attgcctatc aatgtcattg cagttctgct agcagccaga aacaaggtga    5760
tgccttcttt ggctacaaat gcattgttaa cttacgtcat aggtgcagcc aagaaactta    5820
attttttgac ctctgagtgt caattcgctt tctttaatgt ctgatgtaat ttggaaattc    5880
gtgttttctg tgtgtcgtga gttttcgttt gttatttctt ttgggtgttt tcttccaata    5940
gaataaatgg aatttattcc attagtataa tatcttcctt tatcttattt taatatagta    6000
ctgttgtggt atgtgataaa gtttgtgttt att                                 6033

<210> SEQ ID NO 24
<211> LENGTH: 3543
<212> TYPE: DNA
<213> ORGANISM: Red clover mottle virus

<400> SEQUENCE: 24
tattaaaatt tttatataaa attttgataa ccgcaaacgt ggggaaaccc gaaacctttc      60
ttttcttttc tttcaaagcg aacgagtatt ccagctttca agcgaaccac ttttcgttga     120
caccttactt ttagtaatcg tgttgattta ttgaagaata gcgtgtggag cgatccttgg     180
tgttaattca ccctgaggag cacgttatat cttttcttcc cttctttctc ttggattaca     240
aatacgcaag cattcaattg tcagcaccct tcatagctct attaatatat atgttgggaa     300
ttagcaattt gtgcagatac taccaaggtc aaagacgagt gtgtgccaat aagttttacc     360
agaagtatgt taaccactca gatttgtact ttttcgatct ctgggaaatt tcggctaaca     420
atctttggat taagttagct tttgtactgt tactttgtct ctttgaaata atttctgggc     480
tagaatatct tgggaaaatg gcacaagaaa ttttgaaaca aggtattcca gcaaatgtgc     540
tacaagaaaa agccaacctt tcaagaaagg ctagtgcaaa caataagatt aaggatgaaa     600
tgccaaatgc actgtctctt taccaaaacc actccttctt ccagaaactc aaacatctag     660
cagacaagaa gaatttggat atcactagtt tacctggagg tagggaagtg aatacaaac      720 atcttgatgc aggccattta ttggcggata caaatgtggt tatagatgtt ccacttgttc     780
cacaacttgc cgctaggaca ccaactgatt acaattttgg aactagcaga gacaagagtg     840
ccactgcttt gcatgtcgga gcaatagagg ttgtaattca gagttatgcc tcttctgagt     900
gtgatttaat ggcaggcatg atgctggttg acactttcca ctcgcgccca gagaatgcca     960
tcagatcagt atacatagtg ccaattcgag ggggtatgtt tatgcgagct ctatgttttc    1020
ctaacacatt ggttcctatg gactctgata taaataatag gttcaaggtg gttttctctc    1080
taccaaacaa tgactttccc cagggtagta aacttggaca tgtttccata aatatggctg    1140
ggtgcactac tagcttgagc aaaacatatg ttccctctcc tctactcaca gaagagttgg    1200
gcagagaagc tgccacagtg attcagtatc ttggaagaga tacgtatgcg atgcagacca    1260
gtaatgtgcc aaccagtgat gaaattagtc gaatggtctt caactttcac atggaaggca    1320
agttgtctat gcataaaaca ggctctctat cctctatact gagtaagagt aaagtttga    1380 ggtacactat tggagggagc aagcccaaaa ataaactagc tgacaaagct cataatgagg    1440
aagctgaaac ctctgatagt aaagggatta ttgatcctaa ggacggtaat gtatttgcaa    1500
atccccagac tgacactgat tgttcaaat taagtttgga tgatacgtcg agtcccaaag    1560
gatcactatt agacacaaga tttgcccaaa agaaagtttt gattccaaaa gcaatggcag    1620 gggggcaga cttactgagt tcaaatcttt atgatgtgct atcgggaagt tcctttagag    1680
cctctctagc attagcaaga actcatgtgg ttgaaggaaa gatcaggtgt atttgcacca    1740
taaacttacc tgagaatact gggtgctgtc tggcaatcac agttaatagc agcaatagag    1800
```

-continued

```
ggcagtttag tacagatata tatacaacag gttctcagga cagaatttta tggaatcctg   1860
cttgttccaa aaattgtgat ttctccttta atccaaatcc ttgtgggact gcatggagct   1920
tggaattctt gcgtcgcact aagtttcact tgagtgtcac atgtgtgtcg ggtggtcag    1980 cccaaccgca gacagacatt gccatgacaa tggattggta tgtgagtaat aagccatgtg   2040
tgccatgtat ttacaatgtt ggaacgcctg acaaaatgt ttgggttaat agatggatgg    2100
gtaaactgtc tttccctcaa ggatctcaaa atcaacttaa acagatgccc ttggccatag   2160
gtggcggtgc tggagcaaaa aatagtattc ttatgaatat gaccaatgct tttctgagtc   2220
tctggcgcta ctttcacggt gatctagttt ttgaggtaca gaaaatgagt tctccttta    2280 taaagtcaac tgtgactttc ttcataggtt ttgggggtct tccttttagt gaaaacttgg   2340
aagattttcc aaataagctg attcaatttg gagaagtgca agaaagagtg gagataacat   2400
ttactaggaa ggaattcctg acggcgtggt ctacccaagt tgacccagct ggacctgtgg   2460
ctggtgatgt tgcccttat ttgtgtgcta tggtacatga ttcaacagcc agtaccataa    2520
caggagattt taacttgggt gtcaccctat tgcgcattga aattttgtg ggcataggca    2580 gaaatcctgg aatacagggg gcccgattgc taggaagcat gcaagcggaa gcccagggtg   2640
gcgtcgtacg cactactgat ggtgtttaca gcacatgctt tagagttaga accccactag   2700
cacttaaaga ttcaggatct tttacctgcg atttgatagg aggggaata accacagatt    2760 caaatacagg atggaatctg accgcattga atactcctgt tgccaacctt ctacgcacag   2820
ctgcttggaa aagaggtact atacatgtgc aagtggcaat gtttggcagt acagtcaaaa   2880
gatcagactg gacttcaact gtgcagctgt tccttaggca atccatgaat accagtagtt   2940
atgatgctcg agtgtgggtg atttcaaaac caggagcagc aatattagaa ttttcttttg   3000
acgtggaggg tcctaacaat ggatttgaaa tgtgggaagc aaattgggcc tctcaaacta   3060
gctggttcct agagttcttg atctccaatg tgactcaaaa cacattattt gaggttagca   3120
tgaaattgga cagcaacttc tgtgtggcag gaacaactct tatgccgccc ttctctgtga   3180
cagcaagtcc tgattcgcgc ccacttctag gcgtgaaaac gtccacacct gctaagaagt   3240
atgttggtgg tagtctccaa gctggccctt caccagattg aggtctcatg ttgcatggta   3300
tagttgcata tttattttat gttcattttc tttcttgctt gagtgtgtta tttcaatagc   3360
tcctgtttag caggtcgaac cttcagcaag ttcacaaaaa gattttcctt ttgtgtgttt   3420
cttttcgtgt gatggcttac ttttgtgatt actttgtatg ttttttacaaa tttgtgataa   3480 tattagcttt aaagttattt taatatagta ctattgtggt attgctttaa agttatgttt   3540
att                                                                  3543
```

<210> SEQ ID NO 25
<211> LENGTH: 5995
<212> TYPE: DNA
<213> ORGANISM: Bean pod mottle virus

<400> SEQUENCE: 25

```
tattaaaatt ttcataagat ttgaaatttt gataaaccgc gatcataggt tgccgcacct    60
taaaaccgga aacaaaagca atcgttactt gatttcaaag acttctcaat ttctctctac   120
atttcttgta tacggctttc aaagtgaaag aaaatcactc tctgtgctgg tcgcagcatt   180
cgtgaatcat tttctttctg ctctcagttc attcgctgaa cactctccta tttgatatag   240
gacttcgtgt cagatttgaa cttctcttac ctctctttct cggttcttca tttgatttca   300
aatttctctg aaatttaaat ttcttttgac attttgaact ttgtgttggt tccatttgaa   360
```

```
aaacaacatg aagttctatc ctggtcagaa tatttctgaa attgtttacc actttcagag    420
taatgagaca gccaataggt tagatgcata ttttgcttgt ggctgtgagg aggatactga    480
agtcctcgct cgtttgaagc agtgtaatcc tcgtctgctt catctgtcat atgctgcctt    540
ttgtttggaa atgggcagtc attcaataga ggaaatggaa tatgatgatg gggaattaat    600
tttttcctat tttcaaaatt ttttgctttc catcgtttcc aattcttcta aacaaccaa     660 attgagagca tacattcgtt cagcatttgc atatcatttt cagcattttg ttgaatttga    720
tcaatataca aatgattctc tcaatactgt agatacaagt gtatcagccc aagggatagc    780
agacttggct ctctctatgg ttagatggat acccactcag attaaaaaag ttgttaattt    840
tggtgtggga tctgttatag agtcttttc agagcatttt aataagctct tgatgcaata     900
ttgtccaata gtttttcaag ctttcagctg ggttaacaat atttggacaa tggtcaaaga    960
gtggatagaa gaagctgcga agaaatttc atggtttttg caaggatgta aagagctgca    1020
tgcctgggga atgtgtattt tggctagctc ctgtgctcta ggattggttg aaaaatgcct   1080
tatttctttg ggcatgattt ccgaatcttt tgatttggtt ggcttgtttg tccgatctgc   1140
cattgtggga gctttctgtg tttccataaa aactggcaag ttcgtcacga atagtgaatt   1200
gatcacttgt gctaccattg cagtttctac aatagcaact gtaatgtctc aggcttttaa   1260
gccttctgaa gagattaagg gacagttcca agccctttca gttctagaag ggttggcaac   1320
acagctcact tcattttgtg acacgtcctt agttgctatg ggaaaaacct gcacagcttt   1380
taatcaaatt tgcactgctg gcaaaaatgt taaggtgatc gcaggtaggt tgctggaagt   1440
tgtttctaat tttgttagaa aattattagg attggatagt gcttttctca gagatgctgc   1500
actcattttt tctcaagatg tggatggatg gttgcgtaac attagttggt gccaagaaca   1560 gttttgttg aaagcttaca tgtcgcaaga tgatcttatt gtcttacgct ctttagttgt    1620
caaaggtgaa agaatgaggg aacagatgct tgaaggagaa gttaaggtgt ctccaagtgt   1680
ttgcaacctt attgtcaaag gctgtgaaga agcaaataaa ttgatgcgtg agagccgact   1740
tcattgttca aaaacaatta ggaaaattcc ttttgttatt tttgctcacg gtgaatcccg   1800
agttgggaaa tctctgctgg ttgataggct aatcacagat ttctgtgatc atttggaaat   1860
tggagaagat gctgtgtact caaggaatcc atcagatcct ttttggagtg gatatagaag   1920
gcagccaatt gttactattg atgattttgc tgctgttgtt tcggagccat ctgctgaagc   1980
tcaattaatt ccattagttt caagtgctcc ttatccaata aacatggctg gtttggagga   2040
aaagggaatg cactttgatt cccagatcat gatgtgttct tcgaatttct tagagccgtc   2100
tcctgaagct aaaattagag atgatatggc ttttagaaat cgaagacatg tgctgatcac   2160
agttgaactc aaacctgggg ttgaatatga tgagagtgat tttactaaaa atcagcgata   2220
tttgctgaaa acttggtttc attatcatta tgttgtagac caaacttttg agtcttatgc   2280
tgatctgctg gcacattgtt ttaccaagtg ggagagacat gttaaggagc aagagtcaaa   2340
tctgtctcaa attaagggca agaaaagtga aagtggtcat ttctataact ttcaacaact   2400
tatggatttg gctgtttcat ggaatcttaa tgcagatatc atgaaaaaca ggatcaaggc   2460
tgagagaaat gacatggttt atgttttttc tgcagggagg aaggataaaa ttttgcattg   2520 tttttttgaac aaggaaggcg agtgcacggt tcgtcctgat tcaatagatg atcctgaagc   2580
gcaagctttg ctcaaagctt cagagacaat gctcatgaaa gcctatgcct tcctcaaata   2640
caataatgca acaaatttga ttgtcaggac ccatttggca gaactggtga atgaagattt   2700
ttatgatgaa aaattcaatt tcattggaac aattggaaca ccggcttttc atcgccaaat   2760
```

```
agctgcacat ttggaaaaga tgccattgtg gcaaaaagca attttgtgtg gaatgggaca    2820
ttgtttgtct cggaaaagca aagaaacctg gtatactggt atgaaggaga aatttgtgca    2880
gatgatgaaa agcatttatg aaactgaagt cacagattgg ccagtgccat tgaaaatcat    2940
ttctggtact attctagcca ccattttggg aacaactttt tggaagttat tttccttttt    3000
aagggatgct ggtaatggag gtgttttgt tggtaatgtt gcttcagcat ttactacatc     3060
aagtgtgctc gaggcgcaaa gccgaaaacc caacagatat gaggtctctc aatataggta    3120
tcgcaatgtg ccaataaagc gcagagcgtg ggttgagggc caaatgtctt tgatcaatc     3180
agtggtagca attatgtcaa aatgtaaagc cagtatgaga atgggaaaca ctgatgctca    3240
gattttgatg gttccagggc gtagattcat tgcacatggt cattttttca gaatctcac     3300
ccaaaaagtt agagtccaaa ttgttacttc tgagaaaagc tattggcatg tgtatgatcc    3360
tgataaattt caaatgtttg ataacagtga aattggggtg tatacaaatc caactttgga    3420
ggacatccca cattctgctt gggacctttt ctgctgggac agtgagaaaa ctttgccaaa    3480
caattttctct gctgaattgc tttcctgtaa attggacact gttacgggac aatattatcc    3540
cagaatggct ccaataaatt gtcgagtaca tcggcaacca attcacataa ctgaagggaa    3600
ttatgttagg aaacaagatg taagcattga atatgatgcc tgcacaattc ccaatgattg    3660
tggatctctg gtggttgcta aggttggaaa tcacaagcaa attgttggtt ccatgttgc     3720
tggaagcaaa ggaagattgg gctatgcttc attaatacca tatgttgagc ctgtggtaca    3780
agcccaaagt gctgaagtct attttgattt ctttcctgtg aagttgata gtcaagaggg     3840
agtagctcat attggtgaac tcaaatctgg agtttatgta ccactgccca caaaaactaa    3900
tcttgtggaa actcccaaag aatggcagtt ggatttgcct tgtgataaga ttccaagtgt    3960
gttaaccact actgatgaga gattggttgg cacagagcat gaagatatga cccattcttg    4020
gtggtattca aaatatgcaa ctcccatgat gcctcttgat gaggagattc tttccaaagt    4080
tgcacaagac atggttgaag agtggtttga ttgtgttgat gaggaggata catttgaaga    4140
agtttctttg agtgctgcac tcaatggtgt tgaaggtttg gattacatgg aacgcattcc    4200
tcttgccact tcagagggtt ttcctcatgt tctgtccagg aaaaatggtg aaaaaggcaa    4260
gagaagattt gtcactggag atggtgaaga aatgtcacta attcctggta ccagtgttga    4320
agaagcgtac aataaattga ctgttgaatt agaaaagtgt gttccaacat ggttggtat     4380
agaatgtcct aaagatgaaa aacttcctcg tcgcaaaatt tttgataaac ccaagacgcg    4440
ctgcttcacc atacttccta tggaatttaa tttagtggtg cgtcaaaagt tcttgaattt    4500
tgtgcgattc attatgaaga aaagggacaa attgagttgc caagttggaa tcaatcctata   4560
ttccatggag tggactggtt tggcaaatag actgttgagc aagggaaatg acattttgtg    4620
ttgtgactat gctagtttta gtggtctgat aactaagcaa gtcatgagca agatggcaga    4680
aatgataaac agtctttgtg gtggagatga gaaactgatg cgtgagagaa ctcatcttct    4740
gttagcttgt tgctccagga tggcaatctg taaaaagat atttggagag ttgagtgtgg     4800
tatcccctct ggatttccac tcactgttat ctgcaatagc attttcaatg agatgcttat    4860
cagatatagt tatgaaaagt tgttgcgtca agctaaggct cctagtatgt ttctccagtc    4920
ttttagaaat tttatttctt tgtgtgttta tggagatgat aatttaatta gtgttcatga    4980
gtatgtcaag ccatatttta gtggttctaa attgaaaagt ttcctagcta gtcataacat    5040
caccatcact gatggaattg acaaaactag tgcaacttta cagtttagaa agttgtctga    5100
gtgtgatttt cttaaaagaa attttaagca aatgtccaat gttttgtggg tagctcctga    5160
```

```
agacaaagct agtttgtggt cacaattgca ctatgtttca tgtaacaatt tggaaatgca      5220
agaagcttat cttgttaact tggttaatgt gttgcgtgag ttgtacctgc atagtccaga      5280
agaagctcgt cgattgagaa gaaaggctct ctcttgtatt gagtggttgc aaaaagctga      5340
tgtgcccacc atagcacaaa ttgaagaatt tcattcaatg cagaggatta tgaatgctcc      5400
tgattcaaat gataatattg atcttttgtt gagcattgac ttgttgggtc ttcagggtgc      5460
agcaaggcct tcccaaataa gattgtggtt tgatgataaa ttggtattgg caaatacaca      5520
agaattttt gatggaaatt ttccagcaga ttcttggtta ccaatatttg ttaattgtct       5580
ttaccctgtg agtcaattgc ccgcagaagc tgtcattgtt aatgttgttt gtgggagtgg      5640
gcgtggtggt ttgcctacta ctgcttggat tagttctgca gttaacaatc gctcctcaga      5700
tatcaataag aaaattcgga cagcgcttgg aaaaggtaag aaaattgtct ttttgactag      5760
agttgatcct tttcctgtgg ccttgttagc tgttctcttt ggtgttaaga acgaaattct      5820
gagttctaat gccacaaatc caatgttgac aaggcttctt gagaactgca agagtcttaa      5880
atatttggtt gatgagtgtc cttttgcatt tgttaactag tttgtaatat tttgttcact      5940
taaataaagc gcattactat gtgcaataag tgtgtctaaa tataaaaaaa aaaaa           5995

<210> SEQ ID NO 26
<211> LENGTH: 3662
<212> TYPE: DNA
<213> ORGANISM: Bean pod mottle virus

<400> SEQUENCE: 26
tattaaaatt ttcataagat ttgaaaattt tgataaaccg cgatcacagg ttgccgcacc         60
ttaaaaccgg aaacaaaagc aatcgttact tgattttaaa gacttctcaa tttctctcta        120
catttcctgt atacggcttt caaagtgaaa gaaaatcact ctctgtgctg gtcacagact        180
tcgtgaatca tttctttcc attctcagtt catttgctga acactctcct atttgacata         240
ggacttcgtg tcagatttga acttctccta tctctctttc tcggttcttc atttgttggt        300
gaaatcttct gggctagtgc tctcactctc ctatctggca taggacttcg tgagtagact        360
ttcccatttc ttttctcttc tccccctttc ttctcgtctt atacactgct gttcaaagtg        420
gccttatttg aaaaacactt gggcattggt gcaaatgttt gcttcattca tcttttctgg        480
tgacaataag cttactgaga aaacaatttt taactgtggg gatttagata ttttggttgt        540
ttattataca atagccactc aatttaggaa gtttcttcct cattatatta ggtggcattt        600
gtatacgctg ttgattttata ttcttccgtc ttttctcact actgaaatca agtacaagcg       660
aaatttgagc aacattcata tttctggctt gttctacgat aataggttta aattctggac        720
taagcacgat aaaaatcttg ccctaacaga agaagagaag atggaagtga ttagaaacag        780
aggtatccct gctgatgttc ttgcaaagcg cgctcatgaa tttgaaaaac atgtcgctca        840
tgaaagtctc aaggatcaaa ttcctgctgt tgataagttg tactccacta aggttaataa        900
atttgcaaaa attatgaatc ttagacagag tgttgttggt gatcttaaac ttcttactga        960
tgggaagttg tatgagggta agcacattcc tgtatctaat attagtgcgg gagaaaatca      1020
tgtggtgcag atacccttga tggcacagga ggaaattctg tcttctagtg caagtgattt      1080
caagactgct atggtaagca aaagtagcaa acctcaagct acagcaatgc atgtaggggc      1140
tatagaaatt atcattgata gtttcgctag ccctgattgc aacatagttg gtgctatgct      1200
tctagttgat acatatcaca ctaatcctga aaatgcagtc cgtagtattt ttgtcgcacc      1260
tttcagaggt ggtagaccca tcgggttgt cactttccca aacaccattg tgcagattga       1320
```

-continued

```
accagatatg aactcaaggt ttcaactttt gagtacaacc accaatggtg actttgtcca    1380
agggaaagat ctcgcaatgg tcaaggttaa tgtagcatgt gctgctgtag cttaacatc    1440 aagttacact ccaactccat tgttagaatc tggtctgcag aaagacaggg gtcttattgt    1500
tgaatatttt ggaagaatgt cttatgttgc tcataacatc aatcaacctc aagagaaaga    1560
tttgttggag ggaaattttt cctttgatat taagtctcgc tccaggttag agaaagtttc    1620
ttctacgaag gcacaatttg tcagtggaag aacttttaaa tatgatataa ttggtgctgg    1680
ttcacaatct tctgaggaac tttctgagga aaagattcag ggaaaagcaa agcaggttga    1740
tgctaggttg aggcaaagaa tagatccaca atacaatgaa gttcaagctc aaatggaaac    1800
aaatctattc aaattgtctc ttgatgatgt tgagactcca aaaggttcca tgttagacct    1860
caagatttcc caatctaaga ttgcacttcc caaaaataca gttggaggga ccattttgcg    1920
cagtgatctg ctggcaaatt tcttgacaga aggcaatttt agagcaagtg ttgatttgca    1980
acgtacccac cgtatcaaag gaatgattaa aatggtggct acagttggca ttcctgaaaa    2040
cacaggtata gcgctggctt gtgcaatgaa tagttccatt agagggcgtg ccagttctga    2100
tatctatact atttgttcgc aagattgtga actatggaat cctgcttgta caaaagcaat    2160
gactatgtca tttaatccaa acccatgttc tgatgcgtgg agtttggaat ttcttaaacg    2220
tactggattc cactgtgata ttatttgtgt tactggatgg actgcaactc caatgcaaga    2280
tgttcaagtt acaattgatt ggttcatttc ctctcaagag tgcgttccca gaacctactg    2340
tgttttgaat ccacaaaatc cttttgtgtt gaatagatgg atgggaaagt tgacttttcc    2400
tcaaggcact tctcggagtg ttaaaaggat gcctctctct ataggaggag gagctggtgc    2460
taaaagtgct attctcatga atatgccaaa tgcagttctt tcaatgtgga ggtactttgt    2520
aggagatctt gttttgaag tttcaaagat gacctctcct tacattaaat gtacagtatc    2580
ttttttcata gcatttggaa atttggctga tgataccatc aattttgaag cttttcctca    2640
caaattggtg cagtttggag aaattcagga aaaagttgtg ctgaaatttt cacaagagga    2700
gtttctcaca gcatggtcca ctcaggtgcg tcctgcaaca accttgctgg ctgatgggtg    2760
cccatatttg tatgctatgg tgcatgatag ttcagtgtcc acaataccag gtgattttgt    2820
tattggtgtc aagttgacga tcatagaaaa tatgtgcgca tatggactta atcctggtat    2880
ttcaggctcc cgtcttcttg gcaccattcc tcaatctatc tctcagcaga ccgtttggaa    2940
tcaaatggca acagtgagaa caccattgaa ctttgattca agcaaacaaa gcttttgcca    3000
attttctgta gatctccttg gtggaggcat ctcagtagac aaaactggag attggatcac    3060
acttgtgcaa aattctccaa ttagtaatct attgagagtt gctgcctgga agaagggttg    3120
tctgatggtt aaagttgtaa tgtctggaaa cgcagcagtt aagaggagtg attgggcatc    3180
attagtgcaa gtgttcctaa caaatagtaa tagtacagag cactttgatg catgcaggtg    3240
gactaaatca gaaccacatt cgtgggaatt gattttttcca atagaagtgt gtggtcccaa    3300
taatggtttc gaaatgtgga gttctgagtg ggctaatcaa acttcgtggc atttaagttt    3360
tcttgttgat aatccaaaac aatccacgac ttttgatgtt cttttaggga tttcacaaaa    3420
ctttgaaatt gctggaaaca ctctaatgcc agctttctct gttccacagg ccaatgccag    3480
atcttctgaa aatgcagaat cttctgcatg atctggtagt agtgttttct tttcatttgt    3540
ttttgttttc aatcaaataa aggaagttag gcatgaccct cgtttgagaa tggctctgcc    3600
tatttgaaaa tttccacacc tcttttaagt attgtaatag tatgtgaagt gtgtgttatt    3660
tt                                                                  3662
```

<210> SEQ ID NO 27
<211> LENGTH: 5957
<212> TYPE: DNA
<213> ORGANISM: Cowpea severe mosaic virus

<400> SEQUENCE: 27

```
tattaaaatt ttcaagagaa gattttgata ccaaaagcga tcagaggttt gtgccacctt        60
aaaacgcaca acaaaaagct ttcgtaccct cttttcaaga gtcaatccgc attcgagata       120
ccttgaaaga gtacttttct ttccctcttt tcttaattgc tacttacgtt ttcaaaatca       180 cttttctct cttaagctac acaagtttaa ctaaaagcct agaacgaact ttttattgga       240
cgcattaaac tacaatatga agttctttgc tgggcaaact gttatggatg tgctgcaaca       300
tgtttcctct cccaccacca atttaaggtt gttatcttat tgcaatctta aaaaggaaga       360
ggatggtaag atgatgctgg ctattaagga gcagaggcac cgacggttgt tgacactgtc       420
atatggtgct atgtgttttc aattctcaaa ttcagtaggg gatgagggca tagaagtgga       480
tgatgatgag ttgatgtttg aaatatttga tgcattgctg cgcacaaaga tttcaaactc       540
aaagggcatg acgcacttat acagctggat gcgtggagtt tatctcagca cattcaaagt       600
agaggtgcag tgtgatgatt acaactcaaa tctgctggag aaggatttgg ctggagaagc       660
tcagggtctt tcacagttcg tttcaggact tgctgactgg attcccagtc gtgtaaagac       720
cttggcagga tatgccgctg agggcataat tgaggccttt aagaagcact tcgacaaatt       780
gcttgttgag tactgtccta tggccgtggc tgcgtgtagt tggataacta cagtatggac       840
cactatcaaa gagtgggtcc aatctgcgat ggatgctatg tcgtggatta tggctggatg       900
cactgaactc attcttggg gaatgtgtgt cattgcaggt tcatgtgctt tatcgttatt       960
ggaaaaggca ttggtagcta tgggtttgat ttcttcttcc tttgatttag ctggtatctt      1020
tgtacgctct gcggttgttg gagccttttg tttgacggtt gtcaacaaga ggagccgcaa      1080
ttgcgctgag ttgttacaac tagtttcatt ggcggtggga gcagtttcaa gtgcaacatc      1140
atcttgtttc cagtctcctg tagggcaggc aacagatgtg agcgctgaga gtcaatcagg      1200
tggagttgag atgctagagt cacttgctaa gaacttgacc aatttctgtg atggcactct      1260
ggtatctatc ggaaagactt gcaacgctgt aaattcgatc aatacggctg caggtaccat      1320 caaaatctg gtaggtagac tcttgtctat gctaagtaat tttgcataca aactactagg      1380
tttagaatcc acattcttgc gagacgcttc cgtggttttt tctgaaaacg ttgatgggtg      1440
gctaaagcaa atatcttggt gccaagatca atttcttgcc aaggcataca tcaaccagga      1500
tgaacttatg gtgttgcgat ctctcattac cagaggtgaa gttatgcaaa gggagatgat      1560
catgggtggt atgaaagttt cacctacagt ttgtggtttg atcaataaag gatgcacgga      1620
tctcgccaaa ttaatggcag gggctgtgat gcatggaacg agtggtactc ggaaaatacc      1680
atttgttgtt tatgcacatg gggcttctag agttggtaaa acaatggtga tcaacagact      1740
cattgaagat tttcgcaaag agttggaact tggagaggac tgtgtgtatc cacgaaatgt      1800
ggtagatgac tactggagtg ggtacaaaag acaacctatt gttgtcattg atgatttttgg      1860 tgctgtgtct tcagatcctt ctgcagaagc tcaattaatt ccattgatct ctagtgctcc      1920 ctatccccctt aacatggctg atctctctga aagggaatg cactttgatt cagctatcgt      1980
catgtgctca tccaatttca ttgagtgttc accagaaagc aaggtgcgtg acgaaatggc      2040
attcagaaac agacgacatg tgctcttcac tgtctcactt gacccctaata taccatatga      2100 tggtgatgat atcacaaaga atcaaatata tgaaatcaaa acttggtttc atgattcgta      2160
```

```
tcatgttgaa gcaactttca catcatatgg ggacttgctg gcatattgca aaaacaagtg    2220
ggtggagcac aatactgagc aagaggccaa cttgaagcaa cttggagtta aaaggagag    2280
cgttgcattt cagcagtttc gttccattct tgatttggca gtctttgtca atcaagatgc    2340
ggagaattc aagcaaaggc tggagacgcc agatggtagg tgccactttg tgtcatgtta    2400
tgataagagt ggtatactca ggcactatac tattgatgca actggagatg tgcaagaaat    2460
ggaaaaggtt gattcctctc tagatgacat cctattggaa aaaccaaca aaatggtctt    2520
agctgcatat aagatgatta agtaccacaa ggacaccaat ctggtcatta aacccagct    2580
tgcagatttg gtggatccca caaagtatac tgcagatttc cagtttgacg tgttataggg    2640
atcaccactt ttcagcagcc aagtaatgcc aagtgtcaag gcattaccac tgtggcaaag    2700
gatggtactg tacactgttg ggcagaatct gggaagaact cattctagtt ggtatgaggg    2760
catcaaggac aagtgcatgc ttgcactatc aaaagcatac tcaactgaga tcaaggattg    2820
gcctgtagca ctcaaaattg ttgttggagt gatactggct actgtagcag gtaaggcatt    2880
ttggaggttc tatgcctcaa tggcagatgc aggcaatggt ggacactttg tgggagccgt    2940
tgcttccgca tttgcaggaa gtcaagcggt tgttgcacag agtaggaagc ccaacaggtt    3000
tgatgtggct cagtacaggt accgaaacat acctctaagg aagagaaatt gggcagaagg    3060
gcaaatgagt ctggatcagt ccacaatgct cataatggaa aagtgcaagg ccaatttcgt    3120
ctttagcaac attagctgtc agatagttat gttgcctggg cgacaattct tgtgctacaa    3180
acatgtgttt gctagtctca atagtccaat gtatgtggat attttatctg ccaacaagaa    3240
gtataaactc tattacaaac ctcagaatag ggtatacttt gagactgata gtgagatcat    3300
gctatacaag gatgccagtt tggaagacat acctgccagc tgctgggatc ttttttgttt    3360
tgatgcggaa aaaagtttgc cacgaggtag tttcccagca gaaatcctct cgtgcaaact    3420
agatcggaca acgaatcaac atatcccgga atgggccgac atctcagctc gtactgtcaa    3480
tcaaaaactg gacgtggaat tggggagta ccaaaccatc ttttattcct atctccagta    3540
tgatgtatcc acaaaagctg aagattgtgg ttccctaata atagcaacca ttgatggtag    3600
gaaaaagata atagggatcc acactgctgg acgggcaaat aggagtggtt ttgcaagtta    3660
tatgccgcag gtagaaatac cagttcaagc acaagcagcg gaaaagttct ttgattttct    3720
tgagaaagaa caacatgtta ctgagggcat tggaaaggtg ggaaatctca agaaggagt    3780
ctgggttcca ttacccacta agaccaatct tgtggaaaca ccaaaagagt ggcatctggg    3840
cactgagaaa acaaaagaac caagtattct cagcagtacg gatttaaggc tcggtgataa    3900
gcagtatgat cccttttgttg gaggaataca gaagtacgcc gaaccaatgg gaattctaga    3960
tgatgaggtc ctccggcacg tggcaacaga catagttgaa gaatggtttg actgtgtaga    4020
ccctcaagaa gatactttg aggaagttga cctgcaggtt gctatcaatg gtcttgaagg    4080
aatgaaatac atggaaagag ttcctatggc aacatctgaa ggcttcccac acattttgac    4140
aaggaaaagt ggggaaaaag gcaaaggtag gtttgtatat ggggatggag aaattttga    4200
tctgatcccg ggtacatctg tacatgaggc atatctgaca ctggaagaga cttgtgcgga    4260
cactgttcca gccctggttg ggattgaatg tccaaaagat gaaaaacttc ctttgcggaa    4320
gatctatgag aagcctaaaa caagatgttt cactgtactt cctatggaat ataatcttgt    4380
agttaggagg aaatttctca gtttgtggt gtttattatg aagaatcggc acagattatc    4440
ctgccaggtg ggcatcaatc catatggcat ggaatggagt cgcctggcaa tgagcttgct    4500
tgagaaagga aacaacattt tatgttgtga ttacagttca tttgatgggt tgttgacaaa    4560
```

-continued

```
gcaagttatg catctcatga gtgaaatgat caatgaactg tgtgggggat cttcgcgcct    4620
aaagcaacag cgcaccaatt tgttaatggc atgttgttcc aggtatgcat tatgcaaggg    4680
agaagtgtgg cgcgttgaat gtggaattcc ctctggattt ccattgactg tcatttgcaa    4740
cagcattttc aatgagctat tggttagata cagctacatt aagatttgcc aacaagcgcg    4800
tgtgccagcc accataacat acggttttag tacctttgta aagatggtga cttatggtga    4860
tgataactta ctgagcgttc agtctgcaat cactcacgtg tttgatggaa ccaagctcaa    4920
ggagtttctg aaactcaatg gcatcaccat cactgacggc aaagacaaaa cttcccctgt    4980
gcttaatttt cggaatttgg aagattgtga ctttctcaaa aggggcttta agaaagaaag    5040
tgatgtagtg tgggttggac cagaggaaaa ggaatcgctg tgggcacaac tccattatgt    5100
cacgaccaac aatcttgaaa agcatgaagc ttatttggtg aacgttgtaa acgtgatcag    5160
ggaattgtac ctacatgatc aagagaggc tgctgagttg cgtcgcaagg caatacaaaa    5220
tgtagacttc ttgaaggaaa atcctaaaga tttgcccact atggctgcta tcaaggagtt    5280
ctataacatg cagcgacagc aacaatttgt agactccaat gacaatctgg atagtcttct    5340
gaatccagat tttttgtttg ttgccccaca tagaaagatg catgaggccg agatggaatt    5400
agtgccaaag tggtatctga gagatcttgg caaagctcca ataaatgttc taactggaga    5460
agctgatcga atttgtgttc tggttaatgc aagtatccca gaccatcttc ttccagaaaa    5520
ggtggtcaat atatcatggc cttatggacc cggaagggga ggactgccga ctcatggttg    5580
ggcacaggct aatctctaca atccaaatag tgctgtggtg aagaaactgc gtacacttgt    5640
gaatcaaaat cctgatgatc gagtggatat atgttttagg catgatgcag ttccagttgc    5700
gattgcaact atcatttttcc tggttcattt aggaaaggtt aaagggagaa gcgctaatga    5760
atatttgact aaaataattg atagtgcaaa atctctgaag ttcctaccta aggagtgtga    5820
tattattttc tgagtgtatt tgagtttgtg tgtctctttt cttactctca gtctgaataa    5880
ctggcatttt cgccaattta taaaattata atgtgtgatt gttgtgtgtg atttctacag    5940
tacatgttat tactttt                                                   5957
```

<210> SEQ ID NO 28
<211> LENGTH: 3732
<212> TYPE: DNA
<213> ORGANISM: Cowpea severe mosaic virus

<400> SEQUENCE: 28

```
tattaaaatt tttctaggaa aatttttaata caaaagcaat cagaggtttg tgccaccttta     60 aaacgcacac aagcttttcgt accctctttt caagagtcaa tccgtactcg agataccttg    120
aaagagatac attcttcctc tcttactttt ctttatttct cttttaaaact ctcttctttc    180 tgattatcag attccaacaa tctcaggctt aacagagata ctggggacat accaagctgc    240
attaaaatat tgatatgtca actttccgtt ataagtgcaa gcagttggat caagagatac    300
agtggtggtt ttctggaaca ggcaaccgag catttttggaa atttgagaaa aaattggctg    360
aattgcacga gtggtactgg agtttggcac tagaccccatt tccctattct gggttctttt    420
acaagtgctt ttacgaatta tttcaactgt gggtcaaact aggactaatt gtgcaagtaa    480
gctaccttat tttgctcctt gacttttttcg tctacaccat tccaaagaaa atggctagtc    540
agatagaaac tacagtcgaa aaggttaaac aaagtggaat accagcagac atactgcgta    600
aacgcgctgt ggattattgg aagaaaaaca atagccacaa ctcgcagatg caagatgtcc    660
tacccaatgt ggatgaaatc tacgagggta tgcgagcaaa tattgcaaaa tatcttggtc    720
```

```
gcagttccac tgtcacaagt attgccaagc tcggaaagtg caaggtgtat cgaaagaaaa    780
atataccatt agccaacttg ccaagtttgc aaaccagctg tgtgcccatc acactgactg    840
aggaaagtgt aggaaattct gactacacaa ctgaagaaac caattcagaa gtgaaatcat    900
tacacgttgg agctattgaa atcgtgatga atagctttgc gagtagtgat tgtaacattc    960
ttggtggttt cttactaatt gatacatgcc atacagatat caacaatgct attcgtagta   1020
tttttgtggc accaatgaga ggaggtcgac caattaggat gatttctttt cccgacactc   1080
tggtccagat tgagcctaac atgaataagc gttttcaatt gctgtgtaca acaagcaatg   1140
gagacttcat gcaagggcga gatctggcga tgatgcatgt gaatgtgcta gctcatgctg   1200
tcacgcacac atccacctat actcctacac cctactatga gaaaattctc tcacgagaaa   1260
aaggatttat tgtggagtat ctgaatagga tgacttatgc ggttcataac caaaatcatc   1320
ctactgaaaa agatttgctt gaaagtgatt ccaatttga ctttgaaggg caaccagtgc   1380
ttaagagaat ctcatctacc aaagctattt tctctaaagg ttctagtttt cgatatatga   1440
tttctggcaa aaagagcac aagattgaca agccaaggct agaagaagat ggtagtaaga   1500
gttacattga tggtttacaa gatacctttg acacgactca tgctactctg caatctgggg   1560
ctgatctatt caaacgaaat ttggatgatg taagcaccat ttcggacacc atgcttgggg   1620
ccatgattgg acaaccaag gtggtgattc caaaaacatt agttgcaggt acagttctca   1680
aaagtggacc gctttcagat gtgatgcagc agggatcatt ccgatcaaca atagcattgc   1740
aaagaacaca tataataact ggaaaaatac atgttgttgc gatgcttgaa actgctgtaa   1800
ataccaggact gggattggcc atttgtttca atagtggcat tcgaggaaaa gcttctgcag   1860
acatctatgc cacgtgttca caagatgcca tgatctggaa tccatcatgc accaaggtta   1920
tgcaatatgc atttaacct aacccgtgtt ctgatggctg gagcttggct tttttggaga   1980
gaactggtta ccattgtgtg gtcacatgcg tgacaggatg gactgaacg ccattgcaag   2040
acacctttat gaccataaac tggcatattt ctagggaagc atgtgtacca aaaatatata   2100
ccattttga tccagaacca gatatgatgt taaatagatg gatgggacgt gctatctttc   2160
ctcagcaaag tacgcaggtt gtgaggagaa tgccactttc cattggtggt ggtgcaggtg   2220
caaagaattc aattttgatg aaccttccaa atgcaatact atcaatgtgg cgttacttca   2280
aggctgatct tgagtttgaa ctcatcaaga tgtcctcccc atatataaat gcgacaatag   2340
catttttgt ggcctttggg gatctctctg atgatacagt taattttgaa gcttttcccc   2400
acaagttaat tgtcttttct gacaagcaag acaggacgac catatctttc tctaaggatg   2460
aatttttgat ggcatggtcc acacaggtta ggcccgatac taaactcagt gaggatggtt   2520
gccctaccct gtatgccata acgcacaatg gtgttagttc ttctgtggaa ggagatttta   2580
ttcttggtat caagatggtc gggctcaaag ctgtagaaaa cataggagtg aatccaggaa   2640
tcattggatc gcgcttgtta ggggcagttg cccaatctgg acagacacag caggtttgga   2700
ataagatctg gcgcattgga actccaccgc aagccacaga tggtttgttc tcattttcta   2760
tagatcttct tggagttgaa ctggttactg atggccagga gggggcagtt tctgtattga   2820
gcagcagtcc agtagcaaat tgctacgca cagcggcttg gaagtgtgga acgctgcatg   2880
ttaaagttgt tatgactggg agagttacta ccactcgagc caattgggca tcacataccc   2940
aaatgtcact agtgaattct gacaatgctc agcattatga agcacagaaa tggagtgttt   3000
ctacaccaca tgcgtgggaa aaggaatttt ctatagacat atgtggtccc aacagggggtt   3060
ttgagatgtg gcgctcatct tggagtaatc aaaccacatg gatattagaa tttacggttg   3120
```

-continued

```
ctggagcttc tcagtccgca atattcgaaa tattctatcg gcttgataat tcatggaaaa   3180
gtgctggaaa tgttttaatg ccaccattgt tggttgggaa tcccaggctt gacatcaaag   3240
gtcgtgccgc tgcagctgca tagtactata ctttaactat ttgctttaaa taagcctcat   3300
aagtctatga ccccaatttg gtatgctcta gcagaggtaa gtttggtttg caatttcttt   3360
atttttgttg taaacattgt aattagcgta ttgtgtggta gtatatgtta tgctcttttc   3420
acatttcatc catgtattcc caagtcactt tgactctagg taagtggatt aagccttaca   3480
taccaggccg gtcttgggca gcgactgtta aatatgtcca atcactgagg tatcatacgc   3540
catttagttg gttgtgttga tatcgtctaa acagttggcg ttaacgctta tgcatacatt   3600
cagattttat gtgctttatt gcatgtacga atgtacagca tttgctgttg taacgggcta   3660
gtttagaatt atttataaaa gtgtgcaatg tagtaattat gtgtgacttt aattgttcat   3720
tgttcttctt tt                                                       3732
```

```
<210> SEQ ID NO 29
<211> LENGTH: 5865
<212> TYPE: DNA
<213> ORGANISM: Squash mosaic virus

<400> SEQUENCE: 29
tattaaaaat ttctggagaa gaaactttta ataaccatct tcaaggaatc gcgggattcc     60
caccaaagca atctttaaag caatctttaa acattttctg ttttccagct ttgcacttta    120
cggccctgtg gtagattgtg caattgcttt tctccctcct ttcttttctt ttccctcctt    180
cactttccta ctttcaagtg tttttgtttt gtttgtgtga ttaaattaat tcaaaatgaa    240
tttcactgga aatgggagtg ttgctagcgt ccaccaagta gtccattctg aggatgttat    300
gttttatctg aaagcatata ccaatatgac aactgacaac aagggcgcca ctctaccccg    360
tattgtggcg acgttgaagg aggagcaaaa caggcatgtt ttgtatttat cctttttatgc   420 ctattgcttg gattttgatg ctgggttgat ggaaccccac tctgttgacg ttgaggactt    480
tgtttttgag caatttcatg attttgtaac tgccatgctt aaggggtgtc atagccttat    540
gccactgaga tcttatacaa aagctatttt ggccgagcgt ttgcaattag cagtgaattt    600
tgttcctgaa atcactactg agcttggggg ttctggtcct gtggaagccc aaatgcaagg    660
gctgcgaaac attgcagcta acatgttgat gtggatacct aagagaattg gtgctatagc    720
tgcatggaca gtggagagta ttattggaag ttttaaggaa cattttctga agatgattaa    780
tactcattgt ccaatagttt tgtcgacgtt tccctggatt cttaaaatct gggatcgtgt    840
gacagagtgg ttgacaatgg cagctgatga ttttgcgtgg cttttggcct ccaccaagga    900
attgatgaca tggggcatgg ccatcatggc cttaactaca gccatgagtc ttttggataa    960
attgttgatg gcggttggtg ccattactga gcccatgaac ttgtctgata ttttcttgcg   1020
caccggagtt gttgccgcat gttgttatga gctgacaaaa cagagcggca attgtggagc   1080
ccagctgatc tctcttttta gtggtgttgc taatgttgtt gcgggggttt tgagcgcaaa   1140
atttcaaaat cagccccaga ccattttgca agactcccct ataggtttac tggaaacact   1200
cgcggagagg ttaacgagtt tgtgtgatgt ctccttgata aatttgggca aaacgtgtgc   1260
cgcaataaac caaattgcga catgtgctaa cacaattaag ggttttgttg caaagatttt   1320
ttgtactttg acgcattacg tctgggaagc tttgggtatc aaaacctctt ttttgcgaga   1380
cgccactttt gttcttggtg aggatgttga tggctggttg cagcaaatct cccagtgcca   1440
gaatgacttt attgtacatg cctcttgttc tcaggacgag tttcttaagt tgcaggtctt   1500
```

-continued

```
ggccgaaaaa ggcaataaca tgcgaaataa gatcctccaa ggagtccgcc tttccccagg    1560
tatcataagt ttggttacct caggtattgt gatgttagat aagctccgtc gtgaggcttg    1620
tcttcagggc aacagaaccg agaggaaaat gccttttacc attttttgcc aaggaacttc    1680
tcgcgttgga aaacattat tgacttctag aattgtcaaa gatttccagg cagccctagg     1740
gttggctgag acactgtgt acagcaggaa cccggcagaa agttactgga gtgggtatcg     1800
tcgtcagcct tttgttctga ttgatgattt tggtgcagtt aaaactgagc cctcatgtga    1860
ggctcaattg atccctttgg tttcttctac tccttatcct gttccaatgg cggccattga    1920
agaaaaggga atgatgtttg attcacagtt cattgtgtgt tcaacgaatt ttctagaacc    1980
cagtccagag gccaaaatac gtgatgatgc cccgttccgc aatcgccggc acgtgttgat    2040
taatgtcaag attgacaacg aaaggcagta cgattctagt gactttacgc aaaatcagat    2100
ctatgagata atgcgctatg agagagagac atacgttgtg gagcaaagat tcacttctta    2160
tgcggattta tttgtgtttc ttcaaaataa atatgaggcc cacaatgctg aacagtctgc    2220
caacatagga agtgtagttc cctacaaagg caagcaaaac ctactaattc tacgtggtct    2280
gctgaatttg gccaatgttt ctaatgctgg tttattaaaa gctcaagcta agaaacttgg    2340
ccaaccagaa ggttttaggg aatacactca cttattcact atccagcata aaaatcgttt    2400
tgcacatctt ggtttcgctg atgcatatga ctccgtgata tggtatgggg aacattctga    2460
tgttggtagg agtgaggaga tggccaaaat gacggcaagc catgtcatga aggcttacaa    2520
aatccttata cagggtgaaa acttgagctt actcattaaa aatcacttgc gctatcttgt    2580
gtgtcctgac aattatgatc gtgattttaa cttcacgggg ggagttgggg atacactgtt    2640
ggagcaacaa ttgctgccag atatgcaggc tcttcacacc tgggaaagat tgtttttgtg    2700
tgctatgggt tactacatgg aaactcagaa aatgcaacca tggtacaaga ccgtcactga    2760
aaaagttttt gagaatctca aggcagccta ttcacgtgag tttagttcgt ggcccactcc    2820
tttgaaagcc atagttggca tcgtcttggc agctctggtt ggtaaaggtt tttggtttgc    2880
ctacaaggct cttactgaag gtggcaatgg ttccagtctt gttggggctg cttctgttgt    2940
cttgacaagc accaccaatg ccgtcgccca gagcaggaag ccaaatcgtt ttgatgtggc    3000
acaatatcgt taccgtaatg ttcctttgaa gcgcaggcag tgggctgatg cacagatgtc    3060
tttggatcat agcagcgttg ctattatgag caagtgcaag gctaactttg aattcggaaa    3120
taccaatgtg caaattgttt tagttcctgg acggaggttt ttaggatatg cgcatttctt    3180
taagaccatt aaacatccga taacagttaa gatagttaaa gacggccggc actttctcca    3240
tgtttatgat cccaaaggca tgacatattt tgacgattct gagatctgtg tttatcacag    3300
cgctagtttc gaggacatcc cacacactac ttgggatgtt ttttgctggg attgggagaa    3360
aagtctttgt aagaaatttc cagctgactt tcttttcctgt aagtatgaca gattgactat    3420
gtcatatgag cctacatacg ctggcattaa tgtgagaca gttttgaaa ctttggaatt     3480 gcgtgccaat ggtgccgtgc gcaagctccc ttgcttcctg aaatatgagg ctccgacggt    3540
tgatcgggat tgtgggagtc ttatagttgc acaggtagaa ggacgatacc aaatcgttgg    3600
tatacatatt ggaggtgacg ggagaaatgg ctttgcggcc cctttgcccc atattccaca    3660
ggctgccgat gcacagtgca ctaccaagta ctttagtttc tatccaaatg agcaggaaga    3720
agagacaggt gtcgcactag ttggtcagct taagcccgag gtatggatac ccttgccaac    3780 gaaaaacctca ttggtggaga cggaggagga gtggcatttg gacacaaaaa gtgacaaggt    3840
gcctagtatc ttgagttctg aagaccctcg tattaagcaa gggggcaatg aaggatatga    3900
```

```
tccttttaga ggaggtgtta ctaaatattc acaaccaatg gggcacctgt gtggagaaac    3960
ccttggggaa gtagccaatg agattttgga agagtggcat gattgccttg aacccgatga    4020
gaattttgat gatgttgatt tggaagtggc cataaatggt attgatggtt tggattacat    4080
ggatcgtatt cccttagcca cctctgaagg atttcctcat atcttgtcaa gagaaaaagg    4140
ggaaaaaggc aaagggagat tgttgaaac cgtgggtggt aagtgcgctc ttatagaagg     4200
cacttcagtg tatcatgctt ttgaaatctt gcaagagcaa tgtaagaagg aagttcccac    4260
tctgataggg attgaatgcc taaggatga aaagttgcct ctgcgcaaga tttatgacac     4320
cccaaagacg cgttgtttca caatacttcc catggaatac aatttgttgg tgaggatgaa    4380 gttttttaaaa tttgttcgct tcattatgag aaatcgtgag aagcttgcct gtcaggttgg   4440
aatcaacccc tacagcatgg agtggacgag attggctggg agtctttaa gtgtcggcca     4500 gaatattttg tgctgtgact ataaatcatt tgatggcctt ttgagcaagc aagttatgac    4560
ggttatcgcc accatgatca acagattgtg tggtggatcg caggagagtc agaccatgag   4620
aatgaatctc cttatggctt gttgttcccg ttatgctatt tcaaagaacg aggtgtggcg   4680
tgttgaatgc ggtataccct ctggatttcc tttaactgtc atttgtaatt ccattttcaa    4740
tgaaatactt gtgaggtact gttatcggaa aattttggag aagaacaatg taccacgacc    4800
tctacatgtg aattttcctc ggatggtgaa attggttact tatggggatg acaatctgat    4860
ttccgttagt catgttgtcg caagtgtgtt aacggtaga actctgaaag ctgaaatggc    4920
acagtttgga gtgaccataa cagatggtat tgacaaaaca agtccacac tggaatttcg     4980 taagttgagc aattgtgatt tcttgaaaag aggattcaaa ttaaatggtc tcatttacga    5040
ttcaccagag gagaagagta gtctgtgggc tcagcttcat tatgtcaaca caactaacct   5100
ggataagcaa gaagcatatc ttgtgaattt gaataatgtg ctgaaggaat tatatatgta    5160
tagtccagag gaaatgaaca tgctaagaag gaaggctttg cagctacctt ggattaacaa    5220
ggatgatgtg ctaaatgggg ctcagattaa agagtttttt gcctatcagc gccaacaact   5280
acttccagac aatgaggata gcttggatat gatgttaaag ccagatcttt tgggatctct    5340
tgttcctgac gttgtgttgt tggataaggg tgttcaggtg tcaggcaggc tcaaaacgat    5400
aaatctcaag tatactgagc tcggtgaaaa gcgtgacaat gagttttggg ttatctttaa   5460
tggacatttt cctaccaacc gtctccctga gcactgtttg aacattaaat gggaggcagg    5520
cactggtaga gggaatttac caacacagtc ttggataagt aacaacattt ctaggcccaa    5580
ttctgagtat aacaggaaga ttaggactgc ttatgctgct ggaaaggttc tgtgtttctg    5640
tgcctggggt gatatgatac ctgttagtat tatgttgctg ctttcctcag ccagaaacaa    5700
ctggattccc aaaggacaaa cgaatgaggc cttgacctct ttcatggaat atgccaaaag    5760
cctgaaattc ctcccacgtg agtgtgagta tgcctttact gatgtgaagt aaagcttcaa    5820
taaatttaac taacgttatt atcatatgtt gctttgttcg ttttt                   5865
```

<210> SEQ ID NO 30
<211> LENGTH: 3354
<212> TYPE: DNA
<213> ORGANISM: Squash mosaic virus

<400> SEQUENCE: 30
tgtaaagttt gagagagttt aataccgtct cttgatcaaa gatcccacca aagtgtctta 60
aagtgatctc tgctccctct cgcactttac ggctcggtag actgtgctaa gagtttctcc 120
ctctttcttt ttcttcctca accattctaa agtttctcag ccaaatgtat gcatttgctt 180

```
aattcaacta atttgcattc atgtggcatt tctgtgaaca agtttatgag tgttttgagg    240
gttaccataa agactactct gttcaaacag tccctgtgga atatttggcc tcacattaca    300
ttgtcaacaa gtttagaccc gacccttag ctgttttgtg gcttttctgt tgggaattt     360 ggtgggagat tattcaaata ctccactatc tatttcagta taaagaacca gcactttta    420 ttagcagctg tcagaacctt gctgcttttt tagagagaaa gtattccatg gaagtgattc    480
aaaaggaagg tttggctgct tcggcactca aagacaagga gcgattggcc gaaaaagctg    540
tggtcaatca acccctgagt aatttaattc ccaactcaaa taaaatgtat gagcgaagta    600
agagtctcct atctggtctt aagcgtggtt tgataaagca aaaagagata gcttttgaca    660
agcttatggg aggctcaaca atagatttcc aacatattcc aacaggaact ctcacacctg    720
gtgagaacaa agtgctagac ataccaattg ttccgcaaca tttattgacc agtacaaata    780
taacagatta ccatcaagct aacaagaaaa atgctaatgg tgctactgca cttcatgttg    840
gggctataga ggtcattatg gattgcttca cctctcctga tagcaatatt tgtggtggta    900
tgttgctggt tgatacagca catttaaatc cagataatgc tataagaagt gtgtttgttg    960
caccatttat aggtggtcgt cctattcgag ttttgttatt tccagatacc ttggtggaaa   1020
ttgccccgaa catgaattct cgattcaaat tgctatgtac tacgagcaat ggcgatgttg   1080
caccagattt caatttagcg atggttaaag tcaatgttgc aggttgcgct gttagtttga   1140
ctaagacata tactcctaca gcttacctcg agcaagaatt gatcaaagaa aagggggcca   1200
ttgtccaata cttaaacagg cacaccttct ctatgcatcg gaacaaccag atgacaaagg   1260
aagagatgca aaagcagcgc ctctctttta gattggaaag tgctctcact ttgcaggaaa   1320
agcatccttt gcatgccact tttttgcaagt caactaattt tgtttacaag attggtggag   1380
atgcaaaaga aggcagcaat ggcaatttga ctgtcaatga gagccagttg tcctcacatt   1440
ctccttctgc acatgtcttg cacaagcaca taacagtgg tgataatgaa gtagagtttt    1500
cggaaattgg tgtagttgtg ccaggtgctg gcagaactaa ggcttatggc caaaatgagc   1560
tagatcttgc gcaactttct ttggatgata ctagttccct tcgtggatct gcgttgcaaa   1620
ctaaattggc cacttcccgt gtcattctga gcaagacaat ggttggaaat actgtgctca   1680
gggaggattt gctcgccacc tttttgcaag atagcaatga gagggccgct atagatttga   1740
ttcgcaccca tgtcatcaga ggcaaaatac gctgtgttgc ttctataaat gttccagaga   1800
atacaggttg tgcattagct atctgtttca acagtggcat aacaggagca gcagacacag   1860
atatttatac cacaagttct caggatgcca ttgtgtggaa tcctgcttgt gagaaagctg   1920
ttgagttgtc attcaacccc aatccttgtg gtgatgcttg gaattttgtc tttctgcaac   1980
aaacgaaggc acatttgcc attcagtgcg tgaccgggtg gactacaaca ccgcttacag    2040
atttagcgct ggtgcttaca tggcacattg atagaagctt gtgtgtgcct aaaattctga   2100
cgattagttc tgcacatgct tcttttccaa ttaatcgctg gatgggaaag ttatctttc    2160 cgcaagggcc tgcgcgtgtt cttaagagga tgcctttggc tattggtgga ggggctggta   2220 ccaaagacg tattctgatg aatatgccaa acgctgttat ctcacttcac cgatatttta    2280
ggggagattt cgtctttgag ataacaaaga tgagttctcc ttatataaag gcaaccattg   2340
ctttctttat agcgtttggt gatattacag aggaaatgac taatctggag agtttccccc    2400
acaagctcgt gcagtttgct gaaattcagg ggcgtaccac tataacgttc acgcaaagcg   2460
aatttttgac ggcatggtct acacaggtat aagtactgt caatcctcag aaggatgggt    2520
gtccccactt gtacgcactt ttgcatgact ctgctacttc aactattgaa ggaaattttg   2580
```

```
tcattggtgt taaattgctg gacatcagaa actatcgtgc ttacggtcac aacccggtt    2640 ttgagggggc tcgtttgcta ggaatttctg ggcagagtac catggtacag cagcttggaa   2700
cttataatcc aatttggatg gttcgcacgc ccttagaaag tacagcccaa caaaattttg   2760
cgagtttcac tgctgatttg atggaatcca cgataagtgg ggactctact ggaaactgga   2820
atatcacagt ttatcctagt cctatagcta atttgctgaa agtggctgct tggaagaaag   2880
gaactataag atttcaactt atttgtcggg gtgccgctgt caagcagtct gactgggctg   2940
cgtcagctag aatagacttg attaacaacc tctcgaacaa ggctctaccc gcgcgttcct   3000
ggtacattac aaagccacga ggaggcgaca tcgagtttga cttagagata gcgggaccaa   3060
ataatggttt tgaaatggcg aattccagtt gggctttcca gaccacatgg tacttggaaa   3120
ttgccataga taatcccaag caatttactc cttttgaatt aaatgcctgt cttatggaag   3180
attttgaagt ggctggaaat actttaaatc cacctatttt gctttcctag tttttctgtt    3240
ctttgtttcc ttcttttctg ggttttgttg tggcttcttt cccagttcgc tttagaagcc   3300
tctctttgta aatcttaaga gcttgttttc tttgatgcat tctcttttct tttt           3354
```

BIPARTITE SYSTEM, METHOD AND COMPOSITION FOR THE CONSTITUTIVE AND INDUCIBLE EXPRESSION OF HIGH LEVELS OF FOREIGN PROTEINS IN PLANTS

The present application is §371 application of PCT/IB2006/003548 filed 22 May 2006, the entire disclosure of which is incorporated by reference herein.

FIELD OF THE INVENTION

This invention relates to the fields of molecular biology and transgenic plants. More specifically, a bio-contained system, method and composition for expression of proteins in plants without production of infective viral particles are provided.

BACKGROUND OF THE INVENTION

Several publications and patent documents are cited throughout the specification in order to describe the state of the art to which this invention pertains. Each of these citations is incorporated herein by reference as though set forth in full.

Viral vectors have the advantage that the heterologous gene is amplified, leading to potentially high levels of expression, but there are constraints on the size of protein that can be expressed before genetic instability becomes a problem. Furthermore, concerns have been expressed about the ability of autonomously viral vectors carrying foreign genes to spread in the environment. In the past few years, the use of viral vectors for the expression of foreign proteins in plants has attracted considerable attention. There are currently two principal means for the expression of such heterologous proteins using viral vectors in plants: transient and stable genetic transformation.

Stable transformation has the advantage that there are few, if any, limitations on the size or complexity of the proteins that can be expressed; however high expression levels can be difficult to achieve routinely. There have been a number of attempts to develop systems that combine the advantages of the transgenic and viral vector approaches. These have generally involved integrating replication-competent cDNA copies of RNA plant viral genomes into genome of a host plant. Virus-specific RNAs transcribed in the nucleus are then amplified by the virus-encoded RNA-dependent RNA polymerase (RdRp). Early attempts to develop this approach using Brome mosaic virus (BMV; Mori et al., 1993) or Potato virus X (PVX; Angell and Baulcombe, 1997) resulted in low levels of protein expression due to replicating viral RNA invoking efficient post-translation gene silencing (PTGS; Kaido et al., 1995; Angell and Baulcombe; 1997; 1999). Attempts to alleviate this problem have involved either the use of an inducible promoter in the case of BMV (Mori et al., 2001) or by introducing a known suppressor of PTGS in the case of PVX (Mallory et al., 2002).

It has recently been shown that transformation of *Nicotiana benthamiana* with full-length, replication-competent cDNA copies of both genomic RNAs of Cowpea mosaic virus (CPMV; FIG. 1a) results in a productive infection (Liu et al., 2004). This effect was achieved irrespective of whether the two RNAs were introduced simultaneously by co-transformation or by crossing separate RNA-1 and RNA-2 transgenic lines. Furthermore, inoculation of RNA-2 transgenic plants with RNA-1 also gave rise to an infection, though no infection resulted from the reciprocal experiment. This asymmetric complementation between transgene and inoculated genome segment has been attributed to the fact that RNA-1 can act as an amplicon whose effects in inducing PTGS can be counteracted by the presence of an RNA-2-encoded suppressor of silencing which has been identified as the C-terminal region of the Small (S) coat protein (Liu et al., 2004; Cañizares et al., 2004). It has previously been shown that it is possible to insert heterologous sequences into RNA-2 without affecting its ability to be replicated by RNA-1 (Usha et al., 1993, Lomonossoff and Hamilton, 1999; Gopinath et al., 2000).

Although transgenic plants represent promising production systems for long-term and large-scale needs, the time needed to produce expression cassettes containing multiple transgenes, transform plants, and regenerate and multiply transgenic plants imposes a time constraint in the development of a production process.

Transient expression systems allow for the rapid expression of foreign proteins. However, although viral-based transient expression systems have been widely used for the expression of heterologous proteins in plants, limitations of such known systems appear when large amounts of proteins are needed and when producing complex multimeric proteins like monoclonal antibodies. In 1998, Verch et al. (Journal of Immunological Methods 220 (1998) 69-75) report, for the first time, expression of a full size antibody in plants using a viral vector. The paper presents expression of a full size antibody upon co-infection of *Nicotiana benthainiana* plants with two independent TMV genomic RNAs containing the antibody light and heavy chains, respectively. However, although the authors conclude that assembled antibodies were produced, the level of production was too low to be feasible for commercial antibody production purposes.

Agro-infiltration in detached leaves has also been used for the transient production of antibodies. This transient expression system, first published by Kapila et al. (Plant Science 122 (1997) 101-108) relies on the vacuum-forced entry of Agro-bacteria in leaf tissue, followed by infection of plant cells by the bacteria, transfer of the T-DNA into the nucleus of the plant cells, and transient expression of the gene or genes of interest. The application of Agro-infiltration for full size antibody production has first been reported by Vaquero et al. (PNAS 96 (1999) 11128-11133). In that paper, the authors present the expression of recombinant antibodies specific for the human carcinoembryonic antigen (CEA), a tumor cell surface antigen. Other reports of the use of vacuum-based Agro-infiltration for the production of full size antibodies in plants include Kathuria et al. (Current Science 82 (2002) 1452-1457), Rodriguez et al. (Biotechnology and Bioengineering 89 (2005) 188-194), and Hull et al. (Vaccine 23 (2005) 2082-2086). In opposition to stable transformation of plants, the Agro-infiltration transient expression system is extremely rapid and multiple transgenes can be expressed simultaneously in the same cells simply by co-infiltrating a mixture of *Agrobacteria*, each strain bearing one gene of interest. The production of antibodies using co-infiltration is exemplified in D'Aoust et al. (Efficient and reliable production of pharmaceuticals in alfalfa, in Molecular Farming, ISBN 3527307869) and Hull et al (Vaccine 23 (2005) 2082-2086).

To date, combining Agro-infiltration and viral vectors into a transient expression system has proven to be very efficient for single protein production. For example, Marillonnet et al. (PNAS 101 (2004) 6852-6857) show extremely high expression levels of GFP in *Nicotiana benthamiana* upon Agro-inoculation of leaves with *Agrobacteria* containing a TMV-based viral expression cassette engineered to produce recombinant GFP. However, the co-expression of different sub-units in the same cells using the TMV expression system has not been possible. At the Conference on Plant-Made Pharmaceuticals in Montreal (Jan. 30 to Feb. 2, 2005), the results presented by Yuri Gleba (Icon genetics) showed that upon infection of plants with two different TMV-based viral vectors, competing vectors rapidly segregate and cells accumulated either one or the other RNA of interest, but not both. A solution to this problematic competition between viral vectors was presented at the Plant-Based Vaccines and Antibodies meeting (Jun. 8 to 10, 2005) by Sylvestre Marillonnet (Icon Genetics). The presentation entitled "Expression of protein fusions and of single chain and monoclonal antibodies in plants using viral vectors" proposed a co-infiltration strategy in which elements from different viruses (TMV and PVX) were used when co-expression of different proteins was needed in the same cells. It was shown that, in *Nicotiana benthamiana* leaves, the TMV- and PVX-based vectors do not compete and that high levels of two proteins in the same cells can be achieved using this strategy. Thus, the production of monoclonal antibodies using this transient expression system combining Agro-inoculation and viral expression vectors is possible. Nonetheless, despite successfully producing antibodies in plants by Agro-inoculation, the combined TMV-PVX viral vector system is dependant on coordinate expression and amplification of independent RNAs from different RdRPs.

In view of the foregoing, it is clear that a need exists for an efficient viral-based transient expression system capable of producing two different proteins in the same cells, particularly in cases high levels of protein production have been difficult to achieve.

SUMMARY OF THE INVENTION

In accordance with the present invention, an efficient viral RNA-based expression system capable of rapidly producing significant amounts of heterologous proteins in higher plants is provided which comprises the use of exemplary bipartite transgene/viral vectors. In a preferred embodiment, the system is bio-contained such that the viral vectors employed are incapable of producing infective viral particles.

Thus, in one aspect of the invention, a plant gene expression system is provided which comprises a first gene construct comprising a truncated RNA-2 of a bipartite virus genome carrying at least one foreign gene encoding a heterologous protein of interest operably linked to promoter and terminator sequences; a second gene construct comprising RNA-1 of said bipartite virus genome operably linked to promoter and terminator sequences; and a third gene construct, optionally incorporated within said first gene construct, said second gene construct, or both, comprising a suppressor of gene silencing operably linked to promoter and terminator sequences. Robust production of the heterologous protein of interest results upon co-expression of the three nucleic acid constructs in a plant cell. The constructs may be expressed transiently or stably incorporated in plant cells. Alternatively, constructs may be introduced into plant cells via crossing or agroinfiltration. In a preferred embodiment, at least one construct is expressed transiently and at least one construct is stably integrated into the genome of said plant cell.

Preferably, the first gene construct and the second gene construct are derived from a Comovirus. Such viruses include, without limitation, Cowpea Mosaic Virus (CPMV), Red clover mottle virus (RCMV), Bean pod mottle virus (BPMV), Squash mosaic virus (SqMV) and Cowpea severe mosaic virus (CPSMV).

Suppressors of gene silencing useful in the system and method described herein include, HcPro from Potato virus Y, Hc-Pro from TEV, P19 from TBSV, rgsCam, B2 protein from FHV, the small coat protein of CPMV, and coat protein from TCV. Most preferably, the RNA-2 of the system is truncated such that no infectious virus is produced.

In another aspect of the invention, a gene construct encoding a truncated RNA-2 molecule operably linked to a nucleic acid encoding a heterologous protein interest, each being further optionally linked to promoter and terminator sequences functional in a plant cell is provided. Exemplary truncated RNA-2 molecules include, for example, those having a deletion of greater than 2700 nucleotides in the RNA-2 sequence. Preferred truncations of RNA-2 include those wherein the sequences between nucleotides 512 and 3300 have been replaced with a coding region for a heterologous protein of interest. Alternatively, RNA-2 sequences between nucleotides 524 and 3300 may be replaced. Heterologous proteins of interest include, without limitation, multimeric proteins, cytokines, vaccines, enzymes, growth factors, receptors, interferons, hematopoeitic agents, pituitary hormones, thyroid hormones, hypothalamic hormones, albumin, insulin and pancreatic hormones. In a preferred aspect of the invention, the system is employed to produce antibodies with affinity for proteins having commercial or therapeutic value.

Also included in the present invention are plants comprising the gene expression system described above, and plant cells or progeny obtained therefrom.

In yet another aspect of the invention, a method for expressing a foreign gene in a plant cell is provided. An exemplary method comprises providing a first gene construct, said construct comprising at least one truncated RNA-2 construct of a bipartite virus genome and at least one nucleic acid encoding a heterologous protein of interest operably linked to promoter and terminator sequences; providing a second gene construct, said construct comprising RNA-1 of said bipartite virus genome; providing a third construct encoding a suppressor of gene silencing into said plant cell; and introducing said first, second and third constructs into a plant cell, thereby producing said heterologous protein of interest. The constructs of the invention may be introduced into said plant cell simultaneously or sequentially. They may be expressed transiently, or stably incorporated into the plant cell genome. Alternatively, the constructs may be introduced via crossing with plant cells harbouring said construct. Most preferably, the truncation of RNA-2 prevents the production of infectious viral particles in the presence of functional RNA-1. The constructs of the invention may each possess discrete promoter and terminator sequences. Alternatively, they may be operably linked in a polycistronic fashion such that a single promoter and a single terminator control the expression of at least two coding regions.

In yet another aspect of the method, stable transformation and transient expression are performed in different locations such that no *agrobacterium* carrying a gene of interest is manipulated in an area where the production and harvest of a product of gene expression is performed. Also encompassed by the invention are plants produced using the method described as well as plant cells and progeny obtained therefrom.

Other objects and advantages of this invention will be apparent from a review of the complete disclosure and the claims appended to this disclosure.

This invention satisfies a long felt need in the art for a high-level plant expression system in which bio-containment considerations are significant.

BRIEF DESCRIPTION OF THE DRAWINGS

FIG. 1: Diagram of constructs used for transformation and agroinoculation. (a) Wild-type CPMV RNA constructs. 35S-

RNA-1 and 35S-RNA-2 contain full-length cDNA copies of wild-type CPMV RNA-1 and RNA-2, respectively, between the 35 S promoter and Nos terminator in pBINPLUS. The RNA-1 ORF encodes a polyprotein which is proteolytically processed by the 24K proteinase domain to yield proteins involved in RNA replication. The RNA-2 ORF encodes 2 carboxy-coterminal polyproteins which are processed by the RNA-1-encoded 24K proteinase to the 58 and 48K overlapping proteins and the Large (L) and Small (S) coat proteins (CP). (b) Modified versions of RNA-2 designed to express GFP. 35S-RNA-2-GFP is a full-length version of RNA-2 containing a sequence encoding GFP fused in frame to the RNA-2 ORF via a Foot-and-mouth disease virus (FMDV) 2A catalytic peptide sequence (black box). Constructs 35S-5'3'-GFP, 35S-1-GFP and 35S-2-GFP consist of deleted versions of the RNA-2 sequence plus the sequence of GFP. The portion of the RNA-2-specific ORF retained in the constructs are shown as an open box and the position of the AUG used to initiate GFP translation is indicated. The sequence of GFP is shown as a grey box. In all constructs, the 35S promoter and nos terminator are indicated by the arrow and small box, respectively.

FIG. 2: Inducible expression of GFP in RNA-2-GFP transgenic plants. (a) Induction of fluorescence in the upper (systemic) leaves of a RNA-2-GFP transgenic *N. benthamiana* plant agroinoculated on its lower leaves with RNA-1. The photograph was taken using a hand-held ultraviolet lamp. (b) Analysis of induced levels of RNA-2-GFP mRNA in *N. benthamiana* plants inoculated with RNA-1 (lanes marked RNA-2-GFP-3+RNA-1). Samples were taken from inoculated, lower leaves (IL) as well as old (OL), mature (ML) and young (YL) upper systemic leaves. The top two panels are five (top) or fifteen (middle) minutes exposures of the same northern blot probed with a sequence specific for GFP. The position of full-length RNA-2-GFP is indicated. As controls, samples were taken from lower leaves of a 2NTGFP-3 plant prior to inoculation with RNA-1 (RNA-2-GFP-3) and from a non-transgenic *N. benthainiana* (NT) plant. The bottom panel is a loading control showing ethidium bromide-stained 25S rRNA. (c) Western blot analysis of GFP expression in RNA-2-GFP transgenic *N. benthamiana*. The protein samples analysed were from plants as described in (B). The positions of free GFP and GFP fused via the FMDV 2A sequence to the S CP(S-2A-GFP) are indicated. The bottom panel shows a Coomassie-blue stained gel of total protein as a loading control. Each lane is estimated to contain approximately 20 μg of protein.

FIG. 3: Constitutive expression of GFP in plants transgenic for RNA-2-GFP and RNA-1. (a) Fluorescence on line 7-1 plants transgenic for both RNA-2-GFP and RNA-1 (right) or RNA-1 alone (left). The photograph was taken using a hand-held ultraviolet lamp. (b) Northern blot analysis of RNA extracted from old (OL), mature (ML) and young (YL) fluorescent and young non fluorescent (YNF) leaves of *N. benthamiana* transgenic for RNA-2-GFP and RNA-1 (line 7.1). Controls were RNA extracted from an RNA-1 transgenic plant (11F2) and a non-trangenic (NT) plant. The blot was probed with a sequence specific for GFP and the position of full-length RNA-2-GFP is indicated. The bottom panel is a loading control showing ethidium bromide-stained 25S rRNA. (c) Western blot analysis of GFP expression in RNA-2-GFP and RNA-1 transgenic *N. benthamiana*. The protein samples analysed were from plants as described in (b). The positions of free GFP and GFP fused via the FMDV 2A sequence to the S CP(S-2A-GFP) are indicated. The bottom panel shows a Coomassie-blue stained gel of total protein as a loading control. Each lane is estimated to contain approximately 20 μg of protein.

FIG. 4: Expression of GFP before and after agroinfiltration of leaves of *N. benthamiana* transgenic for the deleted versions of the RNA-2 harbouring GFP. Leaves of plants transgenic for 5'3'-GFP, 1-GFP and 2-GFP were photographed under UV light either before (Non-infiltrated) or 6 days post-infiltration with *A. tumefaciens* containing 35S-HcPro (HcPro), 35S-RNA-1 (RNA-1), 35S-RNA-1 plus 35S-RNA-2 (RNA-1+RNA-2) or 35S-RNA-1 plus 35S-HcPro (RNA-1+HcPro).

FIG. 5: Northern and western blot analysis of GFP expression in agro-infiltrated leaves shown in FIG. 4. Upper panels: northern blots of RNA extracted from leaves of transgenic lines 5'3'-GFP, 1-GFP, 2-GFP or non transgenic plants probed with sequences specific for either positive (+ strands) or negative (− strands)-sense GFP. The position of the deleted RNA-2-GFP is indicated. The levels of ribosomal RNA (rRNA) are shown as a loading control. Lower panels: western blot analysis GFP-specific serum of GFP expression using in the same leaves. The bottom panel shows a Coomassie-blue stained gel of total protein as a loading control.

FIG. 6: GFP expression levels after agroinfiltration with 35S-1-GFP (a) GFP expression in leaves from transgenic lines 11F2 (lane 11F2), HcPro-11 (lane HcPro) and 11F2xHcPro (lane 11F2xHcPro). The plants were agroinfiltrated with 35S-1-GFP and photographed 8 days post infiltration under UV illumination. (b) Coomassie blue stained polyacrylamide gel of proteins (10 μg/lane) from leaves agroinfiltrated with 35S-1-GFP. Protein extracts were prepared from non-transgenic (lanes marked NT), and plants transgenic for either RNA-1 (lane 11F2), HcPro, (lane HcPro) or RNA-1 plus HcPro (lane 11F2xHcPro). The samples were taken 4 dpi in the case of the NT and 11F2 samples and 8 dpi in the case of those from the HcPro and 11F2xHcPro leaves. The two samples on the left represent marker proteins and proteins extracted from non-transgenic (NT) leaves which were not infiltrated with 35S-1-GFP, respectively. A standard of 300 ng of purified GFP is shown in the right hand lane. (c) Upper panels: northern blot analysis of RNA extracted from the same samples as shown in (b), probed with sequences specific for either positive (+ strands) or negative (− strands)-sense GFP. The position of deleted RNA-2-GFP is indicated. The panels below those showing the + and − strands are ethidium bromide stained gels of the same samples used for northern analysis to assess the levels of ribosomal RNA (rRNA) as a loading control.

FIG. 7: GFP expression levels in the plants resulting from crossing 11F2xHcPro plants with 1-GFP transgenic plants. (a) Fluorescence of 1-GFP transgenic plants before and after the crossing with line 11F2xHcPro. The plant on the left was shown to contain all three transgenes by PCR analysis. The photograph was taken using a hand-held ultraviolet lamp. (b) Upper panels: Northern blot analysis of RNA extracted from a 1-GFP transgenic plant before crossing (before) and from 4 separate plants (1-4) produced after crossing with 11F2xHcPro plants. All 4 plants were shown to contain all three transgenes. The blots were probed for either positive (+ strands) or negative (− strands) sense GFP RNA. An ethidium bromide stained gel of rRNA is shown below the blots as a loading control. Bottom panel: western blot analysis of GFP expression using GFP-specific serum of protein extracts from the same leaves as used for RNA analysis. A Coomassie-blue stained gel of total protein is shown below as a loading control.

FIG. 8. Genome organization of CPMV and RCMV RNA-2. In both cases the RNA is polyadenylated and has a small protein (VPg) linked to its 5' end. The $1^{st}$ two in-phase AUG codons are indicated. The 58/48K proteins are derived from initiation at the first two AUGs. The regions coding for the large (L) and small (S) coat proteins are also indicated.

Figure 9:
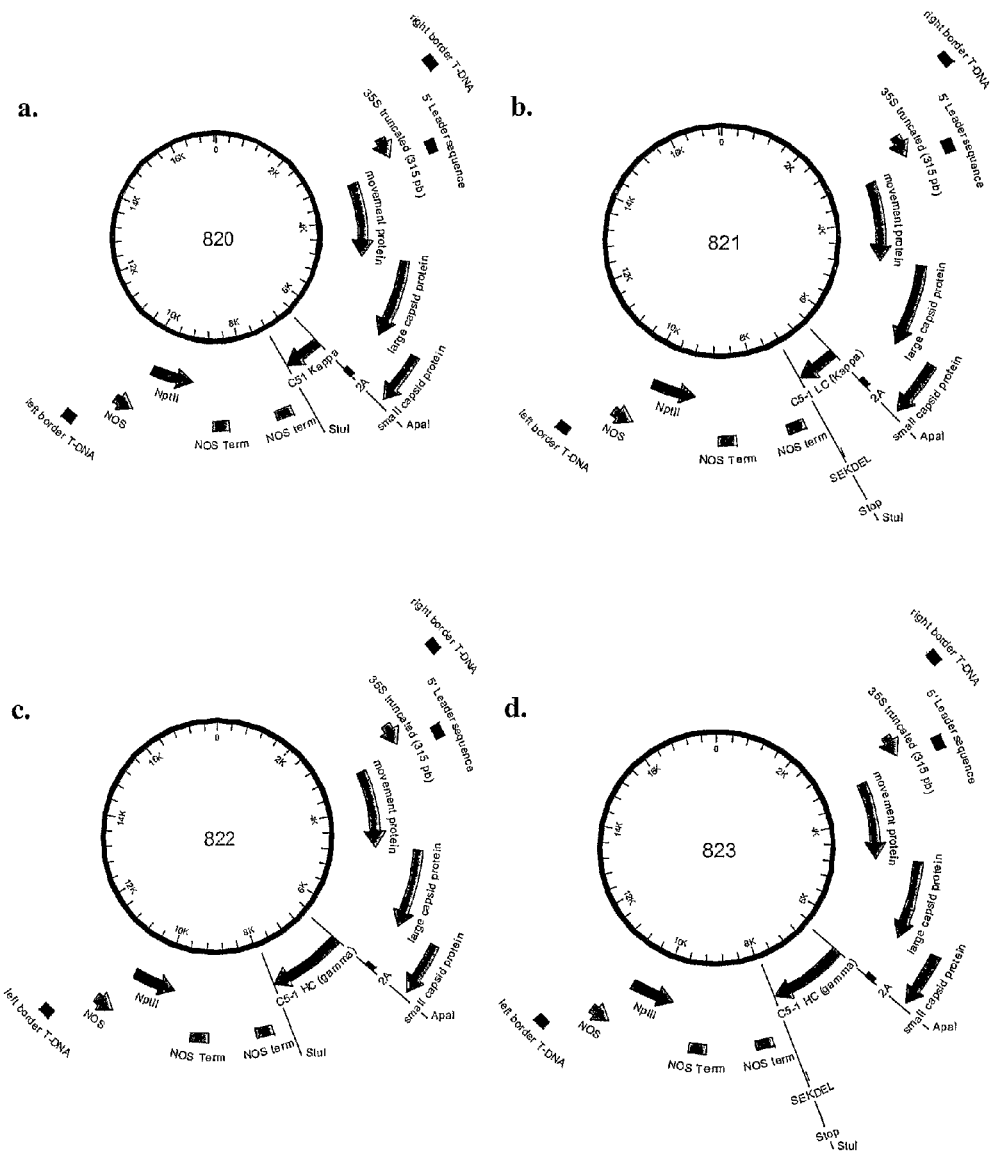

FIG. 9. Representation of the CPMV-based constructs used for the expression of C5-1. (a) Plasmid 820 contains C5-1 kappa chain coding sequences. (b) Plasmid 821 contains an ER-retained form of the C5-1 kappa chain coding sequence. (c) Plasmid 822 contains C5-1 gamma chain coding sequences. (d) Plasmid 823 contains an ER-retained form of the C5-1 gamma chain coding sequence.

Figure 10:
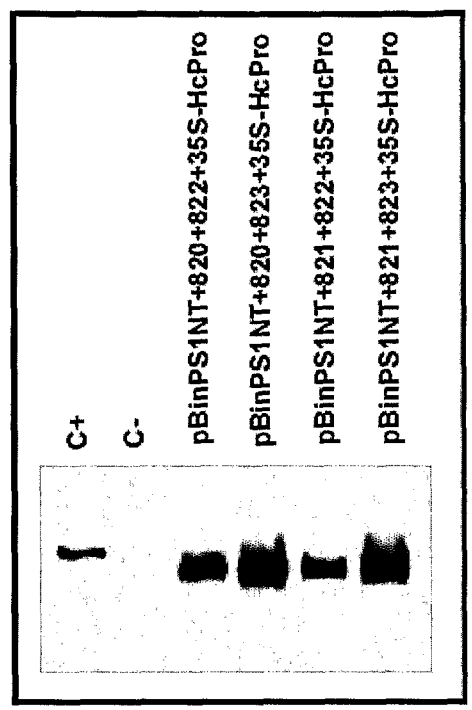

FIG. 10. Immunological analysis of transient C5-1 production using the CPMV RNA-based expression system in *Nicotiana benthamiana*. Negative control (C−) is constituted of 5 µg total proteins from a leaf inoculated with pBinPS1NT and 35S-HcPro. For the positive control (C+), 10 ng of purified C5-1 were spiked into 5 μg total proteins from a leaf inoculated with pBinPS1NT and 35S-HcPro.

FIG. 11. Representation of the CMV-based constructs used for the expression of C5-1. (a) Plasmids 824 and 825 contain C5-1 kappa chain coding sequences. (b) Plasmids 826 and 827 contain C5-1 gamma chain coding sequences.

FIG. 12. Immunological analysis of transient C5-1 production using the truncated CPMV RNA-based expression system in *Nicotiana benthamiana*. Arrowhead indicates the expected size of the fully assembled antibody.

FIG. 13. Representation of the RCMV-based constructs used for the expression of C5-1. (a) Plasmid 850 contains C5-1 kappa chain coding sequences. (b) Plasmid 852 contains C5-1 gamma chain coding sequences.

DETAILED DESCRIPTION OF THE PREFERRED EMBODIMENTS OF THE INVENTION

In accordance with the present invention, a recombinant DNA system in which high levels of protein expression are achieved in plants while ensuring bio-containment of the transgenic construct is provided. The system and method take advantage of bipartite plant viral vectors which are engineered such that no infective viral particles are produced.

Also included in the scope of the invention are methods entailing the use of genetic material from members of the Comoviruses, a group of plant viruses in the picornavirus superfamily with nonenveloped, icosahedral capsids and bipartite, single-stranded, positive-sense RNA genomes. Such viruses include, without limitation, Cowpea Mosaic virus (CPMV), Red clover mottle virus (RCMV), Bean pod mottle virus (BPMV), Squash mosaic virus, (SqMV) and Cowpea severe mosaic virus (CPSMV). The genome of the Comoviruses includes two RNA molecules (termed RNA 1 and RNA 2) which are encapsidated separately in isometric particles made up of 60 copies each of a large (L) and a small (S) coat protein. A number of strains of CPMV and RCMV have been characterized. Inspection of the RNA sequence together with in vitro translation data indicates that RCMV has a mode of gene expression similar to that observed in Cowpea mosaic virus (CPMV). Depending on the tropism required, a particular viral system based on the methodology and specifics disclosed herein may be produced for use with a given plant system. Thus, for alfalfa, the viral system of choice may be RCMV, while for a different plant system, another comovirus may be chosen. The essential principals as laid out herein, however, may be utilized and adapted for each plant/viral system chosen.

Attempts to develop a combined virus/transgene system based on CPMV have focused on the use of full-length versions of RNA-2. There were two principal reasons for this. First, practical, autonomously replicating vectors based on RNA-2 have been used successfully for foreign gene expression in plants (Gopinath et al., 2000; Liu and Lomonossoff, 2002; Liu et al., 2005). Secondly, RNA-2 is known to encode a suppressor of PTGS which is necessary for efficient CPMV replication (Liu et al., 2004; Cañizares et al., 2004) and removal of this suppressor was thought to be likely to have deleterious consequences on RNA replication and concomitantly on protein expression. Surprisingly, we show herein that we can supply this functionality in trans and achieve high levels of expression.

The results obtained with lines of transgenic plants harbouring a complete copy of RNA-2 containing GFP(RNA-2-GFP) demonstrate that that transgene-derived mRNA can be amplified to a high degree when RNA-1 is supplied either exogenously or by crossing. Since the sequence of GFP in RNA-2 constructs can readily be replaced with another coding sequences, it is without question that it is possible to express valuable proteins in either an inducible (exogenous RNA-1 application) or constitutive (introduction of RNA-1 by crossing) manner. The very low levels of RNA-2-GFP-specific transgene mRNA and GFP that were detected in the absence of RNA-1 (FIG. 2*b, c*) were anticipated since, in the absence of RNA-1, no amplification of RNA-2 will occur. As the replication of CPMV RNA-2 is highly specific and cannot be induced even by the RNA-1 of other comoviruses (Goldbach and Wellink, 1996), it is highly unlikely that replication could be triggered accidentally. Thus a system based on supplying RNA-1 of the comovirus is a very tightly regulated system.

In addition to the general advantage of replicating a transgene-derived mRNA to enhance expression levels, the CPMV system disclosed herein as an exemplary and preferred embodiment of this invention for production of proteins in certain plant cell types has several specific advantages. Among these are the fact that exactly the same *Agrobacterium*-based constructs can be used for agroinoculation and stable transformation. Since practical CPMV RNA-2-based vectors for foreign gene expression are already available (Gopinath et al., 2000; Liu et al, 2005), it is possible to carry out rapid preliminary characterisation of protein expression in transient assays before transformation is undertaken. Since every cell in a transgenic plant will contain a "master copy" of the foreign sequence embedded in RNA-2, an enhancement in the genetic stability of heterologous sequences over that found with autonomously replicating constructs can be anticipated, permitting the stable expression of larger proteins. Indeed, preliminary experiments with integrated RNA-2 constructs expressing modified antibodies indicate this is, indeed, the case.

Both the "constitutive" and "inducible" strategies for expression permit the simultaneous high level expression of RNA-2 molecules containing different foreign sequences within the same cells. This, in turn allows the production of complex, multi-chain proteins. Though the constitutive approach should provide larger amounts of leaf tissue from which the expressed proteins can be processed, the inducible option allows the expression of foreign genes with negative effects on plant growth that could not be expressed to high level using constitutive systems such as the previously developed amplicon plus-system (Mallory et al., 2002). The ability to use the system disclosed herein, as exemplified by the preferred CPMV system, in either an inducible or constitutive way and the fact that higher expression levels (approximately 7-10 times greater) can be obtained gives it advantages over the combined transgene/virus vector system based on Brome mosaic virus (BMV) reported previously (Mori et al., 1993, 2001).

The principal potential disadvantage associated with known full-length versions of RNA-2 is that the induction of replication leads to the formation of viable virus particles which can spread to further plants. Though this may, in certain circumstances, be advantageous especially where large amounts of plant material expressing the desired protein are required, it may cause problems if bio-containment is considered to be of high priority. Thus we investigated the development of replicons based on defective versions of RNA-2 which will not give rise to viable virus. To this end, the coding region of RNA-2 was replaced with that from GFP in a series of three constructs in which translation of GFP was designed to occur after AUG161 (5'3'-GFP), AUG512 (1-GFP) or AUG 524 (2-GFP) of the RNA-2 sequence. The fact that RNA from only 1- and 2-GFP could be replicated is consistent with the earlier observation that RNA-2 sequences downstream of AUG161 are essential for RNA-2 replication (Rohll et al. 1993; van Bokhoven et al., 1993). Indeed, mutation of AUG161 itself severely affects RNA-2 replication (Holness et al., 1989). We have retained this AUG in constructs 1- and 2-GFP. Without wishing to be bound by mechanistic considerations, the fact that 1- and 2-GFP directed the translation of only GFP without a 14 kDa N-terminal extension suggests either that AUG161 is rarely used for initiation in these constructs or that the fusion protein is highly unstable. Since 1-GFP and 2-GFP gave very similar results in terms of RNA replication and levels of GFP expression, constructs according to this invention are preferably based on 1-GFP as this results in proteins with an authentic N-terminus. Thus, in one embodiment, the 5' portion of the construct consists of nucleotides 1-512 or 1-524 of RNA-2 operably linked to a nucleic acid encoding the heterologous protein of interest which is in turn operably linked to the 3' portion of RNA-2 which consists of nucleotides 3300 to 3481 followed by the polyA tail. However, an artificial AUG codon may be engineered into the constructs, thereby facilitating placement of the coding region encoding the protein of interest between positions 161 and 512.

The ability of transgene-derived defective RNA-2 molecules to be replicated by the co-application of RNA-1 and HcPro as demonstrated herein shows that it is possible to produce an inducible system based on such molecules. Furthermore, and of significant advantage from a bio-containment perspective, is our demonstration herein that, in the absence of the viral coat proteins, no virus particles are produced and the ability of the virus to spread in the environment is therefore curtailed. For small scale production, mechanical agroinfiltration of leaves with RNA-1 and HcPro suffices. Scale-up is achieved through, for example, the use of vacuum infiltration (Vaquero et al., 1999).

To produce a constitutive system based on defective RNA-2 molecules, we generated plants transgenic for both RNA-1 and HcPro. We show these plants to be capable of supporting the replication of construct 1-GFP and of giving high levels of GFP expression. Similarly high levels of GFP expression were obtained when 1-GFP was agroinoculated into HcPro single transgenic plants. When we crossed the double transgenic plants with those transgenic for 1-GFP, the progeny containing all three transgenes were fluorescent while those transgenic for just HcPro and 1-GFP were not. The relatively low level of GFP expression in plants transgenic for HcPro and 1-GFP appears to contradict the agroinfiltration results. However, we conclude that the difference is due to the fact that the suppressor acts to prevent the degradation of RNA. Where large amounts of RNA are being synthesised (as is the case in agroinfiltration) replication of the RNA is not required to achieve a high level of protein synthesis. Where the amounts of RNA synthesised are relatively low (in the case of expression from a transgene), merely stabilising mRNA molecules will not necessarily lead to high levels of protein accumulation.

The ability of the double HcPro/RNA-1 transgenic lines to support the replication of both full-length and deleted forms of RNA-2 when supplied exogenously, provides the means to rapidly assess if any new RNA-2-based construct is still capable of being replicated by RNA-1. These experiments, as detailed further herein below, yield sufficient quantities of the protein of interest for an initial assessment of its biological activity to be undertaken, allowing a large number of constructs to be screened before progressing to the production of stable transgenic lines.

Overall, the system according to this invention, as principally exemplified herein with respect to the CPMV-based systems we have developed, offer a wide range of options for the expression of foreign proteins in plants. The levels of foreign gene expression achieved, though sufficient for most applications, are not as high as those reported for example according to a chloroplast transformation method known in the art (Daniell et al., 2002), with levels apparently reaching up to 46% of total soluble protein (De Cosa et al., 2001). However, expression in chloroplasts does not permit post-translational modification of proteins and it has recently been reported that protein instability could limit the expression of genes introduced into the plastid genome (Birch-Machini et al., 2004). In contrast, we have found that expression of proteins from CPMV RNA-2-based constructs allows proteins to be targeted to, and retained in, the endoplasmic reticulum. The ability to target proteins to the secretory pathway, as well as allowing complex post-translational modifications, such as glycosylation, to take place often significantly increases their stability and hence increases their levels of accumulation.

In light of the present disclosure, those skilled in the art will appreciate that this invention provides a plant gene expression system, and a method comprising (a) a first gene construct comprising a truncated RNA-2 of a bipartite virus genome carrying a foreign gene operably linked to promoter and terminator sequences; (b) a second gene construct comprising RNA-1 of said bipartite virus genome; and (c) a suppressor of gene silencing. The system of this invention contemplates induction of replication of the truncated RNA-2 by supplying a suppressor of gene silencing and an RNA-1, either exogenously or by crossing. It will be appreciated that while other bipartite plant viruses may be used in the fashion described herein, in a preferred embodiment of this invention, the first gene construct and the second gene construct are derived from Cowpea Mosaic Virus. Likewise, in a preferred embodiment of this invention, the suppressor of gene silencing is HcPro from Potato virus Y. Ideally, according to this invention, as described herein, the RNA-2 construct is truncated such that no infectious virus is produced. The method according to this invention for expressing a foreign gene in a plant cell comprises (a) introducing a first gene construct into said plant cell, said construct comprising a truncated RNA-2 of a bipartite virus genome carrying a foreign gene operatively linked to promoter and terminator sequences; (b) introducing a second gene construct into said plant cell, said construct comprising RNA-1 of said bipartite virus genome; and (c) introducing a suppressor of gene silencing into said plant cell. The first gene construct, the second gene construct and the suppressor of gene silencing are introduced into the plant cell concurrently, sequentially, or by crossing a first plant cell comprising the first gene construct with a second plant cell comprising the second gene construct. The suppressor of gene silencing, likewise, is introduced concurrently with the first gene construct, the second gene construct, or it is previously introduced into the first plant cell or the second plant cell or both.

The following definitions are provided to facilitate an understanding of the present invention.

The phrase "bipartite transgene containing viral vector" refers to a two part viral replication system for production of heterologous proteins of interest. Exemplified herein are members of the Comoviruses, which are in the picornavirus superfamily and possess non-enveloped, icosahedral capsids, and bipartite, single stranded positive sense RNA genomes. Comoviruses useful in the practice of the invention and their respective GenBank accession numbers are as follows:

CPMV RNA-1: NC_003549 (SEQ ID NO: 21)
CPMV RNA-2: NC_003550 (SEQ ID NO: 22)
RCMV RNA-1: NC_003741 (SEQ ID NO: 23)
RCMV RNA-2: NC_003738 (SEQ ID NO: 24)
BPMV RNA-1: NC_003496 (SEQ ID NO: 25)
BPMV RNA-2: NC_003495 (SEQ ID NO: 26)
CPSMV RNA-1: NC_003545 (SEQ ID NO: 27)
CPSMV RNA-2: NC_003544 (SEQ ID NO: 28)
SqMV RNA-1: NC_003799 (SEQ ID NO: 29)
SqMV RNA-2 NC_003800 (SEQ ID NO: 30)

RNA-2 sequences isolated from these other comoviruses can be truncated and operably linked to a sequence encoding a heterologous protein of interest and used in the system and method described herein.

"Plant" species of interest include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*)), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers. The skilled person will appreciate that the tropism of the viral vectors disclosed herein varies. However, determining suceptibility to such viruses is well within the purview of the skilled person. Moreover, it may be possible to alter such specificity by recombinantly expressing receptors which facilitate viral entry into a plant cell.

"Nucleic acid" or a "nucleic acid molecule" as used herein refers to any DNA or RNA molecule, either single or double stranded and, if single stranded, the molecule of its complementary sequence in either linear or circular form. In discussing nucleic acid molecules, a sequence or structure of a particular nucleic acid molecule may be described herein according to the normal convention of providing the sequence in the 5' to 3' direction. With reference to nucleic acids of the invention, the term "isolated nucleic acid" is sometimes used. This term, when applied to DNA, refers to a DNA molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or host organism.

When applied to RNA, the term "isolated nucleic acid" refers primarily to an RNA molecule encoded by an isolated DNA molecule as defined above. Alternatively, the term may refer to an RNA molecule that has been sufficiently separated from other nucleic acids with which it would be associated in its natural state (i.e., in cells or tissues). An "isolated nucleic acid" (either DNA or RNA) may further represent a molecule produced directly by biological or synthetic means and separated from other components present during its production.

The terms "percent similarity", "percent identity" and "percent homology" when referring to a particular sequence are used as set forth in the University of Wisconsin GCG software program.

The term "substantially pure" refers to a preparation comprising at least 50-60% by weight of a given material (e.g., nucleic acid, oligonucleotide, protein, etc.). More preferably, the preparation comprises at least 75% by weight, and most preferably 90-95% by weight of the given compound. Purity is measured by methods appropriate for the given compound (e.g. chromatographic methods, agarose or polyacrylamide gel electrophoresis, HPLC analysis, and the like).

A "replicon" is any genetic element, for example, a plasmid, cosmid, bacmid, plastid, phage or virus, that is capable of replication largely under its own control. A replicon may be either RNA or DNA and may be single or double stranded.

A "vector" is a replicon, such as a plasmid, cosmid, bacmid, phage or virus, to which another genetic sequence or element (either DNA or RNA) may be attached so as to bring about the replication of the attached sequence or element.

An "expression operon" refers to a nucleic acid segment that may possess transcriptional and translational control sequences, such as promoters, enhancers, translational start signals (e.g., ATG or AUG codons), polyadenylation signals, terminators, and the like, and which facilitate the expression of a polypeptide coding sequence in a host cell or organism.

The term "oligonucleotide" as used herein refers to sequences, primers and probes of the present invention, and is defined as a nucleic acid molecule comprised of two or more ribo- or deoxyribonucleotides, preferably more than three. The exact size of the oligonucleotide will depend on various factors and on the particular application and use of the oligonucleotide.

The phrase "specifically hybridize" refers to the association between two single-stranded nucleic acid molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence.

The term "probe" as used herein refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and method of use. For example, for diagnostic applications, depending on the complexity of the target sequence, the oligonucleotide probe typically contains 15-25 or more nucleotides, although it may contain fewer nucleotides. The probes herein are selected to be "substantially" complementary to different strands of a particular target nucleic acid sequence. This means that the probes must be sufficiently complementary so as to be able to "specifically hybridize" or anneal with their respective target strands under a set of pre-determined conditions. Therefore, the probe sequence need not reflect the exact complementary sequence of the target. For example, a non-complementary nucleotide fragment may be attached to the 5' or 3' end of the probe, with the remainder of the probe sequence being complementary to the target strand. Alternatively, non-complementary bases or longer sequences can be interspersed into the probe, provided that the probe sequence has sufficient complementarity with the sequence of the target nucleic acid to anneal therewith specifically.

The term "primer" as used herein refers to an oligonucleotide, either RNA or DNA, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as appropriate temperature and pH, the primer may be extended at its 3' terminus by the addition of nucleotides by the action of a polymerase or similar activity to yield a primer extension product. The primer may vary in length depending on the particular conditions and requirement of the application. For example, in diagnostic applications, the oligonucleotide primer is typically 15-25 or more nucleotides in length. The primer must be of sufficient complementarity to the desired template to prime the synthesis of the desired extension product, that is, to be able to anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product.

Polymerase chain reaction (PCR) has been described in U.S. Pat. Nos. 4,683,195, 4,800,195, and 4,965,188, the entire disclosures of which are incorporated by reference herein.

As used herein, the terms "reporter," "reporter system", "reporter gene," or "reporter gene product" shall mean an operative genetic system in which a nucleic acid comprises a gene that encodes a product that when expressed produces a reporter signal that is a readily measurable, e.g., by biological assay, immunoassay, radio immunoassay, or by calorimetric, fluorogenic, chemiluminescent or other methods. The nucleic acid may be either RNA or DNA, linear or circular, single or double stranded, antisense or sense polarity, and is operatively linked to the necessary control elements for the expression of the reporter gene product. The required control elements will vary according to the nature of the reporter system and whether the reporter gene is in the form of DNA or RNA, but may include, but not be limited to, such elements as promoters, enhancers, translational control sequences, polyA addition signals, transcriptional termination signals and the like.

The terms "transform", "transfect", "transduce", shall refer to any method or means by which a nucleic acid is introduced into a cell or host organism and may be used interchangeably to convey the same meaning. Such methods include, but are not limited to, transfection, electroporation, microinjection, PEG-fusion and the like.

The introduced nucleic acid may or may not be integrated (covalently linked) into nucleic acid of the recipient cell or organism. In bacterial, yeast, plant and mammalian cells, for example, the introduced nucleic acid may be maintained as an episomal element or independent replicon such as a plasmid. Alternatively, the introduced nucleic acid may become integrated into the nucleic acid of the recipient cell or organism and be stably maintained in that cell or organism and further passed on or inherited to progeny cells or organisms of the recipient cell or organism. Finally, the introduced nucleic acid may exist in the recipient cell or host organism only transiently.

The term "selectable marker gene" refers to a gene that when expressed confers a selectable phenotype, such as antibiotic resistance, on a transformed cell or plant. A number of "selectable marker genes" are known in the art and several antibiotic resistance markers satisfy these criteria, including those resistant to kanamycin (nptII), hygromycin B (aph IV) and gentamycin (aac3 and aacC4). Useful dominant selectable marker genes include genes encoding antibiotic resistance genes (e.g., resistance to hygromycin, kanamycin, bleomycin, G418, streptomycin or spectinomycin); and herbicide resistance genes (e.g., phosphinothricin acetyltransferase). A useful strategy for selection of transformants for herbicide resistance is described, e.g., in Vasil, Cell Culture and Somatic Cell Genetics of Plants, Vols. I III, Laboratory Procedures and Their Applications Academic Press, New York, 1984. Particularly preferred selectable marker genes for use in the present invention would genes which confer resistance to compounds such as antibiotics like kanamycin, and herbicides like glyphosate (Della-Cioppa et al., Bio/Technology 5(6), 1987, U.S. Pat. Nos. 5,463,175, 5,633,435). Other selection devices can also be implemented and would still fall within the scope of the present invention.

The term "operably linked" means that the regulatory sequences necessary for expression of the coding sequence are placed in the DNA molecule in the appropriate positions relative to the coding sequence so as to effect expression of the coding sequence. This same definition is sometimes applied to the arrangement of transcription units and other transcription control elements (e.g. enhancers) in an expression vector.

"Native" refers to a naturally occurring ("wild-type") nucleic acid sequence.

"Heterologous" sequence refers to a sequence which originates from a foreign source or species or, if from the same source, is modified from its original form.

A "coding sequence" or "coding region" refers to a nucleic acid molecule having sequence information necessary to produce a gene product, when the sequence is expressed.

"Genetic component" refers to any nucleic acid sequence or genetic element which may also be a component or part of an expression vector. Examples of genetic components include, but are not limited to promoter regions, 5' untranslated leaders or promoters, introns, genes, 3' untranslated regions or terminators, and other regulatory sequences or sequences which affect transcription or translation of one or more nucleic acid sequences.

"Complementary" refers to the natural association of nucleic acid sequences by base-pairing (A-G-T pairs with the complementary sequence T-C-A). Complementarity between two single-stranded molecules may be partial, if only some of the nucleic acids pair are complementary; or complete, if all bases pair are complementary. The degree of complementarity affects the efficiency and strength of hybridization and amplification reactions.

"Homology" refers to the level of similarity between nucleic acid or amino acid sequences in terms of percent nucleotide or amino acid positional identity, respectively, i.e., sequence similarity or identity. Homology also refers to the concept of similar functional properties among different nucleic acids or proteins.

"Promoter" refers to a nucleic acid sequence located upstream or 5' to a translational start codon of an open reading frame (or protein-coding region) of a gene and that is involved in recognition and binding of RNA polymerase II and other proteins (trans-acting transcription factors) to initiate transcription. A "plant promoter" is a native or non-native promoter that is functional in plant cells. Constitutive promoters are functional in most or all tissues of a plant throughout plant development. Tissue-, organ- or cell-specific promoters are expressed only or predominantly in a particular tissue, organ, or cell type, respectively. Rather than being expressed "specifically" in a given tissue, organ, or cell type, a promoter may display "enhanced" expression, i.e., a higher level of expression, in one part (e.g., cell type, tissue, or organ) of the plant compared to other parts of the plant. Temporally regulated promoters are functional only or predominantly during certain periods of plant development or at certain times of day, as in the case of genes associated with circadian rhythm, for example. Inducible promoters selectively express an operably linked DNA sequence in response to the presence of an endogenous or exogenous stimulus, for example by chemical compounds (chemical inducers) or in response to environmental, hormonal, chemical, and/or developmental signals. Inducible or regulated promoters include, for example, promoters regulated by light, heat, stress, flooding or drought, phytohormones, wounding, or chemicals such as ethanol, jasmonate, salicylic acid, or safeners.

When fused to heterologous DNA sequences, such promoters typically cause the fused sequence to be transcribed in a manner that is similar to that of the gene sequence with which the promoter is normally associated. Promoter fragments that include regulatory sequences can be added (for example, fused to the 5' end of, or inserted within, an active promoter having its own partial or complete regulatory sequences (Fluhr et al., Science 232:1106 1112, 1986; Ellis et al., EMBO J. 6:11 16, 1987; Strittmatter and Chua, Proc. Nat. Acad. Sci. USA 84:8986 8990, 1987; Poulsen and Chua, Mol. Gen. Genet. 214:16 23, 1988; Comai et al., Plant Mol. Biol. 15:373 381, 1991).

The 3' non-translated region of the gene constructs of the invention contain a transcriptional terminator, or an element having equivalent function, and, optionally, a polyadenylation signal, which functions in plants to cause the addition of polyadenylated nucleotides to the 3' end of the RNA. Examples of suitable 3' regions are (1) the 3' transcribed, non-translated regions containing the polyadenylation signal of *Agrobacterium* tumor-inducing (Ti) plasmid genes, such as the nopaline synthase (NOS) gene, and (2) plant genes such as the soybean storage protein genes and the small subunit of the ribulose-1,5-bisphosphate carboxylase (ssRUBISCO) gene. An example of another 3' region is that from the ssRUBISCO E9 gene from pea (European Patent Application 385,962, herein incorporated by reference in its entirety).

Typically, DNA sequences located a few hundred base pairs downstream of the polyadenylation site serve to terminate transcription. The DNA sequences are referred to herein as transcription-termination regions. The regions are required for efficient polyadenylation of transcribed messenger RNA (mRNA) and are known as 3' non-translated regions. RNA polymerase transcribes a coding DNA sequence through a site where polyadenylation occurs.

The phrase "consisting essentially of" when referring to a particular nucleotide or amino acid means a sequence having the properties of a given SEQ ID NO. For example, when used in reference to an amino acid sequence, the phrase includes the sequence per se and molecular modifications that would not affect the basic and novel characteristics of the sequence.

The phrase "suppressor of gene silencing" refers to virally encoded proteins expressed in plants that suppress PTGS. An exemplary suppressor of PTGS, the helper component-proteinase (Hc-Pro) protein encoded by a plant potyvirus, is described herein. Sequence information for HcPro is found in GeneBank accession number PVY NC_001616 and PVY HCPro: AY518295.

An "antibody" or "antibody molecule" is any immunoglobulin, including antibodies and fragments thereof, that binds to a specific antigen, such as epitopes of an apoptosis modulator protein. The term includes polyclonal, monoclonal, chimeric, and bispecific antibodies. As used herein, antibody or antibody molecule contemplates both an intact immunoglobulin molecule and an immunologically active portion of an immunoglobulin molecule such as those portions known in the art as Fab, Fab', F(ab')$_2$ and F(v).

As used herein, "transgenic plant" includes reference to a plant that comprises within its nuclear genome a heterologous polynucleotide. Generally, the heterologous polynucleotide is stably integrated within the nuclear genome such that the polynucleotide is passed on to successive generations. The heterologous polynucleotide may be integrated into the genome alone or as part of a recombinant expression cassette. "Transgenic" is used herein to include any cell, cell line, callus, tissue, plant part or plant, the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

The phrase "heterologous protein of interest" refers to any protein encoding a protein having desirable commercial, biological or therapeutic properties. Such proteins include without limitation, antibodies, hormones, cytokines, vaccines, enzymes, and coagulation factors, insulin, growth factors, etc.

EXAMPLES

Having broadly described this invention, including methods of making and using the composition of the invention, the system for gene expression in plants, and the method of bio-containment comprised therein, the following exemplary support is provided to ensure a full and complete written description of the invention, including its best mode. However, the invention as disclosed herein should not be construed as being limited to the specifics of the exemplary support. Rather, for this purpose, reference should be made to the complete patent disclosure and the appended claims.

Unless otherwise indicated, the experimental procedures utilized in the following examples are briefly as outlined below:

Plant Transformation

Plasmids pBinPS1NT, pBinPS2NT and pBinPS2NT2AGFP, containing full-length copies of CPMV RNA-1 (35S-RNA-1), RNA-2 (35S-RNA-2) and RNA-2-GFP (35S-RNA-2-GFP), respectively, in the binary transformation vector pBINPLUS (van Engelen et al., 1995) have been described previously (Liu and Lomonossoff, 2002). Construct 35S-HcPro, containing the sequence of HcPro from PVY, has been described by Cañizares et al (2004). To create the deleted versions of RNA-2, unique restriction sites were created at positions 161 (NcoI) for construct 5'3'-GFP, 512 (BspHI) for 1-GFP or 524 (BspHI) for 2-GFP using the vector pN81S2NT containing the complete sequence of RNA-2 (Liu and Lomonossoff, 2002). In all three cases a unique Stu I site was also introduced at position 3299. This allowed excision of the region of the RNA-2 between the desired initiation codon and the 3' non-coding region of RNA-2 and its replacement by a sequence encoding GFP. The resulting constructs were digested with AscI and PacI and the fragments containing the RNA-2-deleted versions flanked by the 35S promoter and nos terminator were purified and ligated into AscI-PacI-digested pBINPLUS (van Engelen et al., 1995) to give 35S-5'3'-GFP, 35S-1-GFP and 35S-2-GFP. The plasmids were maintained in *Agrobacterium tumefaciens* strain LBA4404 and/or strain C58C1. *N. benthamiana* was transformed with pBINPLUS-based plasmids using the leaf disk method (Horsch et al., 1985). Seed from kanamycin-resistant plants was germinated on plates containing 50 μg/ml kanamycin prior to planting. The presence of the appropriate transgene was confirmed by PCR analysis on extracted genomic DNA using primers specific for CPMV RNA-1, RNA-2 or HcPro. In each case, lines which showed a segregation pattern of 3:1, indicating a single locus of integration, were used for subsequent studies.

Inoculation of Plants

Infiltration with *A. tumefaciens* suspensions was carried out as previously described (Liu and Lomonossoff, 2002). Sap transmission was carried out by homogenising leaf tissue in 10 mM sodium phosphate pH7.0 followed by mechanical inoculation of test plants.

RNA Analysis

RNA was extracted from leaf tissue using the RNeasy Plant Mini Kit (Qiagen) and fractionated on formaldehyde-containing agarose gels. The RNA was transferred to positively charged nylon membranes (Roche, Indianapolis, USA) which were probed with digoxigenin-labelled probes specific for GFP or RNA-1 as described previously (Liu et al., 2004). The bound probe was detected by chemiluminescence (Roche).

Protein Analysis

Total soluble protein from leaf was extracted (Vaquero et al., 1999), quantified using a Bradford assay kit (Sigma), separated by SDS-PAGE, and stained with Coomassie blue or electrotransferred to nitrocellulose membranes. Blots were probed with polyclonal antibodies raised in rabbits against GFP (Clontech, Palo Alto, Calif., USA). Donkey anti-rabbit IgG coupled to horseradish peroxidase was used as the secondary antibody and the bands were visualised by electrochemiluminescence (ECL), and quantified using the chemiluminescence mode of a Typhoon 8600 imager (Amersham Biosciences).

Example 1

Expression of GFP from an Integrated Full-length Copy of RNA-2

*N. benthamiana* was transformed with a full-length version of RNA-2 containing GFP (35S-RNA-2-GFP; FIG. 1b), which had previously been shown to be replication-competent (Liu and Lomonossoff, 2002). This construct is based on pCP2/S-2A-GFP which makes use of the Foot-and-mouth Disease virus (FMDV) 2A catalytic peptide to achieve the release of GFP from the RNA-2-encoded polyprotein (Gopinath et al., 2000). The resulting plants were identical in appearance to non-transgenic *N. benthamiana* and showed no detectable green fluorescence under ultraviolet illumination. One line, 2NTGFP-3, was subsequently used for the experiments described below, though similar results have also been obtained with other RNA-2-GFP transgenic lines (data not shown).

Figure 2:
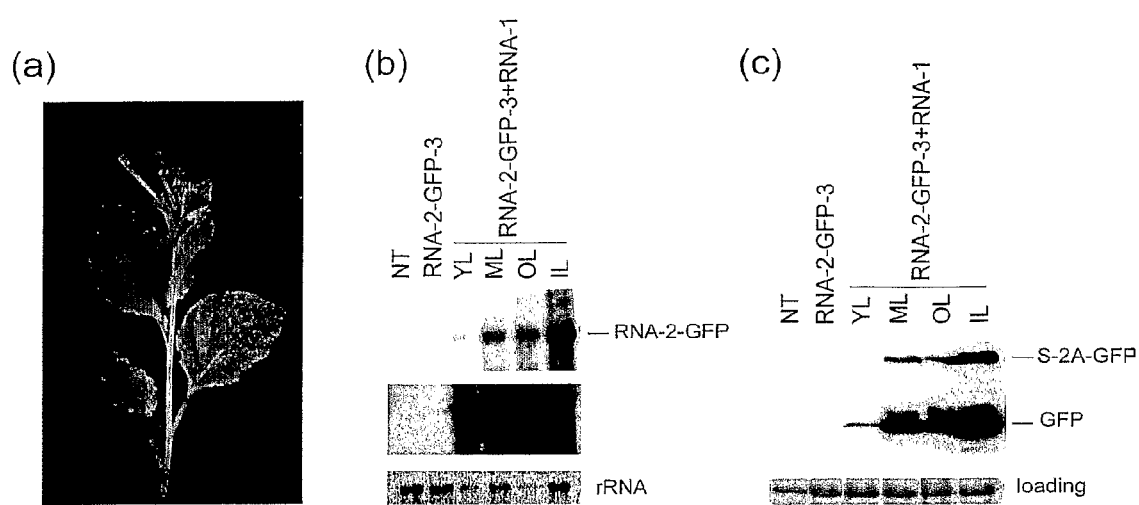

When plants from line 2NTGFP-3 were agroinoculated with 35S-RNA-1 (FIG. 1a), they all developed localised green fluorescence around area of inoculation 6 days. The fluorescence subsequently spread beyond the inoculated leaves to give patches on the stems and on the upper, uninoculated leaves (FIG. 2a). Sap extracts from the fluorescent, but not the non-fluorescent, leaves of a 2NTGFP-3 plant agroinoculated with 35S-RNA-1 gave fluorescent lesions when passaged on to cowpea plants (*Vigna unguiculata*), indicating that the RNA-2-GFP mRNA amplified from the transgene is encapsidated (data not shown).

The degree of amplification of transgene-derived RNA-2-GFP by RNA-1 was assessed by northern blot analysis of RNA extracted from entire leaves of a 2NTGFP-3 plant before and after agroinoculation with 35S-RNA-1 (FIG. 2b). A single band of the expected size for full-length RNA-2-GFP (4.3 kb) could readily be detected in samples from fluorescent inoculated lower leaves and from fluorescent upper systemic leaves (old, mature and young leaves) after RNA-1 inoculation, with the highest levels being found in the inoculated leaves (FIG. 2b, top panel). By contrast, only a faint signal could be seen even after prolonged exposure in RNA extract from tissue prior to inoculation, (FIG. 2b middle panel). The latter represents the basal level of RNA-2-GFP synthesis driven by the 35S promoter. Western blot analysis using an anti-GFP serum (FIG. 2c) showed that fluorescent leaves contained large quantities of a protein, estimated to be at least 0.6% of soluble protein, of the size expected for GFP and lesser amounts of a protein previously shown to correspond to GFP fused to the CPMV S coat protein via the FMDV 2A peptide (S-2A-GFP), the latter arising through incomplete cleavage by 2A (Gopinath et al., 2000). Only a weak GFP-specific band could be detected in samples from non-inoculated 2NTGFP-3 plants. Using a purified GFP standard it was estimated, that from the total soluble proteins extracted from a whole leaf, there was an enhancement in the expression of GFP in leaves agroinoculated with RNA-1 of at least 60-fold compared with the levels prior to inoculation.

Figure 4:
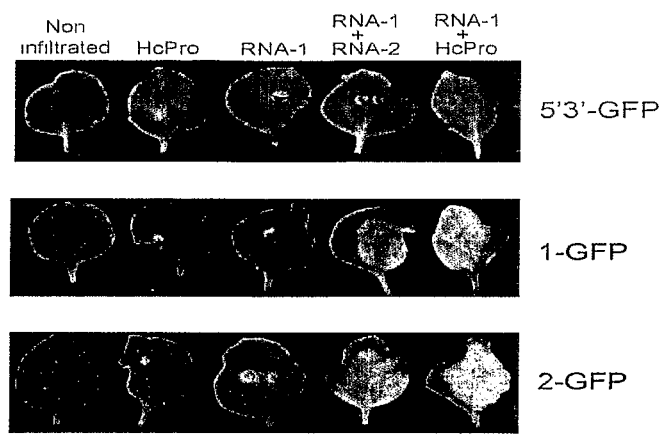
Figure 5:
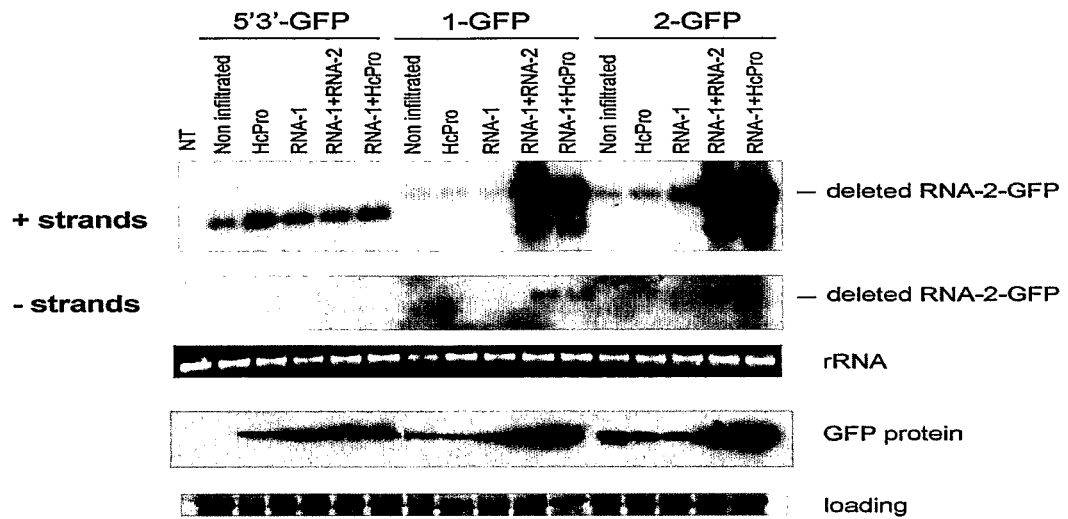

To determine whether RNA-2-GFP can be amplified by supplying RNA-1 by crossing, pollen from 2NT-GFP-3 plants was used to fertilise plants from line 1NT-11F2, a line identified by backcrossing as being homozygous for RNA-1 (Liu et al. 2004). Eight out of 22 kanamycin-resistant plants recovered from this cross (designated line 7-1) showed very mild symptoms and green fluorescence under ultraviolet light, this being more intense on older leaves (FIG. 3a). The fact that only a proportion of plants were fluorescent was expected since no attempt was made to prevent self-pollination of the RNA-1-containing parent. The correlation of visible fluorescence with the presence of both CPMV genome segments was confirmed by PCR analysis of genomic DNA extracted from the plants. In addition, the fluorescent phenotype was heritable through subsequent generations of plants.

Northern blot analysis of RNA extracted both from fluorescent (old, mature and young leaves) and non-fluorescent leaves (the youngest ones) from a 7-1 plant showed the presence of a band corresponding to RNA-2-GFP in fluorescent leaves, the signal being most intense in the sample from old leaves (FIG. 3*b*). No such band was found in RNA extracted from non-transgenic plants or plants transgenic for RNA-1 alone. Western blot analysis using anti-GFP serum revealed the presence of GFP in extracts from all the visibly fluorescent leaves, the intensity of the signal increasing with the age of the leaf (FIG. 3*c*). A similar pattern was found when samples from other plants transgenic for both RNA-2-GFP and RNA-1 were analysed. We estimated that the increase in expression levels of GFP after crossing was of at least 100-fold as compared with the level in the 2NT-GFP-3 parent and represented approximately 1% of total soluble protein. No band corresponding to GFP was detectable in western blots of extracts from non-transgenic plants or plants transgenic for RNA-1 alone (FIG. 3*c*). It was also possible to passage the infection on to cowpea plants using sap from fluorescent leaves, indicating that fully competent virus particles were being produced since free (unencapsidated) RNA does not survive this procedure.

Example 2

Deleted Versions of RNA-2 Carrying GFP can be Replicated by Exogenously Supplied RNA-1 as Long as a Suppressor of Silencing is Present To investigate if it is possible to express a foreign protein from deleted versions of RNA-2, which would produce defective virus unable to spread in the environment, a series of expression cassettes were created. In these the sequence of GFP was flanked by those sequences from RNA-2 previously shown to be necessary for its replication by RNA-1 (Holness et al. 1989; Rohll et al., 1993; van Bokhoven et al. 1993). To this end, unique restriction sites were created around each of the first 3 methionine codons in the RNA-2 open reading frame (ORF) and immediately upstream of the 3' untranslated region (UTR). This allowed excision of the region of the RNA-2 between the desired initiation codon and the 3' UTR of RNA-2 and its replacement by the sequence encoding GFP. The cloning procedure resulted in the sequence of GFP being extended by 12 amino acids at its C-terminus. The RNA-2-GFP-specific sequences were inserted into pBINPLUS to give constructs 35S-5'3'-GFP (in which GFP translation is initiated at the first in-frame AUG of RNA-2 at position 161), 35S-1-GFP (GFP translation initiating at the second in-phase AUG at 512) and 35S-2-GFP (initiation at the AUG at 524; FIG. 1*b*). The three different constructs were made as it has previously been shown that part of the coding region downstream of AUG161, as well as the 5' UTR is required for efficient replication of RNA-2 by the RNA-1-encoded replicase (Rohll et al., 1993; van Bokhoven et al., 1993). In each case, only the 3' UTR was included downstream of the GFP sequence as the signals for replication at the 3' end of RNA-2 lie exclusively in this region (Rohll et al., 1993). Agroinfiltration of the various constructs into *N. benthamiana* leaves showed that all were capable of expression GFP in a transient assay (data not shown). The constructs were used to transform *N. benthamiana* and lines of plants containing each construct were regenerated. The lines transgenic for 1-GFP and 2-GFP were phenotypically normal and showed no fluorescence under ultraviolet light. The leaves of the 5'3'-GFP transgenic lines, while also phenotypically normal, showed a weak background fluorescent under ultraviolet light which was particularly evident around the petiole (5'3' panels in FIG. 4).

Agroinfiltration of leaves of *N. benthamiana* lines transgenic for 5'3'-GFP, 1-GFP and 2-GFP with 35S-RNA-1 did not lead to an increase of the GFP fluorescence indicating that no replication of the deleted RNA-2 had occurred (FIG. 4, Panels marked RNA-1). This was not unexpected since it has previously been shown that RNA-1 replication triggers efficient post-transcriptional gene silencing (PTGS) which drastically limits the amount of replicase available for amplifying RNA-2-based constructs (Liu et al., 2004). However, in transient assays this effect can be relieved by the presence of a suppressor of silencing. During a natural infection this suppressor function is provided by the C-terminal portion of the S coat protein which is encoded by RNA-2 (Liu et al., 2004; Cañizares et al., 2004), a region which is absent for the deleted RNA-2 constructs. To determine if supplying full-length RNA-2, which would contain the missing suppressor sequence, could lead to enhanced levels of GFP expression, leaves transgenic for the deleted RNA-2-GFP constructs were co-infiltrated with 35S-RNA-1 and 35S-RNA-2. This resulted in an increase in the levels of fluorescence in the case of the 1-GFP and 2-GFP transgenic plants, but not in the case of those transgenic for 5'3'-GFP (FIG. 4, Panels marked RNA-1+RNA-2). This result indicates that the polymerase encoded by RNA-1 is only able to replicate the transgene-derived versions of RNA-2 when sequences downstream of AUG161, as well as the 5' UTR, are present (Rohll et al., 1993; van Bokhoven et al., 1993). To determine whether similar expression levels could be obtained using a heterologous suppressor of silencing, leaves from plants transgenic for the various constructs were co-infiltrated with 35S-RNA-1 plus the strong suppressor of RNA silencing, HcPro from Potato virus Y (PVY; Hamilton et al., 2002) under the control of the 35S promoter (35S-HcPro). In these assays, a very strong increase in GFP fluorescence was observed in leaves from the 1-GFP and 2-GFP transgenic plants while, as previously, no enhancement was found in case of those transgenic for 5'3'-GFP (FIG. 4, Panels RNA-1+HcPro). The enhancement required the presence of both the suppressor and RNA-1, no enhancement being found in any of the leaves infiltrated with either RNA-1 or 35S-HcPro alone. Taken together, the results strongly suggest that enhanced GFP expression requires replication of the transgene-derived mRNA which can occur only when both RNA-1 and a suppressor of silencing are simultaneously present.

To confirm that this increase in the expression levels of GFP is, indeed, due to the replication of mRNA derived from the deleted RNA-2 GFP constructs, the levels of both plus- and minus-strand GFP-specific RNA in the infiltrated patches of the leaves shown in FIG. 4 were determined. See FIG. 5. In the case of the leaves from plants transformed with 5'3'-GFP, a constant level of plus-strands was observed irrespective of treatment, a result consistent with the lack of enhancement of fluorescence seen in FIG. 4. Moreover, no minus-strands could be detected, again consistent with the failure of 5'3'-GFP-derived mRNA to be replicated. In contrast, in the case of leaves transgenic for 1-GFP and 2-GFP, greatly enhanced levels of plus-strands were seen after infiltration with 35S-

RNA-1 plus either 35S-RNA-2 or 35S-HcPro and minus strands could also be detected albeit at a relatively low level. These results confirm that mRNA from the RNA-2-deleted constructs 1-GFP and 2-GFP, but not 5'3'-GFP can be replicated by RNA-1 when a suppressor of silencing is also present. Western blot analysis using an anti-GFP serum confirmed that the increase in GFP fluorescence seen in FIG. 4 and the GFP mRNA levels in FIG. 5 are paralleled by an increase in protein expression. The western blots also showed only a single GFP-specific band for each sample, the size being that expected for GFP with a 12 amino acid extension at its C-terminus. Though this was anticipated for 5'3'-GFP, where translation would initiate exclusively at the AUG at position 161, it was somewhat unexpected in the case of 1-GFP and 2-GFP, where it was anticipated that initiation would occur both at AUG 161 and at either or both of the AUGs at positions 512 and 524. Initiation at AUG161 in constructs 1- and 2-GFP would result in a GFP molecule bearing an N-terminal extension of approximately 14 kDa. The fact that this larger protein was not observed indicates that the AUG at position 161 is rarely, if ever, used in constructs 1-GFP and 2-GFP.

Example 3

Deleted RNA-2-GFP Molecules can Replicate in *N. benthamiana* Lines Transgenic for both RNA-1 and HcPro To determine whether a suppressor expressed from a transgene can eliminate the amplicon effect of RNA-1, *N. benthamiana* was transformed with the HcPro sequence from PVY. A number of lines were regenerated and one, line HcPro-11, was selected for further crossing. To produce plants containing transgenes for both RNA-1 and HcPro, line HcPro-11 was crossed with 11F2 and those progeny (11F2xHcPro) containing both transgenes were identified by PCR analysis of genomic DNA. While 11F2 plants were phenotypically normal, both the HcPro single transgenic plants and the 11F2xHcPro double transgenic plants consistently showed a delayed rate growth. Northern blot analysis with probes specific for either HcPro plus strands or RNA-1 minus strands confirmed that HcPro is expressed in these plants and that this expression led to an increased level of RNA-1 minus strands (data not shown). To confirm that the presence of HcPro eliminates the RNA-1 amplicon effect, 11F2xHcPro plants were agroinfiltrated with either 35S-RNA-2 or 35S-RNA-2-GFP. In contrast to the situation with 11F2 plants, a productive infection resulted in both cases, with inoculation with RNA-2-GFP giving rise to visible fluorescence on the inoculated leaves and a systemic infection (data not shown).

Figure 6:
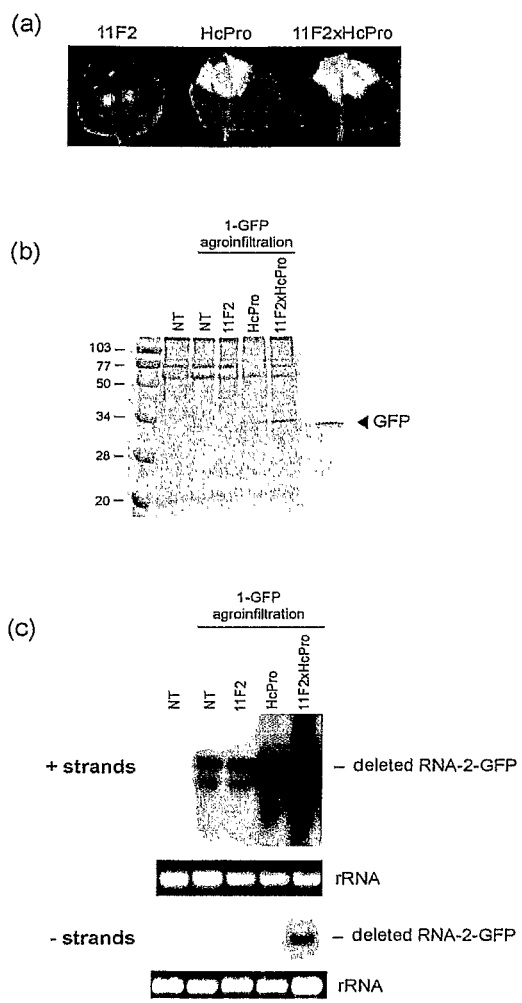

To determine whether plants transgenic for both RNA-1 and HcPro could increase the level of GFP expression from defective versions of RNA-2, leaves from 11F2, HcPro-11 and 11F2xHcPro plants were agroinfiltrated with the deleted RNA-2 construct, 35S-1-GFP. While the fluorescence in 11F2 leaves infiltrated with 35S-1-GFP had disappeared by 6 days post-inoculation (dpi), in both the HcPro-11 and 11F2xHcPro transgenic plants, the fluorescence from the infiltrated 35S-1-GFP construct was very strong and lasted at a similar strength for at least 15 dpi (FIG. 6a). Coomassie staining of an SDS-polyacrylamide gel of total protein extracted from the fluorescent regions indicated that GFP levels reached about 3% of the total soluble protein in both the HcPro-11 and 11F2xHcPro plants (FIG. 6b). This indicates that replication of a defective RNA-2 molecule is not necessary to obtain high levels of expression in a transient situation provided a suppressor of silencing is present. As before, the size of the band corresponded to that expected of GFP without a 14 kDa N-terminal extension, the slightly slower migration compared with the GFP standard most likely reflecting the 12 amino acid extension at the C-terminus.

To determine the levels of 1-GFP-specific RNA in the infiltrated leaves, RNA was extracted from non-transgenic and 11F2 plants at 4 dpi (before the fluorescence had disappeared) and from HcPro-11 and 11F2xHcPro plants at 8 dpi. Northern blot analysis using a probe specific for GFP plus strands showed that leaf tissue with high levels of GFP fluorescence (from the HcPro-11 and 11F2xHcPro plants) contained a correspondingly high level of 1-GFP positive strands. Northern blot analysis using a probe specific for 1-GFP minus strands showed the presence of such strands only in the RNA extracted from the double transgenic 11F2xHcPro plants, confirming that the presence of both the suppressor and RNA-1 is necessary for 1-GFP replication (FIG. 6c).

Figure 7:
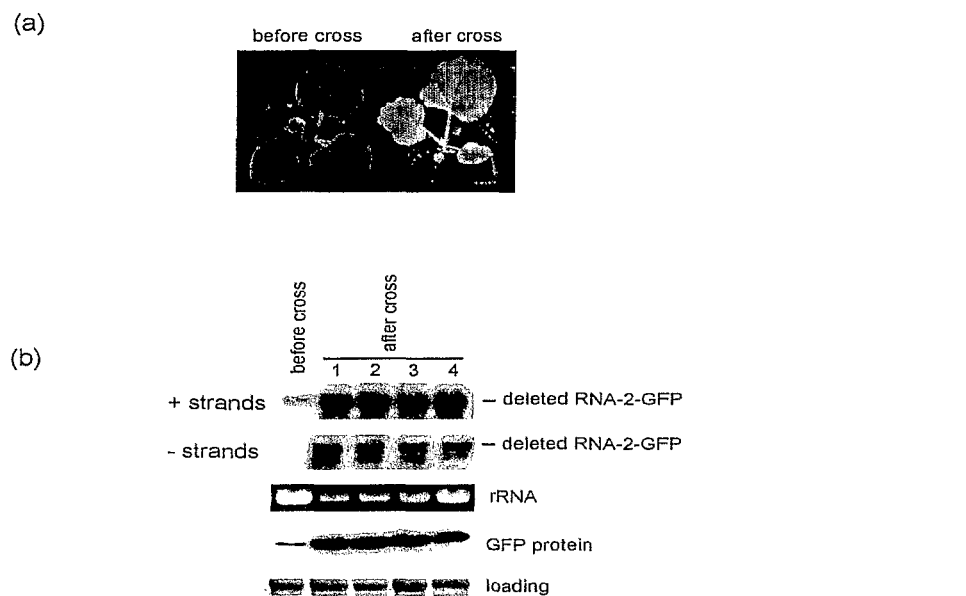

The above results show that a deleted version of RNA-2 (1-GFP) can be replicated in a transient assay using RNA-1/HcPro double transgenic host plants. To determine if this approach can be used in a constitutive format, plants transgenic for 1-GFP were crossed with the double transgenic line 11F2xHcPro. After the cross, a proportion of the progeny showed fluorescence under ultraviolet light (FIG. 7a). PCR analysis confirmed that only those plants transgenic for all three transgenes were fluorescent. When only the HcPro and 1-GFP transgenes were present, no fluorescence was seen, a result which contrasts with that found in the transient assay. Overall, the data indicate that in the transgenic situation, replication of 1-GFP by RNA-1 has to occur for fluorescence to be visible. Northern blot analysis of RNA extracted from the fluorescent triple transgenic plants revealed the presence of both plus- and minus-strand GFP-specific RNA (FIG. 7b), confirming that replication of 1-GFP had occurred. From western blot analysis we estimate an increase in the expression levels of the GFP of at least 10-fold after the cross with 11F2xHcPro plants (FIG. 7b, bottom).

Example 4

Creation of Deleted Version of CPMV RNA-2

Plasmid pN81S2NT, containing a full-length copy of CPMV RNA-2 inserted between a CaMV 35S promoter and a nos terminator (Liu and Lomonossoff, 2002) was digested with AscI and PacI. The fragment containing the 35S promoter, full length RNA-2 and the nos terminator was transferred to plasmid pM81W (Liu and Lomonossoff, in preparation) to give pM81W-S2NT.

Plasmid pM81W-S2NT was subject to mutagenesis with four primers (nucleotide changes shown in lower case):

M005:
(SEQ ID NO: 1)
CTG CCC AAA TTT Gtc ATG aAA AGC ATT ATG AGC CG;
nucleotides 497-531 of RNA-2) to introduce a BspHI site around AUG 512.

M011:
(SEQ ID NO: 2)
GCT ACT GCT GCT TAg gcC TGG TTT CAT TAA AT;
nucleotides 3287-3318 of RNA-2) to introduce a StuI site after UAA 3299.

-continued

M012:
(SEQ ID NO: 3)
GGA TTT TGG TtA TGA GAT TAT C
to eliminate BspHI site in ColE1 region
of plasmid.

M013:
(SEQ ID NO: 4)
GGG TTA TTG TCT tAT GAG CGG ATA C
to eliminate BspHI site in M13 ori region
of plasmid.

The resulting plasmid was termed pM81B-S2NT1. Digestion with BspHI and StuI allows the entire coding region of RNA-2 downstream of AUG512 to excised (as two fragments) and replaced another sequence of choice. This must have a BspHI-compatible 5' end and a 3' blunt end. Using this approach it is possible to create a construct equivalent to 1-GFP but with the sequence of GFP replaced by that of the desired sequence.

To transfer the deleted RNA-2 containing the introduced gene, the pM81B-S2NT1 derivative is digested with AscI and PacI and the appropriate fragment isolated. This is then ligated into similarly digested pBINPLUS and the resulting plasmids used to transform *Agrobacterium tumefaciens*.

To demonstrate the use of this approach, sequences encoding either human glutamic acid decarboxylase (hGAD65/67) or the HIV-1 nef protein were inserted between the BspHI and StuI of pM81B-S2NT1. When the resultant constructs were agroinfiltrated into the leaves of RNA-1/HcPro double transgenic host plants, high levels of the appropriate mRNA could be detected by northern blot analysis. In the case of the hGAD65/67, protein expression was estimated to be approximately 1% total soluble protein.

Example 5

The use of CPMV-based Vectors to Produce Antigens in Plants

The core antigen of hepatitis B virus HBcAg is the product of the HBV C-gene. During HBV replication and expression in heterologous systems including *Escherichia coli*, (Burrell et al., 1979), yeast (Clarke et al., 1987), insect cells (Hildich et al., 1990) and *Xenopus oocytes* (Zhou and Standring, 1992), the protein self-assembles to form the subviral nucleocapsid particles (diameter 30-32 nm) which package the viral polymerase and pregenomic RNA. HBcAg has been shown to be capable of displaying foreign peptides at several different positions on their surface (Schodel et al., 1992; Borisova et al., 1993, 1996). HBcAg-based chimaeras have been developed as experimental vaccines against a number of diseases (Tindle et al., 1994; Boulter et al., 1995), including HBV itself (Chen et al., 2004).

In earlier work, we demonstrate that full-length CPMV RNA-based vectors can be used to produce assembled HBcAg particles in plants. See Mechtcheriakova et al. J. Virol. Meth. 131, 10-15 (2006). To this end, the protein was expressed from vectors based on Cowpea mosaic virus (CPMV). For the construction of a CPMV-based expression vector, the HBV C-gene was PCR-amplified and fused in-frame with the open reading frame of RNA-2 in pBinP-NS-1 (Liu et al., 2005) to give the construct pBinPS2NT/core (FIG. 1B). Release of free HBcAg is designed to be mediated by the action of the 2A catalytic peptide from foot-and-mouth disease virus (FMDV) (Gopinath et al., 2000).

The designed HBcAg-RNA-2 fusion was agroinfilrated in cowpea together with a full-length copy of CPMV RNA-1 (Liu and Lomonossoff, 2002). Agroinfiltrated plants did not develop any symptoms by 18 days post-inoculation (dpi), but the sap from these plants agroinfiltrated in other cowpea plants induced infection. However, no systemic symptoms developed even by 30 dpi. RT-PCR analysis of RNA extracted from the primary leaves revealed that insert had been retained.

To determine whether HBcAg was produced in the infected plant tissue, samples from virus-infected leaves were analysed by Western blot with anti-HBcAg polyclonal antibody raised in rabbits (Biomeda). Little or no HBcAg was detected in extracts from agroinfiltrated leaves. To examine whether it was possible to enrich for assembled HBcAg particles expressed in cowpeas, particulate material was sedimented from the extract by high-speed centrifugation. The resulting pellet revealed the presence of a prominent band corresponding in size to that of yeast-derived HBcAg (See FIG. 2 of Mechtcheriakova et al.). The fact that the plant-expressed protein can be sedimented strongly suggested it was in a highly aggregated state and most probably in the form of core particles. In addition, the high-speed fraction contained a band corresponding in size to a dimer of HBcAg, an observation consistent with the dimers being an important intermediate in the assembly of core particles (Zhou and Standring, 1992). This fraction also contained some additional high molecular weight material which may represent further aggregation of the HBcAg protein. Alternatively, these may represent the products of incomplete cleavage by the 2A catalytic peptide (Gopinath et al., 2000), resulting in the production of an S-2A-HBcAg fusion protein. A Coomassie blue-stained gel of the high speed pellet fraction showed that it contains essentially only the HBcAg proteins and the CPMV coat proteins (data not shown). This was anticipated since any CPMV particles produced during the infection will co-sediment with assembled HBcAg. We estimate that 10-20% by weight of the protein in the high speed pellet fraction consisted of aggregated HBcAg, the rest of the material being mostly CPMV particles. Overall, it is estimated that the total yield of the semi-purified HBcAg particles was approximately 10 microgram per gram of cowpea leaf fresh weight.

Immunosorbent electron microscopy with the anti-HBcAg polyclonal antiserum revealed the presence of particles with the characteristic appearance of assembled HBcAg particles (FIG. 3, Panel C in Mechtcheriakova et al.) high-speed pellet. The results demonstrate that HBcAg can be expressed successfully from CPMV-based vectors and that the protein retains its ability to self-assemble.

Time taken from the creation of the required constructs to the detection of assembled particles in plant extracts is only a matter of weeks. This suggests that it is possible to produce and screen a significant number of HBcAg-based chimaeras in relatively short period.

The HBcAg variant which we have expressed is the full-length form of the protein which includes the C-terminal arginine-rich tail containing two nuclear localization signals (Pumpens and Grens, 1999). It is known that truncated HBcAg lacking this tail can also be assembled into particles and it may also be possible to use this form to produce chimaeras in plants.

CPMV vector used in the experiments can be propagated in cowpea, an edible plant, eliminating further purification of the antigen. It has already been shown that CPMV-based chimaeras, purified in a manner similar to that used for the enrichment of HBcAg particles reported here, can be injected into a variety of experimental animals without causing harm (Lomonossoff and Hamilton, 1999). Thus it is anticipated that the semi-purified HBcAg preparations produced in cowpea plants, despite containing CPMV particles, could be suitable for assessment of their immunogenic properties. However, the presence of two types of particle, HBcAg and CPMV, in the preparations might complicate the interpretation of the data. Furthermore, the CPMV particles within the preparation will be infectious and handling the preparations runs the potential risk of spreading the modified virus. Physical separation of the HBcAg and CPMV particles is impractical owing to their similar size and sendimentation properties. Therefore, use of a deleted version of CPMV RNA-2 according to this invention for the expression of HBcAg provides distinct advantages over prior art approaches in terms of biocontainment as well as simplifying the immunological analysis of the core particles.

Example 6

Use of CPMV RNA-2 to Express Small Immunogenic Proteins (SIPs) in Plants

Transmissible gastroenteritis virus (TGEV) is a coronavirus which infects pigs via the enteric tract. Newborn animals are protected by passive immunisation with antibodies in milk. Oral administration of antibodies may be an effective therapy if antibodies can be produced at sufficiently low cost. A monoclonal antibody, 6A.C3 has been shown to neutralize all isolates of porcine TGEV and related coronaviruses from other species by binding to Spike protein of TGEV (Suñe et al., 1990; Gebauer et al., 1991). No escape mutants have ever been isolated and the antibody can neutralise TGEV when expressed in milk of transgenic mice (Castilla et al., 1997, 1998; Sola et al., 1998).

To investigate the potential of antibody derivatives based on 6A.C3 to provide passive protection against enteric infections when supplied orally in crude plant extracts, we created a Small Immune Protein (SIP; Li et al., 1997). This consists of a single chain antibody (scFv) derived from 6A.C3 linked to the ϵ-CH4 domain from human IgE to give 6aC3-ϵSIP. The sequence encoding the ϵSIP was flanked by the leader peptide from the original murine antibody at its N-terminus and an endoplasmic reticulum (ER) retention signal (HDEL) at its C-terminus to allow the expressed protein to be directed to, and retained within, the endoplasmic reticulum. The sequence encoding the ϵSIP was inserted into a full-length CPMV RNA-2-based vector and the construct was used to inoculate cowpea plants in the presence of RNA-1. Western blot analysis of samples from cowpea tissue infected with constructs revealed the presence of SIP molecules which retained their ability to dimerize. Analysis of crude sap extracts revealed that the plant-expressed ϵSIP molecules could bind to and neutralize TGEV in tissue culture. Oral administration of crude sap from SIP-expressing plant tissue to 2 day-old piglets demonstrated that those extracts which showed the highest levels of in vitro neutralisation could also provide in vivo protection against challenge with TGEV.

The above results showed that SIP molecules expressed in plants can be used to combat enteric infections. However, the sap extracts contained large quantities of infectious CPMV particles and their presence could allow the unwanted spread of CPMV-based infection in plants. Thus it would be advantageous to express the SIP molecules from deleted version of RNA-2 according to the present invention.

Example 7

Construction of a Deleted Version of RCMV RNA-2

Figure 8:
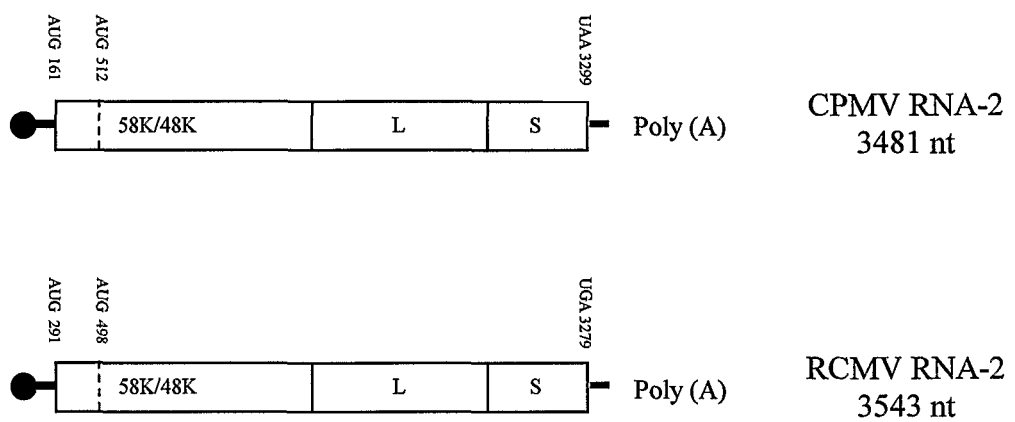

The sequences of both RNA-2 and RNA-1 of RCMV are known (Shanks et al., 1986; Shanks and Lomonossoff, 1992). Sequence comparisons showed that the organization and expression strategy of both RNAs is very similar to those of their CPMV counterparts (Shanks et al., 1989; 1996; Lin et al., 2000). Thus the information provided herein for construction of a deleted version of CPMV RNA-2 can also be applied to RCMV RNA-2. FIG. 8 shows the genome organization of CPMV and RCMV RNA-2. In both cases the RNA is polyadenylated and has a small protein (VPg) linked to its 5' end. The $1^{st}$ two in-phase AUG codons are indicated. The 58/48K proteins are derived from initiation at the first two AUGs. The regions coding for the large (L) and small (S) coat proteins are also indicated.

Specifically, to construct a deleted version of CPMV RNA-2 which could be effectively replicated by RNA-1, we made use of the information generated by Rohll et al. (1993). In these experiments, the ability of deleted versions of RNA-2 to be replicated in protoplasts by co-inoculated RNA-1 was determined. These experiments showed that it was essential to include sequences downstream of the first AUG (161) to achieve efficient replication. Though exactly the extent of the essential sequence was not mapped precisely, if the sequence up to the second AUG (512) was included, replication was restored. All the 3' sequences necessary for replication are within the 3' UTR. Thus the construct pM81B-S2NT1 was designed to allow replacement of the CPMV RNA-2 coding region between nucleotides 512 and 3299 with a gene of interest. This was done by creating a BspHI at position 512 and a StuI site at 3299.

According to this strategy, the methodology is to create restriction enzyme sites at or around the second AUG (498) and the UGA (3279). This allows excision of the RCMV RNA-2 coding region. One would not necessarily use the same enzymes and it may not be necessary to use the AUG at 498—the coding sequence inserted therein could provide the initiation codon. Insertion of a polylinker to facilitate cloning is also well within the skill of those working in this area.

Example 8

Expression of a Monoclonal Antibody Using CPMV

To assess the efficiency of the system to produce heteromultimeric proteins, the CPMV RNA-based vector was used to produce a monoclonal antibody. The selected antibody, named C5-1, is a murine IgG1 specifically binding human immunoglobulin constant region, and it is used in blood group typing analysis.

The genes encoding heavy and light chain of the C5-1 monoclonal antibody were cloned in the CPMV based vector as follows. The light chain was amplified with primers ApaI-LC(C5-1).1c and LC(C5-1)-StuI.r from R612, a binary plasmid containing the light and the heavy chain of C5-1. In parallel, an ER-retained form of the light chain was amplified with primers ApaI-LC(C5-1).1c and LC(C5-1)-SEKDEL-StuI.r. Similarly, the heavy chain of the antibody was amplified in original and SEKDEL forms using primers ApaI-HC(C5-1).1c and HC(C5-1)-StuI.r and ApaI-HC(C5-1).1c and HC(C5-1)-SEKDEL-StuI.r, respectively.

The four amplified fragments were digested with ApaI and StuI, and cloned into pCP2S-GFP plasmid (Gopinath et al., Virology 267 (2000) 159-173) previously digested with the same enzymes. The resulting plasmids are shown in FIG. 9. The plasmids were transfected into *Agrobacterium tumefaciens* strain AGL1.

Transient expression studies in *Nicotiana benthamiana* were essentially performed as described in Liu and Lomonossoff (Journal of Virological Methods 105 (2002) 343-348) with the following modifications. For the expression of C5-1 antibodies, a mixture of four *Agrobacteria* strains was inoculated. The first bacteria contained the plasmid containing RNA1 under the control of a truncated 35S promoter (pBinPS1NT), the second bacteria contained the plasmid encoding RNA2/LC (820 or 821), the third contained the plasmid encoding RNA2/HC (822 or 823) and a fourth bacteria contained a binary plasmid containing the HcPro suppressor of silencing from the Potato Virus Y under the control of the 35S promoter (Brigneti et al., EMBO 17 (1998) 6739-6746). After inoculation, the plants were returned to the greenhouse for 7 days before extraction and analysis.

Immunological analysis of C5-1 production was performed as follows. Inoculated leaves were ground in extraction buffer (50 mM Tris pH7.4, 150 mM NaCl, 0.1% Triton X-100, 1 mM PMSF, 10 µM chymostatin). After centrifugation, protein content of the supernatant was determined according to Bradford using the dye reagent concentrate from Bio-Rad with bovine serum albumin as standard. Five micrograms of soluble proteins were boiled in non-reducing sample loading buffer and separated by SDS-PAGE, and blotted onto a PVDF membrane using standard protocols (see Protein Methods (Bollag D M, Rozycki M D, Edelstein S J Eds., Wiley-Liss-Publishers, $2^{nd}$ edition (1996)) for standards electrophoresis and protein blotting protocols). Immunological detection of the antibody was performed using polyclonal peroxidase-conjugated goat anti-mouse IgG (H+L) immunoglobulins (Jackson Immunoresearch, #115-035-146). BM chemiluminescence Peroxidase substrate (Roche #1 500 708) was used for chemiluminescent detection following manufacturer protocol. FIG. 10 presents an immunological analysis of transient C5-1 expression in *Nicotiana benthamiana* after inoculation of CPMV RNA-based vectors.

```
Oligonucleotide primers sequence
ApaI-LC (C5-1).1c (36-mers)
                                              (SEQ ID NO: 5)
5'-TGTCGGGCCCATGGTTTTCACACCTCAGATACTTGG-3'

LC (C5-1)-StuI.r (26-mers)
                                              (SEQ ID NO: 6)
5'-CCTCTAACACTCATTCCTGTTGAAGC-3'

LC (C5-1)-SEKDEL-StuI.r (44-mers)
                                              (SEQ ID NO: 7)
5'-CCTCTAAAGTTCATCCTTCTCAGAACACTCATTCCTGTTGAAGC-3'

ApaI-HC (C5-1)-1c (32-mers)
                                              (SEQ ID NO: 8)
5'-AGTCGGGCCCATGGCTTGGGTGTGGACCTTGC-3'

HC (C5-1)-StuI.r (23-mers)
                                              (SEQ ID NO: 9)
5'-CCTTCATTTACCAGGAGAGTGGG-3'

HC (C5-1)-SEKDEL-StuI.r (41-mers)
                                              (SEQ ID NO: 10)
5'-CCTTCAAAGTTCATCCTTCTCAGATTTACCAGGAGAGTGGG-3'
```

Example 9

Expression of a Monoclonal Antibody Using a Truncated CPMV RNA2-based Vector

The genes encoding heavy and light chain of the C5-1 monoclonal antibody can be assembled with a deleted CPMV-based vector using a PCR-based ligation method as described by Darveau et al., Methods in Neurosciences 26 (1995)77-85). The open reading frames coding for the antibody heavy and light chain are fused in phase with viral ORF between AUG512 and 3'UTR as in FIG. 11.

Figure 12:
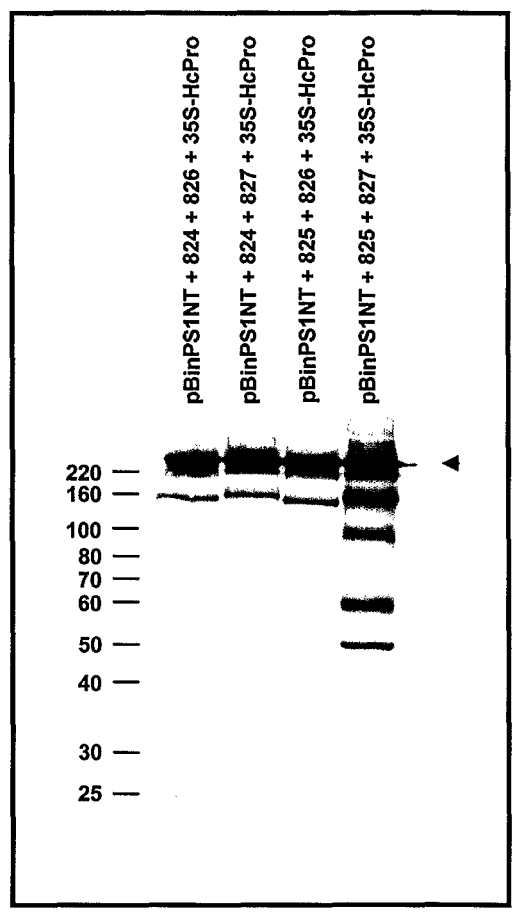

The plasmids are transfected into *Agrobacterium tumefaciens* strain AGL1, and the transient expression is performed as described in Example 8. Immunological analysis of C5-1 production was performed as follows. Inoculated leaves were ground in extraction buffer (50 mM Tris pH7.4, 150 mM NaCl, 0.1% Triton X-100, 1 mM PMSF, 10 µM chymostatin). After centrifugation, protein content of the supernatant was determined according to Bradford using the dye reagent concentrate from Bio-Rad with bovine serum albumin as standard. Five micrograms of soluble proteins were boiled in non-reducing sample loading buffer and separated by SDS-PAGE, and blotted onto a PVDF membrane using standard protocols (see Protein Methods (Bollag D M, Rozycki M D, Edelstein S J Eds., Wiley-Liss-Publishers, $2^{nd}$ edition (1996)) for standards electrophoresis and protein blotting protocols). Immunological detection of the antibody was performed using polyclonal peroxidase-conjugated goat anti-mouse IgG (H+L) immunoglobulins (Jackson Immunoresearch, #115-035-146). BM chemiluminescence Peroxidase substrate (Roche #1 500 708) was used for chemiluminescent detection following manufacturer protocol. FIG. 12 depicts the results of immunological analysis of transient C5-1 expression in *Nicotiana benthamiana* after inoculation of CPMV RNA-based vectors.

Example 10

Expression of a Monoclonal Antibody Using a Truncated RCMV RNA2-based Vector

The genes encoding heavy and light chain of the C5-1 monoclonal antibody can be assembled with a deleted RCMV-based vector using a PCR-based ligation method (a PCR-based ligation protocol is described by Darveau et al., Methods in Neurosciences 26 (1995)77-85) with the following primers:

```
820-2745.c:
5'-GTAACGCCAGGGTTTTCCCAG-3'                              (SEQ ID NO: 11)

35S/RCMV5'.r:
5'-CAAAATTTTATATAAAAATTTTAATACCTCTCCAAATGAAATGAAGAAG-3' (SEQ ID NO: 12)

RCMV5'.1c:
5'-TATTAAAATTTTTATATAAAATTTTG-3'                         (SEQ ID NO: 13)

RCMV5'/C5-1 LC.r:
5'-CAAGTATCTGAGGTGTGAAAACCATGGGCCCTTTCCCAAGATATTCTAGCCCAG-3' (SEQ ID NO: 14)
```

-continued

```
C5-1 LC.1c:
5'-ATGGTTTTCACACCTCAGATACTTG-3'                                          (SEQ ID NO: 15)

C5-1 LC/StuI.r:
5'-CCTCTAACACTCATTCCTGTTGAAGC-3'                                         (SEQ ID NO: 16)

C5-1 LC/RCMV3'.r:
5'-CTATACCATGCAACATGAGACCAGGCCTCTAACACTCATTCCTGTTGAAGCTC-3'              (SEQ ID NO: 17)

RCMV3'.c:
5'-GGTCTCATGTTGCATGGTATAG-3'                                             (SEQ ID NO: 18)

RCMV3'/polyA/EcoRI.r:
5'-AGAAGAATTCTTTTTTTTTTTTTTTTAATAAACATAACTTTAAAVCAATACCACAA3'            (SEQ ID NO: 19)

ApaI-HC (C5-1)-1c:
5'-AGTCGGGCCCATGGCTTGGGTGTGGACCTTGC-3'                                   (SEQ ID NO: 8)

HC (C5-1)-StuI.r:
5'-CCTTCATTTACCAGGAGAGTGGG-3'                                            (SEQ ID NO: 20)
```

A first amplification is performed using primers 820-2745.c and 35S/RCMV5'.r using plasmid 820 as a template to produce a fragment containing the truncated 35S promoter (fragment A). In parallel, a second amplification is performed with the primers RCMV5'.1c and RCMV5'/C5-1 LC.r on a plasmid containing the RCMV RNA-2 clone to produce a fragment containing the 5' region of the RCMV RNA-2 (fragment B). A third reaction amplifies the antibody light chain using primers C5-1 LC.1c and C5-1 LC/StuI.r on plasmid 820 (fragment C). Fragment A and B are then mixed together with primers 820-2745.c and RCMV5'/C5-1 LC.r in an amplification reaction to produce a fragment (fragment AB) containing the 35S promoter linked to the 5' region of the RCMV. A final amplification reaction contains fragments AB and C with primers 820-2745.c and C5-1 LC/StuI.r. The reaction product contains the 35S promoter, the 5' region of RCMV and C5-1 light chain coding region with an ApaI restriction site upstream of C5-1 initial ATG (fragment ABC). Fragment ABC is digested with PacI and HpaI and inserted between the same sites in plasmid 820. The resulting plasmid, named 820RCMVtruncated5', contains the 5' region of RCMV flanked upstream by the 35S promoter and downstream by C5-1 light chain coding region.

To insert the 3' region of the RCMV, an PCR amplification is performed using primers C5-1 LC.1c and C5-1 LC/RCMV3'.r and plasmid 820 as template to produce a fragment containing the light chain of C5-1 (fragment D). In parallel, another amplification is performed using primers RCMV3'.c and RCMV3'/polyA/EcoRI.r with a plasmid containing the RCMV RNA-2 clone to produce a fragment containing the 3' region of the RCMV RNA-2 (fragment E). Fragments D and E are mixed together with primers C5-1 LC.1c and RCMV3'/polyA/EcoRI.r in an amplification reaction to produce fragment DE, containing C5-1 light chain coding region linked to the 3' region of RCMV RNA-2, with a StuI site downstream of C5-1 Stop codon. Fragment DE is digested with HpaI and EcorI and inserted in 820RCMVtruncated5' previously digested with the same restriction enzymes. The resulting plasmid, named 850, contains C5-1 light chain gene in a deleted RCMV RNA-2.

Plasmid 820RCMV can be used as an accepting plasmid to clone other genes of interest using ApaI and StuI restriction sites. For example, the heavy chain of C5-1 is amplified from plasmid 822 using primers ApaI-HC(C5-1)-1c and HC(C5-1)-StuI.r, and the amplified fragment is digested with ApaI before being inserted in plasmid 850 previously digested with ApaI and StuI. The resulting plasmid is named 852. The RCMV-based plasmids are shown in FIG. 13. The plasmids are transfected into *Agrobacterium tumefaciens* strain AGL1, and the transient expression is performed as described in previous Examples 8 and 9, and immunological detection is performed as previously described (Protein Methods (Bollag D M, Rozycki M D, Edelstein S J Eds., Wiley-Liss-Publishers, $2^{nd}$ edition (1996)).

REFERENCES

Angell, S. M. and Baulcombe, D. C. (1997) Consistent gene silencing in transgenic plants expressing a replicating potato virus X RNA. EMBO J. 16, 3675-3684.

Angell, S. M. and Baulcombe, D. C. (1999) Potato virus X amplicon-mediated silencing of nuclear genes. Plant J. 20, 357-362.

Birch-Machin, I., Newell, C. A., Hibberd, J. M. and Gray, J. C. (2004) Accumulation of rotavirus VP6 protein in chloroplasts of transplastomic tobacco is limited by protein stability. Plant Biotechnol. J. 2, 261-270.

Cañizares, M. C., Taylor, K. M. and Lomonossoff, G. P. (2004) Surface-exposed C-terminal amino acids of the small coat protein of Cowpea mosaic virus are required for suppression of silencing. J. Gen. Virol. 85, 3431-3435.

Castilla J., Pintado, B., Sola, I., Sanchez-Morgado, J. M. and Enjuanes, L. (1998). Engineering passive immunity in transgenic mice secreting virus-neutralizing antibodies in milk. Nature Biotechnol. 16, 349-354.

Castilla J., Sola, I. and Enjuanes, L. (1997). Interference of coronavirus infection by expression of immunoglobulin G (IgG) or IgA virus-neutralizing antibodies. J. Virol. 71, 5251-5258.

Daniell, H., Khan, M. S. and Allison, L. (2002) Milestones in chloroplast genetic engineering: an environmentally friendly era in biotechnology. Trends Plant Sci. 7, 84-91.

D'Aoust, M.-A., Lerouge, P., Busse, U., Bilodeau P., Trépanier S., Gomord V., Faye L. and Vézina L.-P. Efficient and reliable production of pharmaceuticals in alfalfa, in Molecular Farming Plant-made Pharmaceuticals and Technical Proteins. Wiley-VCH (Rainer Fischer and Stephan Schillberg Eds.).

De Cosa, B., Moar, W., Lee, S-B., Miller, M. and Daniell, H. (2001) Overexpression of the Bt cry2Aa2 operon in chloroplasts leads to formation of insecticidal crystals. Nature Biotech. 19, 71-74.

Gebauer F., Posthumus, W. A. P., Correa, I., Sufie, C., Sanchez, C. M., Smerdou, C., Lenstra, J. A., Meloen, R. and Enjuanes, L. (1991). Residues involved in the formation of the antigenic sites of the S protein of transmissible gastroenteritis coronavirus. Virology 183, 225-238.

Gleba, Y., Industrial processes based on viral expression systems. Conference on Plant-Made Pharmaceuticals, Montreal, Canada (Jan. 30 to Feb. 2, 2005).

Goldbach, R. W. and Wellink, J. (1996) Comoviruses: molecular biology and replication. In: The Plant Viruses, volume 5 (Harrison, B. D. and Murant, A. F., eds.), pp. 35-76. Plenum Press, New York.

Gopinath, K., Wellink, J., Porta, C., Taylor, K. M., Lomonossoff, G. P. and van Kammen, A. (2000) Engineering cowpea mosaic virus RNA-2 into a vector to express heterologous proteins in plants. Virology 267, 159-173.

Hamilton, A., Voinnet, O., Chappell, L. and Baulcombe, D. (2002) Two classes of short interfering RNA in RNA silencing. EMBO J. 21, 4671-4679.

Holness, C. L., Lomonossoff, G. P., Evans, D. and Maule, A. J. (1989). Identification of the initiation codons for translation of cowpea mosaic virus middle component RNA using site directed mutagenesis of an infectious cDNA clone. Virology 172, 311 320.

Horsch, R. B. et al (1985) A simple and general method for transferring genes into plants. Science 227, 1229-1231.

Hull A. K., Criscuolo C. J., Mett V., Groen H., Steeman W., Westra H., Chapman G., Legutki B., Baillie L. and Yusibov V. (2005) Human-derived, plant-produced monoclonal antibody for the treatment of anthrax. Vaccine 23, 2082-2086.

Kaido, M., Mori, M., Mise, K., Okuno, T. and Furusawa I. (1995) Inhibition of brome mosaic virus (BMV) amplification in protoplasts from transgenic tobacco plants expressing replicable BMV RNAs. J. Gen. Virol. 76, 2827-2833.

Kapila, J., De Rycke, R., Van Montagu, M. and Angenon G (1997) An *Agrobacterium*-mediated transient gene expression system for intact leaves. Plant Science 122, 101-108.

Kathuria, S. R., Nath, R., Pal, R., Singh, O., Fischer, R., Lohiya, N. K. and Talwar, G. P. (2002) Functional recombinant antibodies against human chorionic gonadotropin expressed in plants. Curr. Sci. 82, 1452-1457.

Koprowski, H. and Yusibov, V. (2001) The green revolution: plants as heterologous expression vectors. Vaccine 19, 2735-2741.

Li E, Pedraza, A., Bestagno, M., Mancardi, S., Sanchez, R. and Burrone, O. R. (1997) Mammalian cell expression of dimeric small immune proteins (SIP). Protein Eng. 10, 731-736.

Liu, L., Grainger, J., Cañizares, M. C., Angell, S. M. and Lomonossoff, G. P. (2004) Cowpea mosaic virus RNA-1 acts as an amplicon whose effects can be counteracted by a RNA-2-encoded suppressor of silencing. Virology 323, 37-48.

Liu, L. and Lomonossoff, G. P. (2002) Agroinfection as a rapid method for propagating Cowpea mosaic virus-based constructs. J. Virol. Meth. 105, 343-348. Liu, L., Cañizares, M. C., Monger, W., Perrin, Y., Tsakiris, E., Porta, C., Shariat, N., Nicholson, L. and Lomonossoff, G. P. (2004). Cowpea mosaic virus-based systems for the production of antigens and antibodies in plants. Vaccine 23, 1788-1792.

Lomonossoff, G. P. & Hamilton, W. D. O. (1999) Cowpea mosaic virus-based vaccines. Curr. Topics Microbiol. Immunol. 240, 177-189.

Mallory, A. C., Parks, G., Endres, M. W., Baulcombe, D., Bowman, L. H., Pruss, G. J. and Vance, V. B. (2002) The amplicon-plus system for high-level expression of transgenes in plants. Nature Biotechnol. 20, 622-625.

Marillonnet S. Expression of protein fusions and of single chain and monoclonal antibodies in plants using viral vectors. Plant-Based Vaccines and Antibodies meeting, Prague, Czech Republic (Jun. 8 to 10, 2005).

Mori, M., Fujihara, N., Mise, K. and Furusawa, I. (2001) Inducible high-level mRNA amplification system by viral replicase in transgenic plants. Plant J. 27, 79-86.

Mori, M., Kaido, M., Okuno, T. and Furusawa, I. (1993) Messenger-RNA amplification system by viral replicase in transgenic plants. FEBS Lett. 336, 171-174.

Rodríguez, M., Ramírez, N. I., Ayala, M., Freyre F., Pérez L., Triguero A., Mateo C., Selman-Housein G., Gavilondo J. V. and Pujol M. (2005) Transient expression in tobacco leaves of an aglycosylated recombinant antibody against the epidermal growth factor receptor. Biotech. Bioeng. 89, 188-194.

Rohll, J. B., Holness, C. L., Lomonossoff, G. P. and Maule, A. J. (1993). 3' terminal nucleotide sequences important for the accumulation of cowpea mosaic virus M-RNA. Virology 193, 672-679.

Sola, I., Castilla, J. Pintado, J., Sanchez-Morgado, J. M., Whitelaw, C. B. A. and Enjuanes, L. (1998). Transgenic mice secreting coronavirus neutralizing antibodies in milk. J. Virol. 72, 3762-3772.

Suñe, C., Jiménez, G., Correa, I., Bullido, M. J., Gebauer, F., Smerdou, C. and Enjuanes, L. (1990). Mechanisms of transmissible gastro-enteritis coronavirus neutralisation. Virology 177, 559-569.

Usha, R., Rohll, J. B., Spall, V. E., Shanks, M., Maule, A., Johnson, J. E. and Lomonossoff, G. P. (1993) Expression of an animal virus antigenic site on the surface of a plant virus particle. Virology 197, 366-374.

van Bokhoven, H., Le Gall, O, Kasteel, D., Verver, J., Wellink, J. and van Kammen, A. (1993). Cis- and Trans-acting Elements in Cowpea Mosaic Virus RNA Replication. Virology 195, 377-386.

van Engelen, F. A., Molthoff, J. W., Conner, A. J., Nap, J. P., Pereira, A. and Stiekema, W. J. (1995) pBINPLUS: an improved plant transformation vector based on pBIN19. Transgenic Res. 4, 288-290.

Vaquero, C., Sack, M., Chandler, J., Drossard, J., Schuster, F., Moneche, M., Schillberg, S. and Fischer, R. (1999) Transient expression of a tumor-specific single-chain fragment and a chimeric antibody in tobacco leaves. Proc. Natl. Acad. Sci. USA, 96, 11128-11133.

Verch, T., Yusibov, V. and Koprowski, H. (1998) Expression and assembly of a full-length monoclonal antibody in plants using a plant virus vector. J. Immunol. Meth. 220, 69-75.

Walmsley, A. M. and Arntzen, C. J. (2003) Plant cell factories and mucosal vaccines. Curr. Opin. Biotechnol. 14, 145-150.

Bollag, D. M., Rozycki, M. D. and Edelstein, S. J. (1996) Protein Methods, 2nd Edition.

John Wiley and sons Publishers. ISBN 0-471-11837-0.

Darveau, A., Pelletier, A., Perreault, J. (1995) PCR-mediated synthesis of chimeric molecules. Methods in Neurosciences 26: 77-85.

Brigneti, G., Voinnet, O., Li, W. X., Ji, L. H., Ding, S. W and Baulcombe, D. C. (1998) Viral pathogenicity determinants are suppressors of transgene silencing in *Nicotiana benthamiana*. EMBO Journal 17: 6739-6746.

Gopinath, K., Wellink, J., Porta, C., Taylor, K. M., Lomonossoff, G. P. and van Kammen, A. (2000) Engineering cowpea mosaic virus RNA-2 into a vector to express heterologous proteins in plants. Virology 267: 159-173.

Liu, L. and Lomonossoff, G. P. (2002) Agroinfection as a rapid method for propagating Cowpea mosaic virus-based constructs. Journal of Virological Methods 105: 343-348.
Lin, T., Clark, A. J., Chen, Z., Shanks, M., Dai, J.-B., Li, Y., Schmidt, T., Oxelfelt, Lomonossoff, G. P. and Johnson, J. E. (2000). Structural fingerprinting: subgrouping of Comovirus by structural studies of red clover mottle virus to 2.4Å resolution and comparisons with other comoviruses. Journal of Virology 74, 493-504.
Shanks, M., Tomenius, K., Clapham, D., Huskisson, N. S., Barker, P. J., Wilson, I. G., Maule, A. J. and Lomonossoff, G. P. (1989). Identification and subcellular localisation of a putative cell to cell transport protein in red clover mottle virus. Virology 173, 400 407.
Shanks, M. and Lomonossoff, G. P. (1992). The nucleotide sequence of red clover mottle virus bottom component RNA. Journal of General Virology 73, 2473 2477.
Shanks, M., Stanley, J. and Lomonossoff, G. P. (1986). The primary structure of red clover mottle virus middle component RNA. Virology 155, 697 706.
Shanks, M., Dessens, J. T. and Lomonossoff, G. P. (1996). The 24 kDa proteinases of comoviruses are virus-specific in cis as well as in trans. Journal of General Virology 77, 2365-2369.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A plant gene expression system comprising:
   (a) a first gene construct comprising a truncated RNA-2 of a Cowpea Mosaic virus(CPMV)genome having the sequence of SEQ ID NO: 22, wherein the RNA-2 sequence between nucleotides 512 or 524 and 3300 of SEQ ID NO: 22 have been replaced with at least one foreign gene encoding a heterologous protein of interest, said truncated RNA-2 being operably linked to promoter and terminator sequences functional in a plant cell, wherein said truncation of the RNA-2 is such that no infectious viral particles are produced which could spread to other plants in the environment and expression of viral movement proteins and coat proteins is prevented;
   (b) a second gene construct comprising RNA-1 of said Comovirus bipartite virus genome operably linked to promoter and terminator sequences functional in a plant cell; and (c) a third gene construct, optionally incorporated within said first gene construct, said second gene construct or both, comprising a suppressor of gene silencing operably linked to promoter and terminator sequences functional in a plant cell.

2. The system according to claim 1 wherein said constructs are expressed transiently or stably incorporated in plant cells.

3. The system according to claim 1 wherein at least one construct is expressed transiently and at least one construct is stably integrated into the genome of said plant cell.

4. The system according to claim 1 wherein said suppressor of gene silencing is selected from HcPro from Potato virus Y, HcPro from tobacco etch virus (TEV), PI9 from tomato bushy stunt virus (TBSV), rgscam, B2 protein from flock house virus (FHV), the small coat protein of cowpea mosaic virus (CPMV), and coat protein from turnip crinkle virus (TCV).

5. The expression system according to claim 1, wherein said heterologous protein of interest is selected from the group consisting of cytokines, vaccines, enzymes, growth factors, receptors, interferons, hematopoeitic agents, pituitary hormones, thyroid hormones, hypothalamic hormones, albumin, insulin and pancreatic hormones.

6. A plant comprising the gene expression system of claim 1.

7. A plant cell or progeny obtained from the plant of claim 6, said plant cell or progeny comprising said gene expression system.

8. A method for expressing a foreign gene in a plant cell which comprises
   (a) providing a first gene construct, said construct comprising at least one truncated RNA-2 construct of a Cowpea Mosaic virus (CPMV) genome having the sequence of SEQ ID NO: 22, wherein the RNA-2 sequence between nucleotides 512 or 524 and 3300 of SEQ ID NO: 22 have been replaced with at least one nucleic acid encoding a heterologous protein of interest, said truncated RNA-2 being operably linked to promoter and terminator sequences functional in a plant cell, wherein said truncation of the RNA-2 is such that no infectious viral particles are produced which could spread to further plants in the environment, wherein said truncation of the RNA-2 prevents the expression of viral movement proteins and coat proteins;
   (b) providing a second gene construct, said construct comprising RNA-1 of said Comovirus bipartite virus genome; and
   (c) providing a third construct encoding a suppressor of gene silencing into said plant cell;
   (d) introducing said first, second and third constructs into a plant cell, thereby producing said heterologous protein of interest.

9. The method according to claim 8, wherein said first, second, and third constructs are introduced into said plant cell simultaneously.

10. The method according to claim 8, wherein at least one construct is stably integrated into the genome of said plant cell and wherein at least one construct is expressed transiently.

11. The method according to claim 8 wherein said one or more truncated RNA-2 constructs are stably introduced into plant cells and said RNA-1 and suppressor of silencing are provided in trans by agroinoculation of said plant cells.

12. The method according to claim 8, wherein at least one construct is introduced into said plant cell via crossing.

13. The method according to claim 10 wherein stable transformation and transient expression are performed in different locations such that no agrobacterium carrying a gene of interest is manipulated in an area where the production and harvest of a product of gene expression is performed.

14. The method according to claim 8 wherein said suppressor of gene silencing is selected from HcPro from Potato virus Y, HcPro from TEV, P19 from TBSV, rgscam, B2 protein from FHV, the small coat protein of CPMV, and coat protein from TCV.

15. A method for expressing an antibody in a plant cell which comprises
   (a) providing a first gene construct into said plant cell, said construct comprising a first truncated RNA-2 of a Cowpea Mosaic virus (CPMV) genome having the sequence of SEQ ID NO: 22,
      wherein the RNA-2 sequence between nucleotides 512 or 524 and 3300 of SEQ ID NO: 22 have been replaced with nucleic acid encoding the heavy chain of an antibody, said truncated RNA-2 being operably linked to promoter and terminator sequences functional in a plant cell;
      and a second truncated RNA-2 of a Cowpea Mosaic virus (CPMV) genome having the sequence of SEQ ID NO: 22,
      wherein the RNA-2 sequence between nucleotides 512 or 524 and 3300 of SEQ ID NO: 22 have been replaced with a nucleic acid encoding the light chain of an antibody, said second truncated RNA-2 being operably linked to promoter and terminator sequences functional in a plant cell, wherein said truncation of the RNA-2 is such that no infectious viral particles are produced which could spread to further plants in the environment and the expression of viral movement proteins and coat proteins is prevented;
   (b) providing a second gene construct into said plant cell, said second gene construct comprising RNA-1 of said CPMV genome; and
   (c) providing a third gene construct encoding a suppressor of gene silencing into said plant cell;
   (d) introducing said first, second and third gene constructs into said plant cell, thereby expressing said antibody of interest.

16. The method according to claim 15, further comprising extracting and isolating said antibody from said plant cells.

17. The method according to claim 15 wherein replication of said truncated RNA-2 is achieved by supplying said suppressor of gene silencing and said RNA-1, either exogenously or by crossing.

18. A plant comprising the plant cell produced by the method of claim 8, wherein the plant cell comprises said first, second, and third constructs.

19. A plant producing an antibody comprising the plant cell produced by the method of claim 15, wherein the plant cell comprises said first, second, and third constructs.

20. The expression system according to claim 1 further comprising a second truncated RNA-2 of the CPMV genome carrying a foreign gene encoding a further heterologous protein of interest operably linked to promoter and terminator sequences functional in a plant cell, wherein said truncation of the RNA-2 is such that no infectious virus is produced which could spread to further plants in the environment and the expression of viral movement proteins and coat proteins is prevented.

21. The expression system according to claim 20, wherein said heterologous proteins of interest together form a multimeric protein.

22. The method according to claim 8 wherein the method further comprises providing a second truncated RNA-2 of the CPMV genome carrying a further nucleic acid encoding a further heterologous protein of interest operably linked to promoter and terminator sequences functional in a plant cell, wherein said truncation of the RNA-2 is such that no infectious viral particles are produced which could spread to further plants in the environment and the expression of viral movement proteins and coat proteins is prevented.

23. The method according to claim 22 wherein said at least one nucleic acid and further nucleic acid together encode a multimeric protein.

24. The method according to claim 23 wherein said multimeric protein is an antibody.

25. The method according to claim 23 wherein said multimeric protein is a vaccine antigen.

* * * * *